(12) United States Patent
Kaneda et al.

(10) Patent No.: US 8,980,257 B2
(45) Date of Patent: Mar. 17, 2015

(54) ANTIBODY BEING CAPABLE OF BINDING TO TRANSFORMING GROWTH FACTOR ALPHA AND HAVING GROWTH-SUPPRESSING ACTIVITY ON CANCERS HAVING RAS GENE MUTATION

(75) Inventors: Makoto Kaneda, Ina (JP); Yoshihiro Fujii, Ina (JP); Yoshihiro Hayata, Ina (JP); Yoshiro Kishi, Ina (JP); Ichiro Yahara, Ina (JP)

(73) Assignee: Medical & Biological Laboratories Co., Ltd., Aichi (JP)

( * ) Notice: Subject to any disclaimer, the term of this patent is extended or adjusted under 35 U.S.C. 154(b) by 0 days.

(21) Appl. No.: 13/698,420

(22) PCT Filed: May 17, 2011

(86) PCT No.: PCT/JP2011/061347
§ 371 (c)(1),
(2), (4) Date: Jan. 30, 2013

(87) PCT Pub. No.: WO2011/145629
PCT Pub. Date: Nov. 24, 2011

(65) Prior Publication Data
US 2013/0131322 A1  May 23, 2013

(30) Foreign Application Priority Data
May 18, 2010  (JP) ................................. 2010-114460

(51) Int. Cl.
| | | |
|---|---|---|
| *A61K 39/00* | (2006.01) | |
| *A61K 39/395* | (2006.01) | |
| *C07K 16/00* | (2006.01) | |
| *C07K 16/18* | (2006.01) | |
| *C07K 16/24* | (2006.01) | |
| *C12N 15/00* | (2006.01) | |
| *C12N 15/09* | (2006.01) | |
| *C12N 15/11* | (2006.01) | |
| *C12N 15/13* | (2006.01) | |
| *C12N 15/63* | (2006.01) | |
| *C12N 5/10* | (2006.01) | |
| *C12N 5/16* | (2006.01) | |
| *C12N 5/18* | (2006.01) | |
| *C12N 5/20* | (2006.01) | |
| *C12N 5/22* | (2006.01) | |
| *C12N 5/24* | (2006.01) | |
| *C12N 5/26* | (2006.01) | |
| *C12N 5/28* | (2006.01) | |
| *C07K 16/22* | (2006.01) | |
| *C07K 14/495* | (2006.01) | |

(52) U.S. Cl.
CPC ............... *C07K 16/22* (2013.01); *C07K 14/495* (2013.01); *A61K 2039/505* (2013.01); *C07K 2317/24* (2013.01); *C07K 2317/76* (2013.01)

USPC .................. 424/130.1; 424/133.1; 424/135.1; 424/139.1; 424/141.1; 424/142.1; 424/145.1; 530/387.1; 530/387.3; 530/387.9; 530/388.1; 530/388.15; 530/388.23; 435/69.1; 435/325; 435/326; 435/328; 435/331; 435/335; 435/252.3; 435/254.11; 435/320.1; 536/23.1; 536/23.5; 536/23.53

(58) Field of Classification Search
None
See application file for complete search history.

(56) References Cited

U.S. PATENT DOCUMENTS

| 5,190,858 A | 3/1993 | Sorvillo et al. |
|---|---|---|
| 2013/0131322 A1* | 5/2013 | Kaneda et al. ........... 530/388.24 |

OTHER PUBLICATIONS

Paul, Fundamental Immunology, 1993, 3$^{rd}$ edition, Raven Press, NY, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
Eisen et al., 2014, Curr. Oncol. Rep. 16(370):1-6.*
A. B. Roberts et. al, "Isolation From Murine Sarcoma Cells of Novel Transforming Growth Factors Potentiated by EGF", Nature, Feb. 4, 1982, p. 417-419. vol. 295.
Alain B. Schreiber et. al, "Transforming Growth Factor-α: A More Potent Angiogenic Mediator Than Epidermal Growth Factor", Science, 1986, pp. 1250-1253, vol. 232.
Alberto Bardelli et. al, "Molecular Mechanisms of Resistance to Cetuximab and Panitumumab in Colorectal Cancer", Journal of Clinical Oncology, Biology of Neoplasia, Mar. 1, 2010, pp. 1254-1261, vol. 28, No. 7.
Ami Citri et. al,"EGF-ERBB Signalling: Towards the Systems Level", Nature Reviews, Molecular Cell Biology , Jul. 2006, pp. 505-516, vol. 7.
Amir Onn et. al, "Synchronous Overexpression of Epidermal Growth Factor Receptor and HER2-neu Protein Is a Predictor of Poor Outcome in Patients with Stage I Non-Small Cell Lung cancer", Clinical Cancer Research, Jan. 1, 2004, pp. 136-143, vol. 10.
Anita B. Roberts et. al, "Transforming Growth Factors: Isolation of Polypeptides From Virally and Chemically Transformed Cells by Acid/Ethanol Extraction", Cell Biology, Proc. Natl. Acad. Sci. USA , Jun. 1980, pp. 3494-3498, vol. 77, No. 6.

(Continued)

*Primary Examiner* — Elizabeth C Kemmerer
(74) *Attorney, Agent, or Firm* — Sughrue Mion, PLLC

(57) ABSTRACT

It has been found out that among antibodies showing reactivity with wild type TGF-α, antibodies less reactive with G79A-substituted TGF-α have an excellent growth-suppressing effect on cancer cells having a mutated Ras gene. Further, it has been found out that most of these antibodies have an activity of inhibiting EGFR tyrosine phosphorylation and/or an induction-suppressing activity on vascular endothelial cells.

19 Claims, 26 Drawing Sheets
(2 of 26 Drawing Sheet(s) Filed in Color)

(56) References Cited

OTHER PUBLICATIONS

Antonio Marchetti et. al, "Clinical Implications of KRAS Mutations in Lung Cancer Patients Treated with Tyrosine Kinase Inhibitors: An Important Role for Mutations in Minor Clones", Neoplasia, Oct. 2009, pp. 1084-1092, vol. 11, No. 10.

Arata Goto et. al, "A Novel Anti-EGFR Monoclonal Antibody, Cetuximab (Erbitux)", Japanese Journal of Lung Cancer, The 20th Lung Cancer workshop, Jun. 20, 2006, pp. 267-275, vol. 46, No. 3.

Arnon Rosenthal et. al, "Expression in Rat Fibroblasts of a Human Transforming Growth Factor-α cDNA Results in Transformation", Cell, Jul. 18, 1986, pp. 301-309, vol. 46, Cell Press.

Atanasio Pandiella et. al, "Cleavage of the Membrane Precursor for Transforming Growth Factor α is a Regulated Process", Cell Biology, Proc. Natl. Acad. Sci., USA, Mar. 1991, pp. 1726-1730, vol. 88.

C Mascaux et. al, "The Role of RAS Oncogene in Survival of Patients with Lung Cancer: A Systematic Review of the Literature with Meta-Analysis", British Journal of Cancer, 2005, pp. 131-139, No. 92, Cancer Research UK.

Channing J. Der et. al, "rasH Mutants Deficient in GTP Binding", Molecular and Cellular Biology, Sep. 1986, pp. 3291-3294, vol. 6, No. 9, American Society for Microbiology.

Channing J. Der et. al, "Transforming Genes of Human Bladder and Lung Carcinoma Cell Lines are Homologous to the ras Genes of Harvey and Kirsten Sarcoma Viruses", Medical Sciences, Proc. Natl. Acad Sci., USA, Jun. 1982, pp. 3637-3640, vol. 79.

Cheryl H. Baker et. al, "Phosphorylated Epidermal Growth Factor Receptor on Tumor-Associated Endothelial Cells in Human Renal Cell Carcinoma Is a Primary Target for Therapy by Tyrosine Kinase Inhibitors, Neolasia", Jun. 2006, pp. 470-476, vol. 8, No. 6.

Chi Liu et. al, "In Vitro and in Vivo Expressions of Transforming Growth Factor-α and Tyrosine Kinase Receptors in Human Non-Small-Cell Lung Carcinomas", American Journal of Pathology, Apr. 1993, pp. 1155-1162, vol. 142, No. 4, American Society for Investigative Pathology.

Christos S. Karapetis et. al, "K-ras Mutations and Benefit from Cetuximab in Advanced Colorectal Cancer", The New England Journal of Medicine, Oct. 23, 2008, pp. 1757-1765, vol. 359, No. 17.

Cory J. Xian et. al, "Specificity of the Localization of Transforming Growth Factor-α Immunoreactivity in Colon Mucosa", The Journal of Histochemistry & Cytochemistry, 1999, pp. 949-957, vol. 47 No. 7, The Histochemical Society, Inc.

"K-ras Mutations and Cetuximab in Colorectal Cancer", Correspondence (Letters to the Editor), New England Journal of Medicine, Feb. 19, 2009, pp. 833-836, vol. 360, No. 8.

David A. Eberhard et. al, "Mutations in the Epidermal Growth Factor Receptor and in KRAS Are Predictive and Prognostic Indicators in Patients With Non-Small-Cell Lung Cancer Treated With Chemotherapy Alone and in Combination With Erlotinib", Journal of Clinical Oncology, Sep. 1, 2005, vol. 23, No. 25, American Society of Clinical Oncology, pp. 5900-5909.

Erbitux Drug Interview Form Approved by the Ministry of Health, Labor and Welfare in Japan, Sep. 2008, 55 pages; Erbitux Product description approved by the USFDA, 2004, 18 pages.

Esther H. Chang et. al, "Human Genome Contains Four Genes Homologous to Transforming Genes of Harvey and Kirsten Murine Sarcoma Viruses", Biochemistry, Aug. 1982, pp. 4848-4852, vol. 79, Proc. Natl. Acad. Sci. USA.

Floriana Morgillo et. al, "Primary and Acquired Resistance to Anti-EGFR Targeted Drugs in Cancer Therapy", Differentiation, pp. 788-799, International Society of Differentiation, 2007.

Fortunato Ciardiello et. al, "Transforming Growth Factor-α Expression Is Enhanced in Human Mammary Epithelial Cells Transformed by an Activated c-Ha-ras Protooncogene but not by the c-neu Protooncogene, and Overexpression of the Transforming Growth Factor-α Complementary DNA Leads to Transformation", Cell Growth & Differentiation, Sep. 1990, pp. 407-420, vol. 1.

Fortunato Ciardiello, MD et. al, "EGFR Antagonists in Cancer Treatment", The New England Journal of Medicine, 2008, pp. 1160-1174, Massachusetts Medical Society. vol. 358.

Franklin J. Moy, et al., "Solution of Human Type-α Transforming Growth Factor Determined by Heteronuclear NMR Spectroscopy and Refined by Energy Minimization with Restraints", Biochemistry, 1993, pp. 7334-7353, vol. 32, American Chemical Society.

Georg Lurje et. al, "EGFR Signaling and Drug Discovery", Oncology, Review, 2009, pp. 400-410, No. 77, Karger AG, Basel.

Hans Marquardt et. al,"Transforming Growth Factors Produced by Retrovirus-Transformed Rodent Fibroblasts and Human Melanoma Cells: Amino Acid Sequence Homology with Epidermal Growth Factor", Biochemistry, Proc. Natl. Acad. Sci., USA , Aug. 1983, pp. 4684-4688, vol. 80.

Helmout Modjtahedi, et. al, "Differentiation or Immune Destruction: Two Pathways for Therapy of Squamous Cell Carcinomas with Antibodies to the Epidermal Growth Factor Receptor", Cancer Research, Apr. 1, 1994, pp. 1695-1701, vol. 54.

James P. Tam, et al., "Efficient Synthesis of Human Type α Transforming Growth Factor: Its Physical and Biological Characterization", Biochemistry, Proc. Natl. Acad. Sci. USA, Nov. 1986, pp. 8082-8086, vol. 83.

John Mendelsohn, "Blockade of Receptors for Growth Factors: An Anticancer Therapy—The Fourth Annual Joseph H. Burchenal American Association for Cancer Research Clinical Research Award Lecture", Clinical Cancer Research, Mar. 2000, pp. 747-753, vol. 6.

Joseph De Larco et. al, "Growth Factors from Murine Sarcoma Virus-Transformed Cells", Microbiology, Proc. Natl. Acad. Sci. USA, Aug. 1978, pp. 4001-4005, vol. 75, No. 8.

Kranenburg, "The KRAS Oncogene: Past, Present, and Future", biochimica et Biophysica Acta, 2005, pp. 81-82, vol. 1756.

Lillian Shum et. al, "Association of the Transmembrane TGF-α Precursor with a Protein Kinase Complex", The Journal of Cell Biology, May 1994, pp. 903-916, vol. 125.

M. R. Alison et. al, "Transforming Growth Factor-α Immunoreactivity in a Variety of Epithelial Tissues", Cell Prolif., 1993, pp. 449-460, vol. 26.

Maria Borrell-Pages et. al, "TACE is Required for the Activation of the EGFR by TGF-α in Tumors", The EMBO Journal, 2003, pp. 1114-1124, vol. 22 No. 5, European Molecular Biology Organization.

Mario A. Anzano et. al, "Sarcoma Growth Factor From Conditioned Medium of Virally Transformed Cells is Composed of Both Type α and type β Transforming Growth Factors", Cell Biology, Proc. Natl. Acad. Sci., USA , Oct. 1983, pp. 6264-6268, vol. 80.

Mario A. Anzano et. al, "Synergistic Interaction of Two Classes of Transforming Growth Factors from Murine Sarcoma Cells", Cancer Research, Communication, Nov. 1982, p. 4776-4778, vol. 42.

Preeta Tyagi, PhD, et. al, "Recent Results and Ongoing Trials with Panitumumab (ABX-EGF), a Fully Human Anti-Epidermal Growth Factor Receptor Antibody, in Metastatic Colorectal Cancer", Clinical Colorectal Cancer, May 2005, pp. 21-23.

Qian JF., et al, "Human Transforming Growth Factor Alpha: sequence analysis of the 4.5-kb and 1.6-kb mRNA species"., Gene, 1993, vol. 132, No. 2, pp. 291-296, entire text.

Rachel Wong et. al,"Using Predictive Biomarkers to Select Patients With Advanced Colorectal Cancer for Treatment With Epidermal Growth Factor Receptor Antibodies", Journal of Clinical Oncology, Dec. 10, 2008, pp. 5668-5670, vol. 26, No. 35.

Raja R. Seethala, et al. "Immunohistochemical Analysis of Phosphotyrosine Signal Transducer and Activator of Transcription 3 and Epidermal Growth Factor Receptor Autocrine Signaling Pathways in Head and Neck Cancers and Metastatic Lymph Nodes", (Review) Clin Cancer Res, Mar. 1, 2008, pp. 1303-1309, vol. 14, No. 5.

Raquel Soares et. al, "Expression of TGF-α and EGFR in Breast Cancer and its Relation to Angiogenesis", The Breast Journal, 2000, pp. 171-177, vol. 6 No. 3.

Raymond C. Harris et. al, "EGF Receptor Ligands", Experimental Cell Research, 2003, pp. 2-13, vol. 284.

Rik Derynck et. al, "Synthesis of Messenger RNAs for Transforming Growth Factors α and β and the Epidermal Growth Factor Receptor by Human Tumors", Cancer Research, Feb. 1, 1987, pp. 707-712, vol. 47.

(56) References Cited

OTHER PUBLICATIONS

Roy S. Herbst MD, et. al, "Lung Cancer", The New England Journal of Medicine, 2008, pp. 1367-1380, Massachusetts Medical Society vol. 359.

Shigeki Higashiyama et. al,"Membrane-Anchored Growth Factors, the Epidermal Growth Factor Family: Beyond Receptor Ligands", Cancer Sci, Feb. 2008, pp. 214-220, No. 2, vol. 99, Japanese Cancer Association.

Shiqing Li, et. al, "Structural Basis for Inhibition of the Epidermal Growth Factor Receptor by Cetuximab", Cancer Cell, Apr. 2005, pp. 301-311, vol. 7.

Thomas P.J. Garrett et. al, "Crystal Structure of a Truncated Epidermal Growth Factor Receptor Extracellular Domain Bound to Transforming Growth Factor α", Cell, Sep. 20, 2002, pp. 763-773, vol. 110.

Toshinari Minamoto, MD et. al, "K-ras Mutation: Early Detection in Molecular Diagnosis and Risk Assessment of Colorectal, Pancreas, and Lung Cancers—A Review", Cancer Detection and Prevention, 2000 pp. 1-12 , vol. 24, No. 1.

V. Baselga et. al, "Differential Expression of the Epidermal Growth Factor Receptor and Its Ligands in Primary Non-Small Cell Lung Cancers and Adjacent Benign Lung", Cancer Research, May 15, 1993, pp. 2379-2385, vol. 53.

Valerie Rusch et. al, "Overexpression of the Epidermal Growth Factor Receptor and Its Ligand Transforming Growth Factor α Is Frequent in Resectable Non-Small Cell Lung Cancer but Does Not Predict Tumor Progression", Clinical Cancer Research, Apr. 1997, pp. 515-522, vol. 3.

Wenjuan Wu et. al, "Expression of Epidermal Growth Factor (EGF)/Transforming Growth Factor-∝ by Human Lung Cancer Calles Determines Their Response to EGF Receptor Tyrosine Kinase Inhibition in the Lungs of Mice", Mol Cancer Ther, Oct. 2007, pp. 2652-2663, vol. 6, No. 10.

Zhen Fan, et. al, "Antibody-Induced Epidermal Growth Factor Receptor Dimerization Mediated Inhibition of Autocrine Proliferation of A431 Squamous Carcinoma Cells", The Journal of Biological Chemistry, Nov. 4, 1994, pp. 27595-27602, vol. 269, No. 44, The American Society for Biochemistry and Molecular Biology, Inc., USA.

Zhigang Li et. al, "TGF-α as well as VEGF, PD-ECGF and bFGF Contribute to Angiogenesis of Esophageal Squamous Cell Carcinoma", International Journal of Oncology, 2000, pp. 453-460, vol. 17.

Sorvillo, John M. et. al. "Preparation and characterization of monoclonal antibodies specific for human transforming growth factor alpha," Oncogene (1990) vol. 5, 377-386.

International Search Report, dated Nov. 1, 2011.

Extended European Search Report in European Application No. 11783563.7 dated Apr. 10, 2014.

Putnam et al., "Autocrine growth stimulation by transforming growth factor-α in human non-small cell lung cancer", Surgical Oncology, 1992, 1:49-60.

* cited by examiner

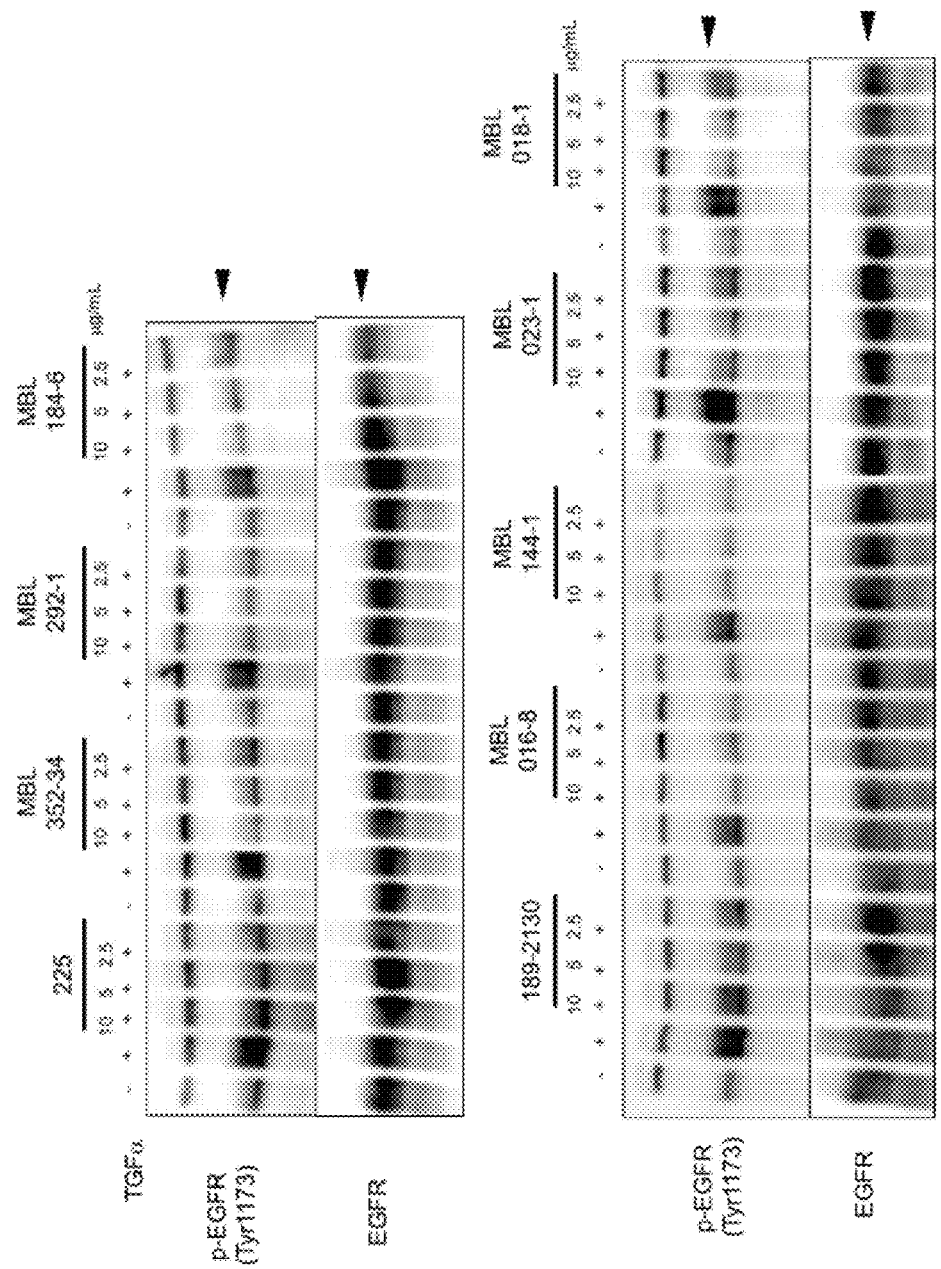

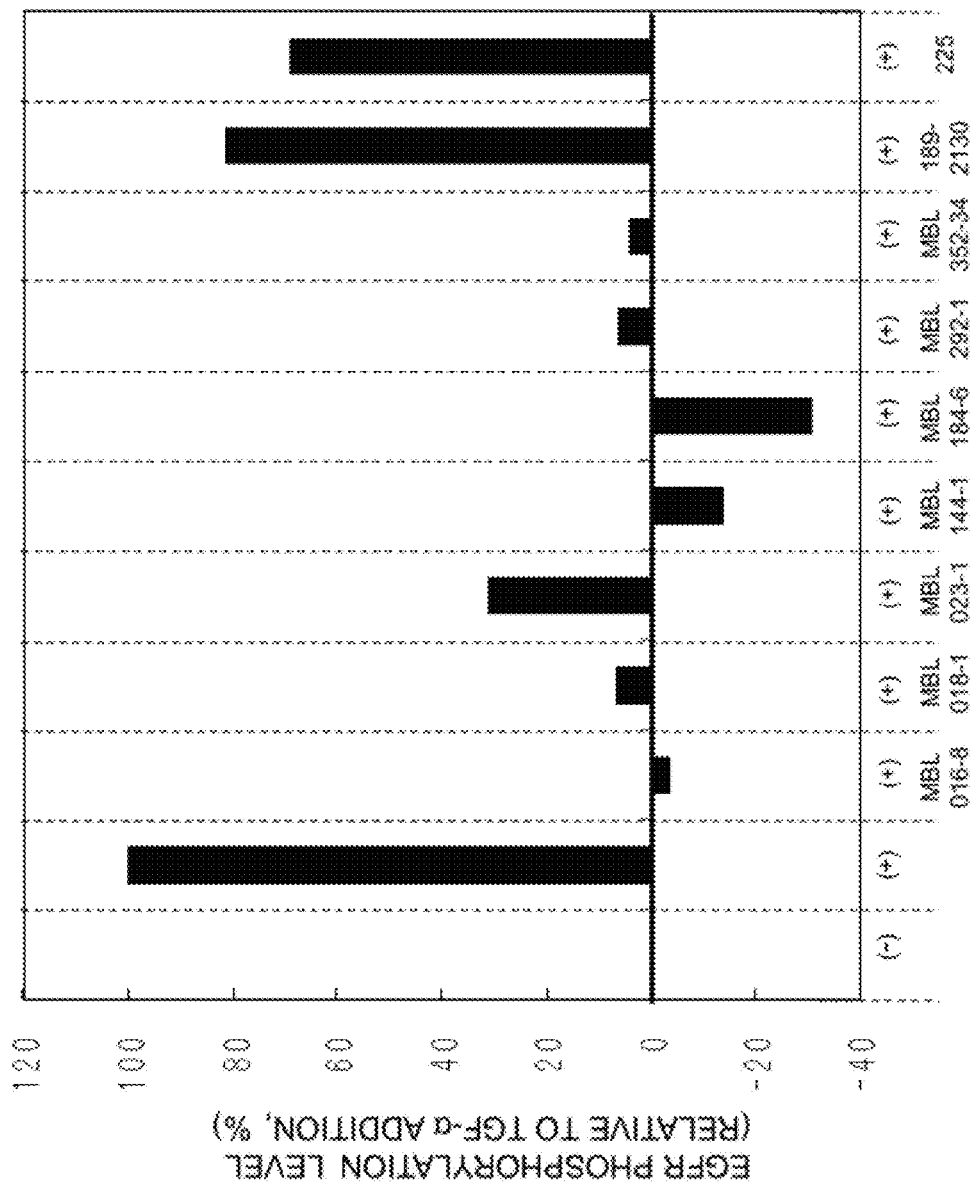

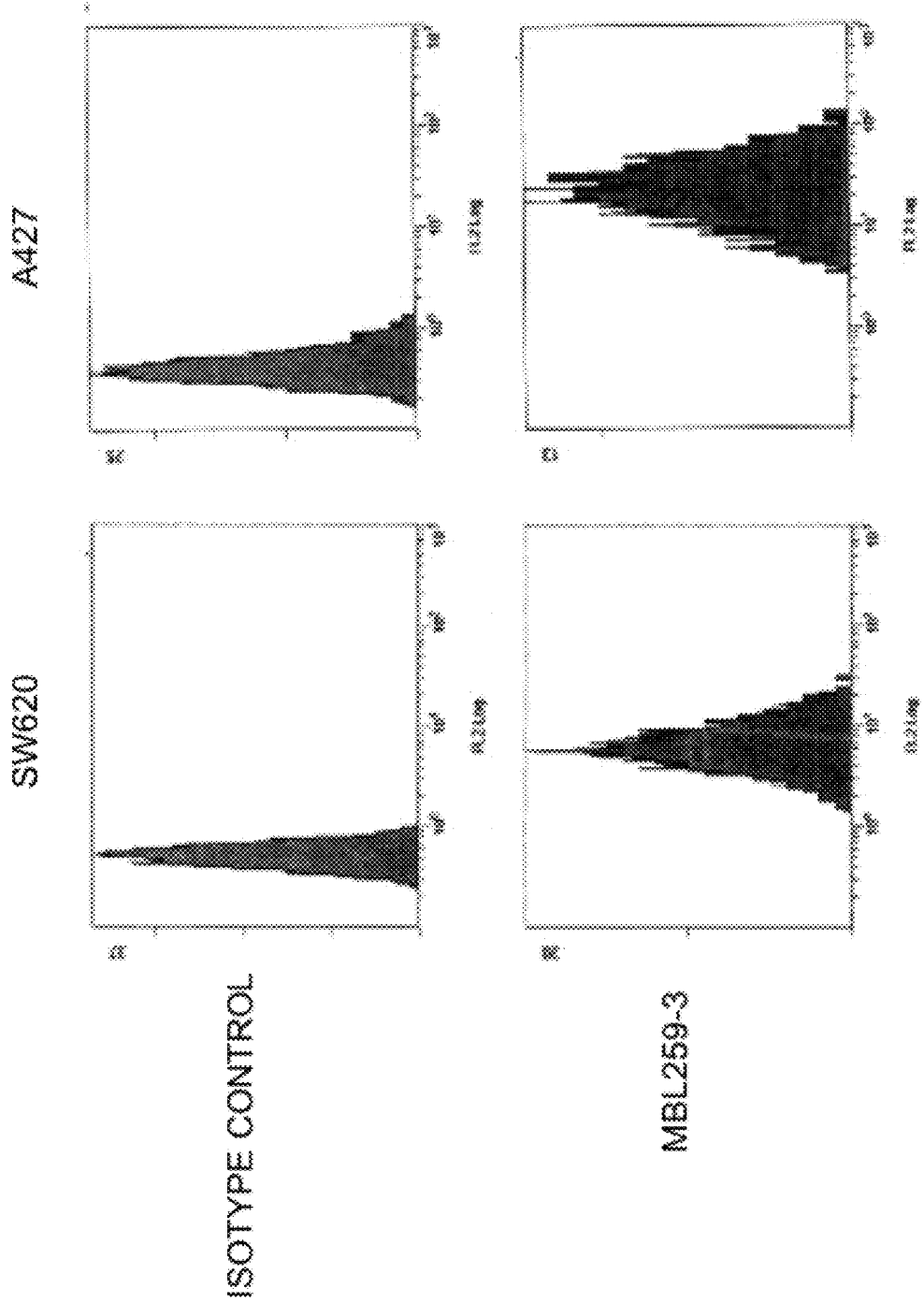

Fig. 15

H CHAIN

```
GTGCAGCTTCAGGAGTCGGGACCTGGCCTGGTGAAACCTTCTCAGTCTCTGTCCCTCACC
 V  Q  L  Q  E  S  G  P  G  L  V  K  P  S  Q  S  L  S  L  T
                                    CDR1
TGCACTGTCACTGGCTACTCAATCACC AGTGATTATGCCTGGAAC TGGATCCGGCAGTTT
 C  T  V  T  G  Y  S  I  T  S  D  Y  A  W  N   W  I  R  Q  F
                                    CDR2
CCAGGAAACAAACTGGAGTGGATGGGC TACATAAGCTACAGTGGTAGCACTAGCTACAAC
 P  G  N  K  L  E  W  M  G  Y  I  S  Y  S  G  S  T  S  Y  N

CCATCTCTCAAAAGT CGAATCTCTATCACTCGAGACACATCCAAGAACCAGTTCTTCCTG
 P  S  L  K  S  R  I  S  I  T  R  D  T  S  K  N  Q  F  F  L
                                                       CDR3
CAGTTGAATTCTGTGACTACTGAGGACACAGCCACATATTATTGTGCAAGA GGGGGGATT
 Q  L  N  S  V  T  T  E  D  T  A  T  Y  Y  C  A  R  G  G  I

ACGAGGTTTGCTTAC TGGGGCCAAGGGACTCTGGTCACTGTCTCTGCA
 T  R  F  A  Y  W  G  Q  G  T  L  V  T  V  S  A
```

L CHAIN

```
GATATCCAGATGACACAGACTACATCCTCCCTGTCTGCCTCTCTGGGAGACAGACTCACC
 D  I  Q  M  T  Q  T  T  S  S  L  S  A  S  L  G  D  R  L  T
               CDR1
ATCAGTTGC AGGGCAAGTCAGGACATTCGCAATTATTTAAAC TGGTATCAGCAGAAACCA
 I  S  C  R  A  S  Q  D  I  R  N  Y  L  N   W  Y  Q  Q  K  P
                                CDR2
GATGGAACTGTTAAACTCCTGATCTAC TACACATCAAGATTACACTCA GGAGTCCCATCA
 D  G  T  V  K  L  L  I  Y  Y  T  S  R  L  H  S  G  V  P  S

AGGTTCAGTGGCAGTGGGTCTGGAACAGATTATTCTCTCACCATTAGCAACCTGGAGCAA
 R  F  S  G  S  G  S  G  T  D  Y  S  L  T  I  S  N  L  E  Q
                                CDR3
GAAGATATTGCCACTTACTTTTGC CAACAGGGTAATACGCTTCCG TGGACGTTCGGTGGA
 E  D  I  A  T  Y  F  C  Q  Q  G  N  T  L  P  W  T  F  G  G

GGCACCAAGCTGGAAATCAAA
 G  T  K  L  E  I  K
```

Fig. 16

H CHAIN

```
GTTCAGCTGCAGCAGTCTGGGGCTGAGCTTGTGAGGCCAGGGGCCTCAGTCAAGTTGTCC
 V  Q  L  Q  Q  S  G  A  E  L  V  R  P  G  A  S  V  K  L  S
                                    CDR1
TGCACAGCTTCTGGCTTTAACATTAAAGACGACTATATGTACTGGGTGAAGCAGAGGCCT
 C  T  A  S  G  F  N  I  K |D  D  Y  M  Y| W  V  K  Q  R  P
                            CDR2
GAACAGGGCCTGGAGTGGATTGGAAGGATTGATCCTGCGAATGGTAATACTAAATATGCC
 E  Q  G  L  E  W  I  G |R  I  D  P  A  N  G  N  T  K  Y  A

CCGAAGTTCCAGGACAAGGCCACTATAACTGCAGACACATCCTCCAACACAGCCTACCTG
  P  K  F  Q  D| K  A  T  I  T  A  D  T  S  S  N  T  A  Y  L
                                                      CDR3
CATCTCAGCAGCCTGACATCTGAGGACACTGCCGTCTTTTACTGTGCTTAT AGACGGGCT
 H  L  S  S  L  T  S  E  D  T  A  V  F  Y  C  A  Y |R  R  A

TACTGGGGCCAAGGGACTCTGGTCACTGTCTCTGCA
 Y| W  G  Q  G  T  L  V  T  V  S  A
```

L CHAIN

```
GACATCCAGATGACACAGTCTCCATCCTCACTGTCTGCATCTCTGGGAGGCAAAGTCACC
 D  I  Q  M  T  Q  S  P  S  S  L  S  A  S  L  G  G  K  V  T
        CDR1
ATCACTTGCAAGGCAAGCCAAGACATTAACAAGTATATAGCTTGGTACCAACACAAGCCT
 I  T  C |K  A  S  Q  D  I  N  K  Y  I  A| W  Y  Q  H  K  P
                                  CDR2
GGAAAAGGTCCTAGGCTGTTTATACATTACACATCAAACTACAGCCAGGCATCCCATCA
 G  K  G  P  R  L  F  I  H |Y  T  S  K  L  Q  P| G  I  P  S

AGGTTCAGTGGAAGTGGGTCTGGGAGAGATTATTCCTTCAGCATCAGCAACCTGGAGCCT
 R  F  S  G  S  G  S  G  R  D  Y  S  F  S  I  S  N  L  E  P
                            CDR3
GAAGATATTGCAACTTATTATTGTCTACAGTATGATAATCTTCTGTATACGTTCGGAGGG
 E  D  I  A  T  Y  Y  C |L  Q  Y  D  N  L  L| Y  T  F  G  G

GGGACCAAGCTGGAAATAAAA
 G  T  K  L  E  I  K
```

Fig. 17

H CHAIN

```
GAGGTTCAGCTCCAGCAGTCTGGGACTGTGCTGACAAGGCCTGGGGCTTCAGTGAAGATG
 E  V  Q  L  Q  Q  S  G  T  V  L  T  R  P  G  A  S  V  K  M
                                          CDR1
TCCTGCAAGGCTTCTGGCTACACCTTTACC AACTTCTGGATCCAC TGGGTCAAACAGAGG
 S  C  K  A  S  G  Y  T  F  T  N  F  W  I  H  W  V  K  Q  R
                                  CDR2
CCTGGACAGGGTCTGGACTGGATTGGC GCTATTTATCCTGGAAATACTAATACTGACTAC
 P  G  Q  G  L  D  W  I  G  A  I  Y  P  G  N  T  N  T  D  Y

AACCAGAAGTTCCAGGGC AAGGCCAAACTGACTGCTGTCTCATCTGCCAGCACTGCCTAC
 N  Q  K  F  Q  G  K  A  K  L  T  A  V  S  S  A  S  T  A  Y

CDR3
ATGGAGCTCAGCAGCCTGACAAATGAGGACTCTGCGGTCTATTACTGTACAAGG GGGGGG
 M  E  L  S  S  L  T  N  E  D  S  A  V  Y  Y  C  T  R  G  G

GCTATGGACTAC TGGGGTCAAGGAACCTCAGTCACCGTCTCCTCA
 A  M  D  Y  W  G  Q  G  T  S  V  T  V  S  S
```

L CHAIN

```
ATTGTGATGACCCAGACTCCCAAACTCCTGCCTGTATCAGCAGGAGACAGGGTTACCATG
 I  V  M  T  Q  T  P  K  L  L  P  V  S  A  G  D  R  V  T  M
     CDR1
ACCTGC AAGGCCAGTCAGAGTGTGGATAATAGTGTAGCC TGGTACCAACAGAAGCCAGGA
 T  C  K  A  S  Q  S  V  D  N  S  V  A  W  Y  Q  Q  K  P  G
                               CDR2
CAGTCTCCTAAATTGCTGATATTC TATGCATCCAATCACTACACT GGAGTCCCTGATCGC
 Q  S  P  K  L  L  I  F  Y  A  S  N  H  Y  T  G  V  P  D  R

TTCACTGCCAGTGGATCTGGGACAGATTTCACTTTCACCATCAGCAGTGTGCAGGTTGAA
 F  T  A  S  G  S  G  T  D  F  T  F  T  I  S  S  V  Q  V  E
                          CDR3
GACCTGGCAGTTTATTTCTGT CAGCAGCATTTTAGCTCTCCT CGGACGTTCGGTGGAGGC
 D  L  A  V  Y  F  C  Q  Q  H  F  S  S  P  R  T  F  G  G

ACCAAACTGGAAATCAGA
 T  K  L  E  I  R
```

Fig. 18

H CHAIN

```
GTGCAGCTTCAGGAGTCAGGACCTGGCCTGGCAAAACCTTCTCAGACTCTGTCCCTCACC
 V  Q  L  Q  E  S  G  P  G  L  A  K  P  S  Q  T  L  S  L  T
                                    CDR1
TGTTCTGTCACTGGCTACTCCATCACC|AGTGATTACTGGAAC|TGGATCCGGAAATTCCA
 C  S  V  T  G  Y  S  I  T | S  D  Y  W  N | W  I  R  K  F  P
                                CDR2
GGGAATAAACTTGAGTACATGGGG|TACATAAGCTACAGTGGTAGCACTTACTACAATCCA
 G  N  K  L  E  Y  M  G | Y  I  S  Y  S  G  S  T  Y  Y  N  P

|TCTCTCAAAAGT|CGAATCTCCATCACTCGAGACACATCCAAGAACCAGTATTACCTGCAG
| S  L  K  S |R  I  S  I  T  R  D  T  S  K  N  Q  Y  Y  L  Q
                                                    CDR3
TTGAATTCTGTGACTACTGAGGACACAGCCACATATTACTGTGCAAGA|TCCTACGATGGT
 L  N  S  V  T  T  E  D  T  A  T  Y  Y  C  A  R | S  Y  D  G

|ATCTGCTTTGACAAC|TGGGGCCAAGGCACCACTCTCACAGTCTCCTCA
| I  C  F  D  N | W  G  Q  G  T  T  L  T  V  S  S
```

L CHAIN

```
GACATCCTGATGACCCAGTCTCCAGCCACCCTGTCTGTGACTCCAGGAGAAACAGTCAGT
 D  I  L  M  T  Q  S  P  A  T  L  S  V  T  P  G  E  T  V  S
          CDR1
CTTTCCTGT|AGGGCCAGCCAGAATACTTACAAGAACCTACAC|TGGTATCAACAGAAATCA
 L  S  C | R  A  S  Q  N  T  Y  K  N  L  H | W  Y  Q  Q  K  S
                            CDR2
CATGGGACTCCAAAGCTTCTCATCAAG|TATGCATCTGCTCCCATCTCT|GGATCCCCTCC
 H  G  T  P  K  L  L  I  K | Y  A  S  A  P  I  S | G  I  P  S

AGGTTCACTGGCAGTGGATCAGGGACAGATTACACTCTCAGTATCAACAGTGTGAAGCCC
 R  F  T  G  S  G  S  G  T  D  Y  T  L  S  I  N  S  V  K  P
                            CDR3
GAAGATGAAGGAATATATTACTGT|CTTCAGGGTTACAGCATGCCG|TGGACGTTCGGTGGA
 E  D  E  G  I  Y  Y  C | L  Q  G  Y  S  M  P | W  T  F  G  G

GGCACCAAGCTGGAAATCAAA
 G  T  K  L  E  I  K
```

Fig. 19

H CHAIN

```
GAGGTTCAGCTGCAGCAGTCTGGGGCTGAACTTGTGAGGCCAGGGGCCTCAGTCAAGTTG
 E  V  Q  L  Q  Q  S  G  A  E  L  V  R  P  G  A  S  V  K  L
                                           CDR1
TCCTGCACAGTTTCTGGCTTTAACATTAAAGACGACTATATGCACTGGGTGAAGCAGAGG
 S  C  T  V  S  G  F  N  I  K |D  D  Y  M  H| W  V  K  Q  R
                                   CDR2
CCTGAACAGGGCCTGGAGTGGATTGGAAGGATTGATCCTGCGAATGGTCATACTAAATAT
 P  E  Q  G  L  E  W  I  G |R  I  D  P  A  N  G  H  T  K  Y
 GCCCCGAAGTTCCAGGAC|AAGGCCACTATAACTGCAGACACATCCTCCAACACAGCCTAC
 A  P  K  F  Q  D| K  A  I  T  A  D  T  S  S  N  T  A  Y
                                                      CDR3
CTGCAGTTCAGCAGCCTGACATCTGAGGACACTGCCGTCTATTACTGTACAAGA|ATGGGG
 L  Q  F  S  S  L  T  S  E  D  T  A  V  Y  Y  C  T  R |M  G
 TTACGACGAGGCTAC|TGGGGCCAAGGCACCACTCTCACAGTCTCCTCA
 L  R  R  G  Y| W  G  Q  G  T  T  L  T  V  S  S
```

L CHAIN

```
ATCCAGATGACACAATCTTCATCCTCCTTGTCTGTATCTCTAGGAGACAGAGTCACCATT
 I  Q  M  T  Q  S  S  S  S  L  S  V  S  L  G  D  R  V  T  I
        CDR1
ACTTGC|AAGGCAAGTGAACACATTAATAGTTGGTTAGCC|TGGTATCAGCAAAAACCAGGA
 T  C |K  A  S  E  H  I  N  S  W  L  A| W  Y  Q  Q  K  P  G
                         CDR2
AATGCTCCTAGGCTCTTAATATCT|GGTGCAACCAATTTGGAAACT|GGGGTTCCTTCAAGA
 N  A  P  R  L  L  I  S |G  A  T  N  L  E  T| G  V  P  S  R
TTCAGTGGCAGTGCATCTGGAAAGGATTACACTCTCAACATTACTAGTCTTCAGACTGAA
 F  S  G  S  A  S  G  K  D  Y  T  L  N  I  T  S  L  Q  T  E
                      CDR3
GATGTTGCTACTTATTACTG|TCAACAGTATTGGGGTACTCC|GTGGACGTTCGGTGGAGGC
 D  V  A  T  Y  Y  C |Q  Q  Y  W  G  T  P| W  T  F  G  G
ACCAAACTGGAAATCAAA
 T  K  L  E  I  K
```

Fig. 20

H CHAIN

```
GTTCAGCTGCAGCAGTCTGGGGCTGAGCTTGTGAGGCCAGGGGCCTCAGTCAAGTTGTCC
 V  Q  L  Q  Q  S  G  A  E  L  V  R  P  G  A  S  V  K  L  S
                                        CDR1
TGCACAGCTTCTGACTTTAACATTAAAGACGACTATATGCAC TGGATGAAGCAGAGGCCT
 C  T  A  S  D  F  N  I  K |D  D  Y  M  H| W  M  K  Q  R  P
                                    CDR2
GAACAGGGCCTGGAGTGGATTGGA AGGATTGATCCTGCGAATGGTAATACTAAATATGCC
 E  Q  G  L  E  W  I  G |R  I  D  P  A  N  G  N  T  K  Y  A

CCGAAGTTCCAGGAC AAGGCCACTATGACTGCAGACACATCCTCCAACACAGCCTACTTG
 P  K  F  Q  D| K  A  T  M  T  A  D  T  S  S  N  T  A  Y  L
                                                    CDR3
CAATTCAGCAGCCTGACATCTGAGGACACTGCCGTCTATTACTGTGCTACT TCTTGGGGC
 Q  F  S  S  L  T  S  E  D  T  A  V  Y  Y  C  A  T |S  W  G

TTTCCTTAT TGGGGCCAAGGGACTCTGGTCACTGTCTCTGCA
 F  P  Y| W  G  Q  G  T  L  V  T  V  S  A
```

L CHAIN

```
GATATTGTGATGACTCAGGCTGCACCCTCTGTACCTGTCACTCCTGGAGAGTCAGTATCC
 D  I  V  M  T  Q  A  A  P  S  V  P  V  T  P  G  E  S  V  S
              CDR1
ATCTCCTGC AGGTCTAGTAAGAGTCTCCTGCATAGAAATGGCAACACTTATTTGTAT TGG
 I  S  C |R  S  S  K  S  L  L  H  R  N  G  N  T  Y  L  Y| W
                                                CDR2
TTCCTGCAGAGGCCAGGCCAGTCTCCTCAGCTCCTGATATAT CGGATGTCCAACCTTGCC
 F  L  Q  R  P  G  Q  S  P  Q  L  L  I  Y |R  M  S  N  L  A

TCA GGAGTCCCAGACAGGTTCAGTGGCAGTGGGTCAGGAACTGCTTTCACACTGAGAATC
 S| G  V  P  D  R  F  S  G  S  G  S  G  T  A  F  T  L  R  I
                                            CDR3
AGTAGAGTGGAGGCTGAGGATGTGGGTGTTTATTACTGT TTGCAACATCTAGAATATCCT
 S  R  V  E  A  E  D  V  G  V  Y  Y  C |L  Q  H  L  E  Y  P

TATACGTTCGGATCGGGGACCAAACTGGAAATAAAA
 Y  T  F  G  S  G  T  K  L  E  I  K
```

Fig. 21

H CHAIN

```
GTTCAGCTGCAGCAGTCTGGGGCTGAGCTTGTGAGGCCAGGGGCCTCAGTCAAGTTGTCC
 V  Q  L  Q  Q  S  G  A  E  L  V  R  P  G  A  S  V  K  L  S
                                   CDR1
TGCACAGCTTCTGGCTTTAACATTAAAGACGACTATATGCACTGGATGAAGCAGAGGCCT
 C  T  A  S  G  F  N  I  K [ D  D  Y  M  H] W  M  K  Q  R  P
                           CDR2
GAACAGGGCCTGGAGTGGATTGGAAGGATTGATCCTGCGAATGGTAATACTAAATATGCC
 E  Q  G  L  E  W  I  G [ R  I  D  P  A  N  G  N  T  K  Y  A

CCGAAGTTCCAGGACAAGGCCACTATAACTGCAGACACATCCTCCAACACAGCCTACCTG
  P  K  F  Q  D] K  A  T  I  T  A  D  T  S  S  N  T  A  Y  L
                                                       CDR3
CAGCTCAGCAGCCTGACATCTGAGGACACTGCCGTCTATTACTGTTCTAGAATGGGGTTA
 Q  L  S  S  L  T  S  E  D  T  A  V  Y  Y  C  S  R [ M  G  L

CTTCGAGGCTACTGGGGCCAAGGCACCACTCTCACAGTCTCCTCA
 L  R  G  Y] W  G  Q  G  T  T  L  T  V  S  S
```

L CHAIN

```
ATCCAGATGACACAATCTTCATCCTCCTTGTCTGTATCTCTAGGAGACAGAGTCACCATT
 I  Q  M  T  Q  S  S  S  S  L  S  V  S  L  G  D  R  V  T  I
       CDR1
ACTTGC AAGGCAAGTGTACACATTAATAGTTGGTTAGCC TGGTATCAGCAAAAACCAGGA
 T  C [K  A  S  V  H  I  N  S  W  L  A] W  Y  Q  Q  K  P  G
                              CDR2
AATGCTCCTAGGCTCTTAATATCTGGTGCAACCAATTTGAAAACTGGGGTTCCTTCAAGA
 N  A  P  R  L  L  I  S [G  A  T  N  L  K  T] G  V  P  S  R

TTCAGTGGCAGTGCATCTGGAAAGGATTACACTCTCAGCATTACTAGTCTTCAGACTGAA
 F  S  G  S  A  S  G  K  D  Y  T  L  S  I  T  S  L  Q  T  E
                            CDR3
GATGTTGCTACTTATTACTGTCAACAGTATTGGGATACTCCGTGGACGTTCGGTGGAGGC
 D  V  A  T  Y  Y  C [Q  Q  Y  W  D  T  P] W  T  F  G  G

ACCAAGCTGGAAATCAAA
 T  K  L  E  I  K
```

Fig. 22

H CHAIN

```
GTTCAGCTGCAGCAGTCTGGGGCTGAGCTTGTGAGGCCAGGGGCCTCAGTCAAGTTGTCC
 V  Q  L  Q  Q  S  G  A  E  L  V  R  P  G  A  S  V  K  L  S
                                              CDR1
TGCACAGCTTCTGGCTTTAACATTAAAGACGACTATATGCACTGGGTGAAGCAGAGGCCT
 C  T  A  S  G  F  N  I  K |D  D  Y  M  H| W  V  K  Q  R  P
                             CDR2
GAACAGGGCCTGGAGTGGATTGGAAGGATTGATCCTGCGAATGGTCATACTAAATATGCC
 E  Q  G  L  E  W  I  G |R  I  D  P  A  N  G  H  T  K  Y  A
CCGAAGTTCCAGGACAAGGCCACTATAACTGCAGACACATCCTCCAACACAGCCTACCTG
 P  K  F  Q  D| K  A  T  I  T  A  D  T  S  S  N  T  A  Y  L
                                                     CDR3
CAGTTCAGCAGCCTGACATCTGAGGACACTGCCGTCTATTACTGTACAAGAATGGGATTA
 Q  F  S  S  L  T  S  E  D  T  A  V  Y  Y  C  T  R |M  G  L
CGACGAGGCTAC TGGGGCCAAGGCACCACTCTCACAGTCTCCTCA
 R  R  G  Y| W  G  Q  G  T  T  L  T  V  S  S
```

L CHAIN

```
ATCCAGATGACACAATCTTCATCCTCCTTGTCTGTATCTCTAGGAGACAGAGTCACCATT
 I  Q  M  T  Q  S  S  S  S  L  S  V  S  L  G  D  R  V  T  I
        CDR1
ACTTGCAAGGCAAGTGAACACATTAATAGTTGGTTAGCCTGGTATCAGCAAAAACCAGGA
 T  C |K  A  S  E  H  I  N  S  W  L  A| W  Y  Q  Q  K  P  G
                         CDR2
AATGCTCCTAGGCTCTTAATATCTGGTGCAACCAATTTGAAAACTGGGGTTCCTTCAAGA
 N  A  P  R  L  L  I  S |G  A  T  N  L  K  T| G  V  P  S  R
TTCAGTGGCAGTGCATCTGGAAAGGATTACACTCTCAGCATTACTAGTCTTCAGACTGAA
 F  S  G  S  A  S  G  K  D  Y  T  L  S  I  T  S  L  Q  T  E
                          CDR3
GATGTTGCTACTTATTACTGTCAACAGTATTGGGGTACTCCGTGGACGTTCGGTGGAGGC
 D  V  A  T  Y  Y  C |Q  Q  Y  W  G  T  P| W  T  F  G  G
ACCAAGCTGGAAATCAAA
 T  K  L  E  I  K
```

ANTIBODY BEING CAPABLE OF BINDING TO TRANSFORMING GROWTH FACTOR ALPHA AND HAVING GROWTH-SUPPRESSING ACTIVITY ON CANCERS HAVING RAS GENE MUTATION

TECHNICAL FIELD

The present invention relates to: a monoclonal antibody being capable of binding to transforming growth factor alpha (hereinafter referred to as "TGF-α") and having an effect of suppressing in vivo growth of cancer cells having a mutated Ras protein; and an anti-cancer agent comprising the antibody.

BACKGROUND ART

In the beginning of 1980s, the group of Sporn, Roberts, et al. isolated and purified TGF-α from a culture supernatant of murine sarcoma virus-transformed mouse 3T3 cells as one of two factors necessary to induce colony formation of normal rat kidney fibroblast cells (NRK cells) in soft agar (NPLs 1 to 6).

TGF-α is biosynthesized as a precursor polypeptide consisting of 160 amino acids. After glycosylated and palmitoylated inside a cell, TGF-α is expressed on the surface of the cell membrane as a type I transmembrane protein (transmembrane TGF-α) (NPL 7). Then, the extracellular domain is cleaved by a metalloprotease such as TACE/ADAM17. Hence, a single polypeptide consisting of 50 amino acids from 40th to 89th amino acids (approximately 6 kDa) is released as secreted TGF-α (NPLs 8 to 10). Secreted TGF-α has a characteristic structure in which disulfide bonds are formed at three sites by six cysteine residues (NPLs 11 to 13). This structure was first discovered in epidermal growth factor (EGF), and thereafter is called an EGF-like domain. There are 13 types of proteins having an EGF-like domain in total, including, other than TGF-α and EGF, amphiregulin, HB-EGF, β-cellulin, epiregulin, epigen, neuregulin-1, neuregulin-2, neuregulin-3, neuregulin-4, neuregulin-5, and neuregulin-6 (hereinafter, neuregulin-1 to -6 are referred to as neuregulins). These are collectively called EGF family molecules (NPLs 10, 14). All of the EGF family molecules are biosynthesized as the type I membrane proteins like TGF-α. Releasable extracellular domains are formed by shedding with a protease (NPL 10). There is a high degree of amino acid homology among species, and the EGF-like domain structure is also preserved. For example, human TGF-α has an amino acid homology of 92% with mouse TGF-α, and human TGF-α works in mice and rats (NPL 15).

EGF family molecules act as ligands that directly bind to the receptor tyrosine kinase EGF receptor (EGFR) family (also known as ErbB family). Currently, four types are identified in the EGFR family based on the structural similarity, and respectively called EGFR (ErbB1), HER2 (ErbB2), HER3 (ErbB3), and HER4 (ErbB4) (NPLs 14, 16). Among 13 types of existing EGF family molecules, TGF-α, EGF, amphiregulin, β-cellulin, epiregulin, and the like are known as ligands which bind to EGFR. Neuregulins bind to HER3, while neuregulins, β-cellulin, and HB-EGF bind to HER4. HER2 has no ligand-binding site (NPLs 14, 16).

When an EGF family molecule binds to a receptor EGFR family molecule, the receptor forms a dimer, and phosphorylation of tyrosine residues is induced by tyrosine kinases located in the intracellular domain (NPL 16). Subsequent to this, various proteins in the cell are activated like a cascade. As typical examples of such a cascade pathway, the Ras/Raf/MAPK pathway, the PI3K/Akt/mTOR pathway, and the JAK-STAT pathway are known. The Ras/Raf/MAPK pathway is mainly associated with cell proliferation and survival, PI3K/Akt/mTOR pathway is associated with cell growth, anti-apoptosis, cell infiltration, cell migration, and so forth (NPL 17).

When secreted TGF-α is added to normal rat fibroblast cells Rat-1 in soft agar, the cell form of Rat-1 is changed to a transformed cell-like form, and colonies are formed in the agar (NPL 15). Moreover, CHO cells having a TGF-α gene introduced thereinto also become transformant-like cells, and readily form a tumor when transplanted into a nude mouse (NPL 9). In this event, EGFR on the surface of the CHO cells is significantly phosphorylated. Accordingly, it is understood that TGF-α secreted by CHO induces cell proliferation in an autocrine manner. As another physiological function of TGF-α, an action as a potent angiogenesis-inducing factor is known. It is believed that TGF-α acting on EGFR expressed in vascular endothelial cells induces migration and proliferation of the vascular endothelial cells (NPLs 18 to 21).

The distribution of TGF-α in the body of a healthy subject is characterized by the expression in mucosal epithelial cells such as in the respiratory epithelium and mucosal epithelium of the large intestine (NPLs 22 to 24). This expression pattern resembles that of EGFR. Meanwhile, as to cancers, it is well known that TGF-α is over-expressed mainly in solid cancers (NPLs 22, 23). Enhanced expression of TGF-α at mRNA and protein levels has been observed in various carcinomas such as head and neck cancers, lung cancer, breast cancer, stomach cancer, colorectal cancer, kidney cancer, liver cancer, ovarian cancer, and melanoma. Overexpression of the receptor EGFR has also been observed in various cancer tissues. It has been reported amounts of TGF-α and EGFR expressed are positively correlated particularly in non-small cell lung cancer, head and neck squamous cell carcinomas, and kidney cancer (NPLs 25 to 29). Developed at a site nearby a solid cancer is a tissue called an interstitial tissue which is constituted of a stroma (mainly fibroblast cells), serving as the scaffold for cancer cells, and a blood vessel for transporting nutrients. The result of immunohistostaining of cancer tissues using an anti-TGF-α antibody has revealed that TGF-α exists not only in a cancer site but also in an interstitial tissue (NPLs 25, 29). From these, it is believed that TGF-α not only induces the proliferation of cancer cells in an autocrine manner, but also contributes to the malignant transformation of the cancer by functioning as a growth factor of the interstitial tissue supporting the cancer growth (NPLs 18 to 21, 30).

As described above, there is no doubt that EGF family molecules including TGF-α and the receptor EGFR are involved in proliferation of cancers. Accordingly, as a matter of course, it is expected that cancer cell proliferation can be controlled by targeting TGF-α and EGFR (NPLs 16, 17, 31).

Research for a monoclonal antibody targeting EGFR in cancer treatment has been started since the beginning of 1980s (NPLs 32 to 34). Cetuximab (trade name: Erbitux) was developed as a monoclonal antibody which has an activity of inhibiting tyrosine phosphorylation and dimerization of EGFR by binding thereto competitively with the ligand EGF (NPLs 35, 36). Cetuximab was confirmed to suppress proliferation of cultured cancer cells such as A431 cells, and to demonstrate an anti-tumor effect in a cancer-bearing mouse model, also. In 1990, clinical trial had been started targeting patients with squamous cell lung carcinoma. In a randomized controlled trial conducted in 2001 and 2002, the effect on colorectal cancer was proved. In 2003, cetuximab was approved for the first time in Switzerland as a therapeutic agent against metastatic colorectal cancer. FDA also approved cetuximab in 2004 as a therapeutic agent against metastatic colorectal cancer expressing EGFR, and additionally approved in 2006 as a therapeutic agent against head and neck cancers expressing EGFR. In Japan, the Ministry of Health, Labour and Welfare approved the manufacturing and sales of cetuximab in 2008 as a therapeutic agent against EGFR-positive, advanced and recurrent colon and rectal cancers uncurable by resection (NPL 37). Panitumumab (trade name: Vectibix, Amgen Inc.) is known as an anti-EGFR monoclonal antibody which suppresses cancer proliferation in a similar manner by binding to EGFR(NPL 38). In Europe and the United States, panitumumab is used as a therapeutic agent against EGFR-positive, advanced and recurrent colorectal cancers similarly to cetuximab. Both of the anti-EGFR blocking antibodies improve the overall survival time and progression-free survival time of colorectal cancer patients uncurable by chemotherapy, and may preserve the quality of life. Thus, it is desired to broaden the application to other EGFR-positive cancers (NPLs 31, 35, 39).

However, on the other hand, colorectal cancer becomes cetuximab resistance at a high frequency, and progress of colorectal cancer has been observed in 50% or more of patients (NPLs 40, 41). It is pointed out that K-Ras gene mutation is involved in this cetuximab resistance. In other words, if there is a mutation in the gene of K-Ras located downstream of EGFR, cells are activated and the cancer keeps proliferating regardless of whether cetuximab or panitumumab blocks EGFR or not (NPL 42).

In 1960s, K-Ras and H-Ras were isolated as oncogenes from Kirusten rat and Harbey sarcoma viruses, respectively. Then, activated H-Ras was isolated from a human bladder cancer cell line, activated K-Ras was isolated from a human lung cancer cell line, and activated N-Ras was isolated from a neuroblastoma (NPLs 43, 44). The homology of gene products from these three types of Ras gene is as high as approximately 85%. A Ras gene product in normal cells is one kind of low-molecular-weight G protein having a GTPase activity, and plays a role in progress of cell proliferation. If a point mutation occurs in the Ras gene, a missense mutation may occur in an amino acid to be encoded, lowering the original GTPase activity in some cases. An association is suggested between tumorigenesis and a point mutation, particularly, at the glycine residue of codon 12 or 13. Mutations at codon 12 or 13 have been observed in approximately 40% of colorectal cancer patients (NPL 40). It is believed that in order to maintain the active state of the mutated Ras protein to which GTP binds, signals are constantly transferred downstream, causing abnormal cell proliferation and tumorigenesis (NPL 45). In this event, various EGF family molecules including TGF-α are over-expressed. This presumably gives an impetus to cancer cell proliferation, and enhances cancer enlargement (NPL 46).

When there is a K-Ras gene mutation, no effect is expected even from the use of cetuximab or panitumumab, and only a risk of the side effect remains. For this reason, the use of these therapeutic drugs is restricted in Europe under such a condition that the drugs are used only for a patient having no K-Ras gene mutation. In Japan also, it is recommended that when cetuximab is used, the target is a patient having normal K-Ras gene who is expected to respond. As other EGFR inhibitors, gefitinib (trade name: Iressa) and erlotinib (trade name: Tarceva) are known, which are low molecular weight drug for inhibiting the action of tyrosine kinases present in the intracellular domain. However, there has been reported that the outcome of these therapeutic drugs is also unsatisfactory to a patient having a K-Ras mutation (NPLs 39, 47, 48).

Meanwhile, as long as we know, there is no report that a monoclonal antibody targeting TGF-α located upstream of EGFR inhibits proliferation of cancer cells derived from an actual cancer patient or controls tumor formation in a cancer-bearing model mouse into which human cancer cells are transplanted.

Nevertheless, there is a case in which a monoclonal antibody against TGF-α was used to control colony formation of cultured cells seeded in soft agar. In 1986, Rosenthal et al. conducted the following experiment using a monoclonal antibody TGF-α1 against human TGF-α. Although normal rat fibroblast cells Rat-1 hardly form colonies in soft agar, colony formation is readily induced by addition of human TGF-α. Moreover, clone 16 and clone 42 of a Rat-1 cell line established by forcibly introducing a human TGF-α gene thereinto also acquire colony-forming ability. The anti-TGF-α antibody TGF-α1 added to this culture system inhibited the colony formation. On the other hand, Rat-1 into which an activated Ras gene was introduced acquired colony-forming ability. However, TGF-α1 of the anti-TGF-α antibody added to this culture system was not able to inhibit the colony formation (NPL 15).

A similar experiment was conducted by Ciardiello et al. in 1990 (NPL 49). A TGF-α gene was introduced into normal mammary epithelial cells MCF10A to establish TGF-α-over-expressing cell lines MCF10A TGF-α C13 (hereinafter referred to as C13) and MCF10A TGF-α C14 (hereinafter referred to as C14). MCF10A cells of the parental line hardly form colonies in soft agar, while C13 and C14 have a high colony-forming ability. An anti-TGF-α monoclonal antibody Tab1 added to the culture system suppressed colony formation of C13 and C14 in an antibody concentration-dependent manner (the colony formation was inhibited by approximately 90% at an antibody concentration of 50 µg/mL or higher). In this experimental system, EGFR blocking antibody clone 528 achieved a colony formation inhibition 10 times or more as strong as Tab1 when evaluated by antibody concentration (the colony formation was inhibited by 90% or more at an antibody concentration of 5 µg/mL or higher).

Cell lines MCF10A Ha-ras C11 and MCF10A Ha-ras C12 established by introducing an activated Ras gene into MCF10A overexpress TGF-α and acquire a high colony-forming ability. These activated Ras-introduced cells show a strong resistance to the EGFR blocking antibody and the anti-TGF-α antibody in comparison with the above-described TGF-α introduced cells. EGFR blocking antibody 528 achieved only approximately 60 to 70% inhibition of the colony formation at an antibody concentration of 5 µg/mL. Meanwhile, the anti-TGF-α antibody Tab1 only achieved approximately 50% inhibition of the colony formation even at an antibody concentration of 50 µg/mL to 100 µg/mL.

In 1989, Sorvillo et al. of Oncogene Science, Inc. received a patent for multiple anti-TGF-α monoclonal antibodies (PLT 1). The patent specification describes the reaction specificity to TGF-α of clone 213-4.4, clone 134A-2B3, and clones 137 to 178, but does not provide data on these antibodies inhibiting TGF-α physiological function or inhibiting proliferation of TGF-α-expressing cells. In 1990, the same research group reported, in an article, anti-TGF-α antibodies described in the patent specification (NPL 50). This article illustrates that clones 189 to 2130 have an effect of inhibiting TGF-α binding to EGFR, but does not mention the influence, or the like, on proliferation of TGF-α-expressing cells and Ras mutated cancers.

As described above, as to controlling cancer cell proliferation, it has not been expected so far that an antibody against TGF-α present upstream of EGFR demonstrates a superior effect to an EGFR inhibitor including an EGFR blocking antibody. Further, it has been regarded as common sense so far that in cancer cells which are constantly activated on a downstream side of EGFR including Ras, it is still difficult to suppress the cancer cell proliferation even when EGFR located upstream and TGF-α located further upstream are blocked (NPLs 31, 46).

It has been reported that Ras gene mutations occur in quite a wide range of tumors. Among all the human cancers, 17 to 25% of patients on average have K-Ras gene mutations (NPL 51). Particularly, gene mutations were found in 35 to 40% of colorectal cancer patients, 35% of lung cancer patients, 55% of thyroid cancer patients, and 80 to 90% of pancreatic cancer patients (NPLs 52, 53). As described above, an activated Ras gene mutation causes a strong resistance shown to various EGFR inhibitors including cetuximab and panitumumab (NPLs 42, 54). A development of a therapeutic drug against Ras mutated cancers highly resistant to available drugs is an importantissue directly involved in improvement of living of human kind, and is also strongly expected by many cancer patients and doctors. However, there has been no effective means available for treatment of Ras mutated cancers up to now.

CITATION LIST

Patent Literature

[PTL 1] US Pat. No. 5190858

Non Patent Literatures

[NPL 1] Proc. Natl. Acad. Sci. USA (1978) 75, 4001-4005
[NPL 2] Proc. Natl. Acad. Sci. USA (1980) 77, 3494-3498
[NPL ] Nature (1982) 295, 417-419
[NPL 4] Cancer Res. (1982) 42, 4776-4778
[NPL 5] Proc. Natl. Acad. Sci. USA (1983) 80, 4684-4688
[NPL 6] Proc. Natl. Acad. Sci. USA (1983) 80, 6264-6268
[NPL 7] J. Cell Biol. (1994) 125, 903-916
[NPL 8] Proc. Natl. Acad. Sci. USA (1991) 88, 1726-1730
[NPL 9] EMBO J. (2003) 22, 1114-1124
[NPL 10] Cancer Sci. (2008) 99, 214-220
[NPL 11] Proc. Natl. Acad. Sci. USA (1986) 83, 8082-8086
[NPL 12] Biochem. (1993) 32, 7334-7353
[NPL 13] Cell (2002) 110, 763-773
[NPL 14] Exp. Cell Res. (2003) 284, 2-13
[NPL 15] Cell (1986) 46, 301-309
[NPL 16] N. Engl. J. Med. (2008), 1160-1174
[NPL 17] N. Engl. J. Med. (2008), 1367-1380
[NPL 18] Science (1986) 232, 1250-1253
[NPL 19] Breast J. (2000) 6, 171-177
[NPL 20] Int. J Oncol. (2000) 17, 453-60
[NPL 21] Neoplasia (2006) 8, 470-476
[NPL 22] Cell Prolif. (1993) 26, 449-60
[NPL 23] Cancer Res. (1987) 47, 707-712
[NPL 24] J. Histochem. Cytochem. (1999) 47, 949-957
[NPL 25] Cancer Res. (1993) 53, 2379-2385
[NPL 26] Am. J. Pathol. (1993) 142, 1155-1162
[NPL 27] Clin. Cancer Res. (1997) 3, 515-522
[NPL 28] Clin. Cancer Res. (2004) 10, 136-143
[NPL 29] Clin. Cancer Res. (2008) 14, 1303-1309
[NPL 30] Mol. Cancer Ther. (2007) 6, 2652-2663
[NPL 31] Nat. Rev. (2006) 7, 505-516
[NPL 32] Cancer Res. (1994) 54, 1695-1701
[NPL 33] J. Blol. Chem. (1994) 269, 27595-27602
[NPL 34] Clin Cancer Res. (2000) 6, 747-753
[NPL 35] Japan J Lung Cancer (2006) 46, 267-275
[NPL 36] CANCER CELL (2005) 7, 301-311
[NPL 37] Drug Interview Form (2008)
[NPL 38] Clin Colorectal Cancer (2005) 21- 23
[NPL 39] Oncology (2009) 77, 400-410
[NPL 40] N. Engl. J. Med. (2008), 1757-1765
[NPL 41] N. Engl. J. Med. (2009), 833-836
[NPL 42] J. Clin. Oncol. (2010) 26, 1254-1261
[NPL 43] Proc. Natl Acad. Sci. USA (1982) 79, 3637-3640
[NPL 44] Proc. Natl Acad. Sci. USA (1982) 79, 4848-4852
[NPL 45] Mol Cell Biol (1986) 6, 3291-3294
[NPL 46] Differentiation (2007) 75, 788-799
[NPL 47] J. Clin. Oncol. (2005) 23, 5900-5909
[NPL 48] Neoplasia (2009) 11, 1084-1092
[NPL 49] Cell Growth Differ (1990) 1, 407-420
[NPL 50] Oncogene (1990) 5, 377-386
[NPL 51] Biochim. Biophys. Acta. (2005) 1756 81-82
[NPL 52] Cancer Detect Prey. (2000) 24, 1-12
[NPL 53] Br. J. Cancer (2005) 92, 131-139
[NPL 54] J. Clin. Oncol. (2008) 26, 5668-5670

SUMMARY OF INVENTION

Technical Problem

The present invention has been made in view of the above-described circumstances. An object of the present invention is to provide an antibody having an excellent growth-suppressing effect on cancer cells having a mutated Ras gene. Another object of the present invention is to provide an anti-cancer agent comprising such an antibody as an active ingredient.

Solution to Problem

The present inventors have earnestly studied in order to achieve the above objects. As a result, the inventors have found out that among antibodies showing reactivity with wild type TGF-α, antibodies less reactive with G79A-substituted TGF-α have an excellent growth-suppressing effect on cancer cells having a mutated Ras gene. Further, the present inventors have also found out that most of these antibodies have an activity of inhibiting EGFR tyrosine phosphorylation and/or an induction-suppressing activity on vascular endothelial cells. These discoveries have led to the completion of the present invention.

Specifically, the present invention relates to an anti-TGF-α antibody having an excellent growth-suppressing effect on cancer cells having a mutated Ras gene, as well as a production method and use thereof. More specifically, the present invention provides the following inventions.

<1> An antibody against a human TGF-α and showing a growth-suppressing activity on cancer cells having a mutated Ras gene.

<2> An antibody less reactive with human TGF-α having mutated glycine at position 79 than with wild type human TGF-α.

<3> The antibody according to <2>, wherein the human TGF-α having mutated glycine at position 79 is G79A-substituted human TGF-α.

<4> The antibody according to any one of <1> to <3>, which has an activity of suppressing EGFR tyrosine phosphorylation.

<5> The antibody according to anyone of <1> to <4>, which has an activity of suppressing induction of vascular endothelial cells.

<6> The antibody according to <1>, which has any one of the following characteristics (a) to (h):

(a) comprising
a light chain variable region including amino acid sequences of SEQ ID NOs: 19 to 21 or the amino acid sequences in at least any one of which one or more amino acids are substituted, deleted, added and/or inserted, and a heavy chain variable region including amino acid sequences of SEQ ID NOs: 22 to 24 or the amino acid sequences in at least any one of which one or more amino acids are substituted, deleted, added and/or inserted;

(b) comprising a light chain variable region including amino acid sequences of SEQ ID NOs: 25 to 27 or the amino acid sequences in at least any one of which one or more amino acids are substituted, deleted, added and/or inserted, and a heavy chain variable region including amino acid sequences of SEQ ID NOs: 28 to 30 or the amino acid sequences in at least any one of which one or more amino acids are substituted, deleted, added and/or inserted;

(c) comprising a light chain variable region including amino acid sequences of SEQ ID NOs: 31 to 33 or the amino acid sequences in at least any one of which one or more amino acids are substituted, deleted, added and/or inserted, and a heavy chain variable region including amino acid sequences of SEQ ID NOs: 34 to 36 or the amino acid sequences in at least any one of which one or more amino acids are substituted, deleted, added and/or inserted;

(d) comprising a light chain variable region including amino acid sequences of SEQ ID NOs: 37 to 39 or the amino acid sequences in at least any one of which one or more amino acids are substituted, deleted, added and/or inserted, and a heavy chain variable region including amino acid sequences of SEQ ID NOs: 40 to 42 or the amino acid sequences in at least any one of which one or more amino acids are substituted, deleted, added and/or inserted;

(e) comprising a light chain variable region including amino acid sequences of SEQ ID NOs: 43 to 45 or the amino acid sequences in at least any one of which one or more amino acids are substituted, deleted, added and/or inserted, and a heavy chain variable region including amino acid sequences of SEQ ID NOs: 46 to 48 or the amino acid sequences in at least any one of which one or more amino acids are substituted, deleted, added and/or inserted;

(f) comprising a light chain variable region including amino acid sequences of SEQ ID NOs: 49 to 51 or the amino acid sequences in at least any one of which one or more amino acids are substituted, deleted, added and/or inserted, and a heavy chain variable region including amino acid sequences of SEQ ID NOs: 52 to 54 or the amino acid sequences in at least any one of which one or more amino acids are substituted, deleted, added and/or inserted;

(g) comprising a light chain variable region including amino acid sequences of SEQ ID NOs: 55 to 57 or the amino acid sequences in at least any one of which one or more amino acids are substituted, deleted, added and/or inserted, and a heavy chain variable region including amino acid sequences of SEQ ID NOs: 58 to 60 or the amino acid sequences in at least any one of which one or more amino acids are substituted, deleted, added and/or inserted; and (h) comprising a light chain variable region including amino acid sequences of SEQ ID NOs: 61 to 63 or the amino acid sequences in at least any one of which one or more amino acids are substituted, deleted, added and/or inserted, and a heavy chain variable region including amino acid sequences of SEQ ID NOs: 64 to 66 or the amino acid sequences in at least any one of which one or more amino acids are substituted, deleted, added and/or inserted.

<7> The antibody according to <1>, which has any one of the following characteristics (a) to (h):

(a) comprising a light chain variable region including an amino acid sequence of SEQ ID NO: 3 or the amino acid sequence in which one or more amino acids are substituted, deleted, added and/or inserted, and a heavy chain variable region including an amino acid sequence of SEQ ID NO: 4 or the amino acid sequence in which one or more amino acids are substituted, deleted, added and/or inserted;

(b) comprising a light chain variable region including an amino acid sequence of SEQ ID NO: 5 or the amino acid sequence in which one or more amino acids are substituted, deleted, added and/or inserted, and a heavy chain variable region including an amino acid sequence of SEQ ID NO: 6 or the amino acid sequence in which one or more amino acids are substituted, deleted, added and/or inserted;

(c) comprising a light chain variable region including an amino acid sequence of SEQ ID NO: 7 or the amino acid sequence in which one or more amino acids are substituted, deleted, added and/or inserted, and a heavy chain variable region including an amino acid sequence of SEQ ID NO: 8 or the amino acid sequence in which one or more amino acids are substituted, deleted, added and/or inserted;

(d) comprising a light chain variable region including an amino acid sequence of SEQ ID NO: 9 or the amino acid sequence in which one or more amino acids are substituted, deleted, added and/or inserted, and a heavy chain variable region including an amino acid sequence of SEQ ID NO: 10 or the amino acid sequence in which one or more amino acids are substituted, deleted, added and/or inserted;

(e) comprising a light chain variable region including an amino acid sequence of SEQ ID NO: 11 or the amino acid sequence in which one or more amino acids are substituted, deleted, added and/or inserted, and a heavy chain variable region including an amino acid sequence of SEQ ID NO: 12 or the amino acid sequence in which one or more amino acids are substituted, deleted, added and/or inserted;

(f) comprising
  a light chain variable region including an amino acid sequence of SEQ ID NO: 13 or the amino acid sequence in which one or more amino acids are substituted, deleted, added and/or inserted, and
  a heavy chain variable region including an amino acid sequence of SEQ ID NO: 14 or the amino acid sequence in which one or more amino acids are substituted, deleted, added and/or inserted;
(g) comprising
  a light chain variable region including an amino acid sequence of SEQ ID NO: 15 or the amino acid sequence in which one or more amino acids are substituted, deleted, added and/or inserted, and
  a heavy chain variable region including an amino acid sequence of SEQ ID NO: 16 or the amino acid sequence in which one or more amino acids are substituted, deleted, added and/or inserted; and
(h) comprising
  a light chain variable region including an amino acid sequence of SEQ ID NO: 17 or the amino acid sequence in which one or more amino acids are substituted, deleted, added and/or inserted, and
  a heavy chain variable region including an amino acid sequence of SEQ ID NO: 18 or the amino acid sequence in which one or more amino acids are substituted, deleted, added and/or inserted.
<8> An antibody produced by a hybridoma specified under an accession number of FERM ABP-11377.
<9> The antibody according to <1>, which binds to an epitope recognized by the antibody according to any one of <7> and <8>.
<10> A DNA encoding the antibody according to any one of <1> to <9>.
<11> A hybridoma producing the antibody according to any one of <1> to <9>, or comprising the DNA according to <10>.
<12> A method for producing the antibody according to <1>, comprising the steps of:
  (a) preparing antibodies capable of binding to human TGF-α; and
  (b) selecting, from the prepared antibodies, an antibody less reactive with human TGF-α having mutated glycine at position 79 than with wild type human TGF-α.
<13> The method according to <12>, wherein the human TGF-α having mutated glycine at position 79 is G79A-substituted human TGF-α.
<14> Human TGF-α having mutated glycine at position 79.
<15> G79A-substituted human TGF-α.
<16> An anti-cancer agent comprising the antibody according to any one of <1> to <9> as an active ingredient.
<17> The anti-cancer agent according to <16>, wherein the cancer is a cancer having a mutated Ras gene.
<18> A diagnostic agent for a cancer and comprising the antibody according to any one of <2>, <3>, <6> to <8> as an active ingredient.
<19> The diagnostic agent according to <18>, wherein the cancer is a cancer having a mutated Ras gene.

Advantageous Effects of Invention

The pre sent invention provides an anti-TGF-α antibody having an excellent growth-suppressing effect on cancer cells having a mutated Ras gene. Particularly, anti-TGF-α antibodies less reactive with human TGF-α having mutated glycine at position 79 commonly have an excellent growth-suppressing activity on cancer cells having a mutated Ras gene. The use of the antibody of the present invention enables treatment of cancers. The antibody of the present invention is effective also in treatment of Ras mutated cancers highly resistant to available drugs. Moreover, the antibody of the present invention is applicable also to diagnosis of a cancer.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 5a shows photographs for illustrating the inhibition effect of each anti-TGF-α antibody on EGFR tyrosine phosphorylation in EGFR-overexpressing cancer cell A431 cells. As experimental controls, TGF-α neutralized antibody clone 189-2130 (NPL 50) and cetuximab-parent antibody 225 were used. p-EGFR shows the result of western blotting with antiphosphorylation tyrosine EGFR antibodies. EGFR shows the result of re-blotting of the same test membrane with anti-EGFR antibodies.

FIG. 5b is a graph for illustrating the inhibition effect of each anti-TGF-α antibody on EGFR tyrosine phosphorylation in the EGFR-overexpressing cancer cell A431 cells. As the experimental control, TGF-α neutralized antibody clone 189-2130 (NPL 50) and cetuximab-parent antibody 225 were used. Relative values of the EGFR phosphorylation level under each experimental condition are shown in the graph with the EGFR phosphorylation level of 0% indicating when TGF-α was not added, and the EGFR phosphorylation level of 100% indicating when TGF-α was added.

FIG. 6 shows graphs for illustrating the result of analyzing, by flow cytometry, the reactivity of the anti-TGF-α antibody MBL259-3 on various solid cancer cell lines. As cancer cells, a colorectal cancer-derived K-Ras gene-homo mutated cell line SW620 and a lung cancer-derived K-Ras-hetero mutated cell line A427 were used. As the detection results, the upper graphs show the reactivity of mouse IgG as a mouse isotype control antibody while lower graphs show the reactivity of the anti-TGF-α antibody MBL259-3.

FIG. 15 is a representation for illustrating the primary structures of variable regions of MBL009-15 (light chain: SEQ ID NOs: 3 and 142 for amino acid and nucleic acid sequences, respectively; and heavy chain: SEQ ID NOs: 4 and 144 for amino acid and nucleic acid sequences, respectively).

FIG. 16 is a representation for illustrating the primary structures of variable regions of MBL016-8 (light chain: SEQ ID NOs: 5 and 146 for amino acid and nucleic acid sequences, respectively; and heavy chain: SEQ ID NOs: 6 and 148 for amino acid and nucleic acid sequences, respectively).

FIG. 17 is a representation for illustrating the primary structures of variable regions of MBL018-1 (light chain: SEQ ID NOs: 7 and 150 for amino acid and nucleic acid sequences, respectively; and heavy chain: SEQ ID NOs: 8 and 152 for amino acid and nucleic acid sequences, respectively).

FIG. 18 is a representation for illustrating the primary structures of variable regions of MBL144-1 (light chain: SEQ ID NOs: 9 and 154 for amino acid and nucleic acid sequences, respectively; and heavy chain: SEQ ID NOs: 10 and 156 for amino acid and nucleic acid sequences, respectively).

FIG. 19 is a representation for illustrating the primary structures of variable regions of MBL184-6 (light chain: SEQ ID NOs: 11 and 158 for amino acid and nucleic acid sequences, respectively; and heavy chain: SEQ ID NOs: 12 and 160 for amino acid and nucleic acid sequences, respectively).

FIG. 20 is a representation for illustrating the primary structures of variable regions of MBL259-3 (light chain: SEQ ID NOs: 13 and 162 for amino acid and nucleic acid sequences, respectively; and heavy chain: SEQ ID NOs: 14 and 164 for amino acid and nucleic acid sequences, respectively).

FIG. 21 is a representation for illustrating the primary structures of variable regions of MBL292-1 (light chain: SEQ ID NOs: 15 and 166 for amino acid and nucleic acid sequences, respectively; and heavy chain: SEQ ID NOs: 16 and 168 for amino acid and nucleic acid sequences, respectively).

FIG. 22 is a representation for illustrating the primary structures of variable regions of MBL352-34 (light chain: SEQ ID NOs: 17 and 170 for amino acid and nucleic acid sequences, respectively; and heavy chain: SEQ ID NOs: 18 and 172 for amino acid and nucleic acid sequences, respectively).

DESCRIPTION OF EMBODIMENTS

Figure 1:
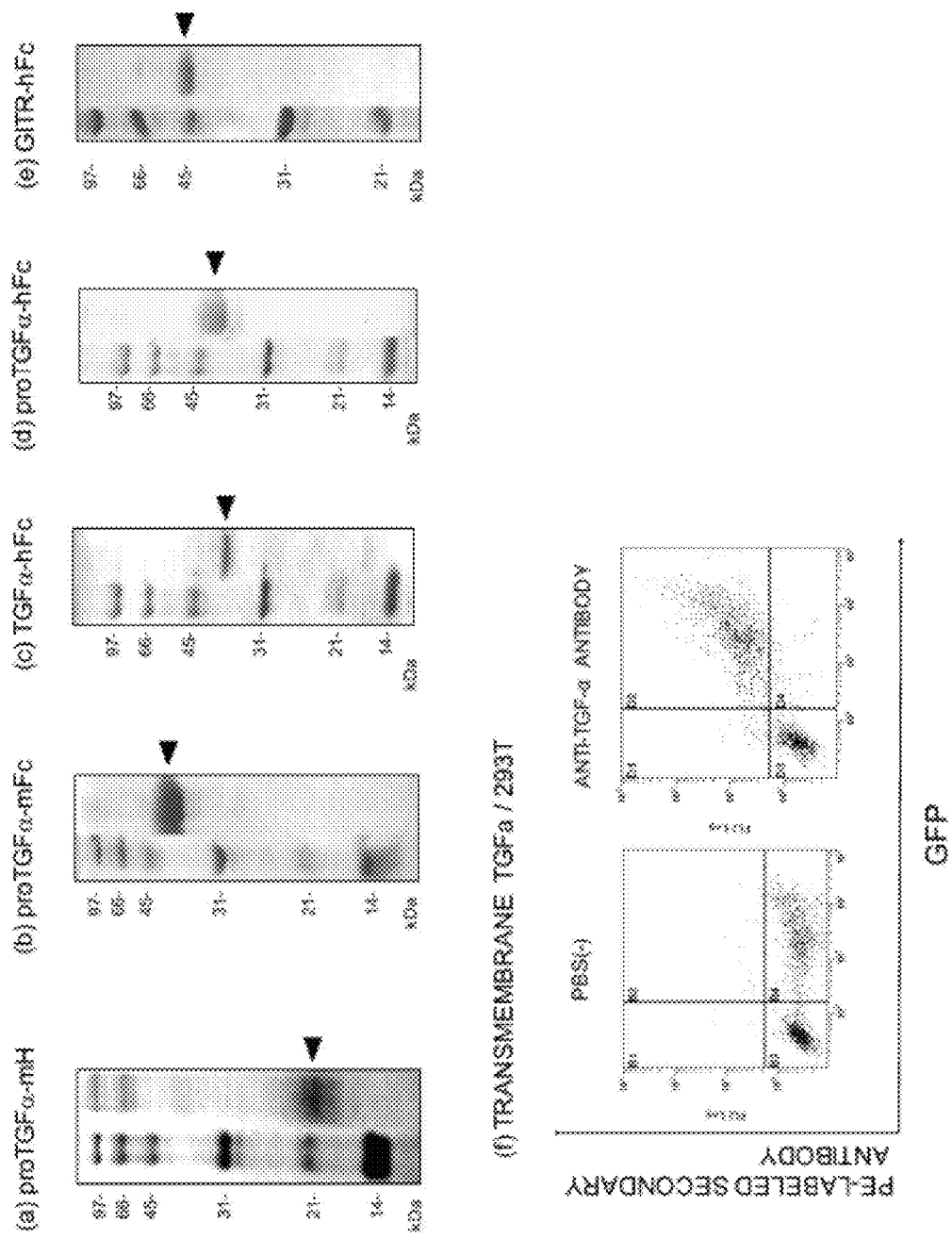
FIG. 1 shows drawings for illustrating immunogens used to obtain anti-TGF-α monoclonal antibodies and antigens for screening antibodies. Immunogens proTGF-α-mH (a) and proTGF-α-mFc (b), as well as TGF-α-hFc (c), proTGF-α-hFc (d), and GITR-hFc (e) for screening antibodies were each subjected to SDS electrophoresis, separated on a gel, and stained with CBB. mFc indicates the Fc portion of mouse IgG2a, and hFc indicates the Fc portion of human IgG1. Moreover, mH indicates that myc and His tags are consecutively fused. (f) illustrates the reactivity between 293T cells transiently expressing transmembrane TGF-α and anti-TGF-α antibody (R&D systems Inc.) (right) or a negative control PBS(−) (left). The mechanism is such that a fluorescent protein (Green Fluorescent Protein: GFP, Cell Biolabs, Inc.)) exhibits fluorescence in proportion to the amount of TGF-α expressed. A phycoerythrin (PE)-labeled anti-IgG antibody was used as the secondary antibody. In the two-dimensional separation carried out on antibody-reacting cells with flow cytometry, if the antibody reacts with TGF-α, dots representing the fluorescence are spread to the upper right (FIG. 1f, right).

The present invention provides an antibody against human TGF-α and showing a growth-suppressing activity on cancer cells having a mutated Ras gene.

In the present invention, the phrase "showing a growth-suppressing activity on cancer cells having a mutated Ras gene" means showing a growth-suppressing activity on cancer cells having a mutated Ras gene in vitro and/or in vivo. As long as having the growth-suppressing activity on cancer cells having a mutated Ras gene, the antibody of the present invention may further have a growth-suppressing activity on cancer cells having no mutated Ras gene. The in vitro activity can be evaluated as follows. For example, using a three-dimensional cell culture system where cells are cultured in a gel medium, cancer cells (for example, A427 or SW620) having a mutated Ras gene (for example, K-Ras gene) are allowed to proliferate. A test antibody is added to the culture system. Then, the proliferation of these cancer cells are detected for the evaluation (see Example 5). Meanwhile, the in vivo activity can be evaluated as follows. For example, a test antibody is subcutaneously administered to a nude mouse into which cancer cells having a mutated Ras gene (for example, A427 or SW620) have been subcutaneously transplanted. Then, the tumor size is measured for the evaluation (see Example 4). Examples of the antibody having such an activity include MBL009-15, MBL016-8, MBL018-1, MBL023-1, MBL144-1, MBL184-6, MBL259-3, MBL292-1, and MBL352-34 described in the present Examples.

SEQ ID NO: 2 shows a typical amino acid sequence of "human TGF-α" to which the antibody of the present invention binds (wild type amino acid sequence), and SEQ ID NO: 1 shows a typical base sequence of a gene encoding the same. A preferable embodiment of the antibody of the present invention is an antibody less reactive with human TGF-α having mutated glycine at position 79 (for example, G79A-substituted human TGF-α) than with wild type human TGF-α. A more preferable embodiment of the antibody of the present invention is an antibody which is non-reactive with human TGF-α having mutated glycine at position 79 (for example, G79A-substituted human TGF-α). MBL009-15, MBL016-8, MBL018-1, MBL023-1, MBL144-1, MBL184-6, MBL259-3, MBL292-1, and MBL352-34 aforementioned have demonstrated a growth-suppressing activity on cancer cells having a mutated Ras gene in the present Examples, and commonly have significantly low reactivity with G79A-substituted human TGF-α. Thus, such low reactivity of an antibody with human TGF-α having mutated glycine at position 79 (for example, G79A-substituted human TGF-α) has a high correlation with the growth-suppressing activity of the antibody on cancer cells having a mutated Ras gene.

Another preferable embodiment of the antibody of the present invention is an antibody having an activity of suppressing EGFR tyrosine phosphorylation. The suppression of EGFR tyrosine phosphorylation by an antibody can be evaluated, for example, as follows. When TGF-α is added to EGFR-overexpressing cells (for example, A431) cultured in a serum-free medium, the EGFR tyrosine phosphorylation (P-Tyr1173) level is transiently increased. In a case where a test antibody has an activity of suppressing EGFR tyrosine phosphorylation, the TGF-α solution is allowed to react with the test antibody in advance to treat the EGFR-overexpressing cells therewith. In this case, the EGFR phosphorylation level shows a small value in comparison with a negative control (for example, PBS). In this manner, the EGFR phosphorylation level is measured using the test antibody in comparison with the level obtained using a negative control, and thereby the activity of suppressing EGFR tyrosine phosphorylation by a test antibody can be evaluated (see Example 2). The antibody of the present invention is preferably an antibody capable of suppressing EGFR tyrosine phosphorylation (P-Tyr1173) by 50% or more, more preferably an antibody capable of suppressing 70% or more (for example, 80% or more, 90% or more, 100% or more), when the antibody is added at a concentration of 10 μg/mL. Examples of the antibody having such an activity include MBL352-34, MBL292-1, MBL184-6, MBL016-8, MBL144-1, MBL023-1, and MBL018-1 described in the present Examples.

Another preferable embodiment of the antibody of the present invention is an antibody having an activity of suppressing induction of vascular endothelial cells. In evaluating the activity, for example, an angiogenesis evaluation system in a mouse hypodermis can be utilized. For example, using commercially-available Directed In Vivo Angiogenesis Assay (Trevigen Inc.), the activity can be evaluated, as an activity of a test antibody suppressing migration of vascular endothelial cells into an angioreactor due to human TGF-α (see Example 6). Examples of the antibody having such an activity include MBL009-15, MBL016-8, MBL018-1, MBL023-1, MBL292-1, and MBL352-34 described in the present Examples.

The antibody of the present invention is particularly preferably an antibody having multiple activities described above in combination.

Another preferable embodiment of the antibody of the present invention is: an antibody comprising a light chain variable region including light chain CDR1 to CDR3 and a heavy chain variable region including heavy chain CDR1 to CDR3 of the antibodies described in the present Examples; or amino acid sequence mutants thereof. Specifically, the antibody has any one of the following characteristics (a) to (h):

<MBL009-15>

(a) comprising
a light chain variable region including amino acid sequences of SEQ ID NOs: 19 to 21 or the amino acid sequences in at least any one of which one or more amino acids are substituted, deleted, added and/or inserted, and
a heavy chain variable region including amino acid sequences of SEQ ID NOs: 22 to 24 or the amino acid sequences in at least any one of which one or more amino acids are substituted, deleted, added and/or inserted;

<MBL016-8>

(b) comprising
a light chain variable region including amino acid sequences of SEQ ID NOs: 25 to 27 or the amino acid sequences in at least any one of which one or more amino acids are substituted, deleted, added and/or inserted, and
a heavy chain variable region including amino acid sequences of SEQ ID NOs: 28 to 30 or the amino acid sequences in at least any one of which one or more amino acids are substituted, deleted, added and/or inserted;

<MBL018-1>

(c) comprising
a light chain variable region including amino acid sequences of SEQ ID NOs: 31 to 33 or the amino acid sequences in at least any one of which one or more amino acids are substituted, deleted, added and/or inserted, and
a heavy chain variable region including amino acid sequences of SEQ ID NOs: 34 to 36 or the amino acid sequences in at least any one of which one or more amino acids are substituted, deleted, added and/or inserted;

<MBL144-1>

(d) comprising
a light chain variable region including amino acid sequences of SEQ ID NOs: 37 to 39 or the amino acid sequences in at least any one of which one or more amino acids are substituted, deleted, added and/or inserted, and
a heavy chain variable region including amino acid sequences of SEQ ID NOs: 40 to 42 or the amino acid sequences in at least any one of which one or more amino acids are substituted, deleted, added and/or inserted;

<MBL184-6>

(e) comprising
a light chain variable region including amino acid sequences of SEQ ID NOs: 43 to 45 or the amino acid sequences in at least any one of which one or more amino acids are substituted, deleted, added and/or inserted, and
a heavy chain variable region including amino acid sequences of SEQ ID NOs: 46 to 48 or the amino acid sequences in at least any one of which one or more amino acids are substituted, deleted, added and/or inserted;

<MBL259-3>

(f) comprising
a light chain variable region including amino acid sequences of SEQ ID NOs: 49 to 51 or the amino acid sequences in at least any one of which one or more amino acids are substituted, deleted, added and/or inserted, and
a heavy chain variable region including amino acid sequences of SEQ ID NOs: 52 to 54 or the amino acid sequences in at least any one of which one or more amino acids are substituted, deleted, added and/or inserted;

<MBL292-1>

(g) comprising
a light chain variable region including amino acid sequences of SEQ ID NOs: 55 to 57 or the amino acid sequences in at least any one of which one or more amino acids are substituted, deleted, added and/or inserted, and
a heavy chain variable region including amino acid sequences of SEQ ID NOs: 58 to 60 or the amino acid sequences in at least any one of which one or more amino acids are substituted, deleted, added and/or inserted; and

<MBL352-34>

(h) comprising
a light chain variable region including amino acid sequences of SEQ ID NOs: 61 to 63 or the amino acid sequences in at least any one of which one or more amino acids are substituted, deleted, added and/or inserted, and
a heavy chain variable region including amino acid sequences of SEQ ID NOs: 64 to 66 or the amino acid sequences in at least any one of which one or more amino acids are substituted, deleted, added and/or inserted.

Another preferable embodiment of the antibody of the present invention is: an antibody comprising alight chain variable region and a heavy chain variable regions of antibodies described in the present Examples; or amino acid sequence mutants thereof. Specifically, the antibody has any one of the following characteristics (a) to (h):

<MBL009-15>

(a) comprising
a light chain variable region including an amino acid sequence of SEQ ID NO: 3 or the amino acid sequence in which one or more amino acids are substituted, deleted, added and/or inserted, and
a heavy chain variable region including an amino acid sequence of SEQ ID NO: 4 or the amino acid sequence in which one or more amino acids are substituted, deleted, added and/or inserted;

<MBL016-8>

(b) comprising
a light chain variable region including an amino acid sequence of SEQ ID NO: 5 or the amino acid sequence in which one or more amino acids are substituted, deleted, added and/or inserted, and
a heavy chain variable region including an amino acid sequence of SEQ ID NO: 6 or the amino acid sequence in which one or more amino acids are substituted, deleted, added and/or inserted;

<MBL018-1>

(c) comprising
a light chain variable region including an amino acid sequence of SEQ ID NO: 7 or the amino acid sequence in which one or more amino acids are substituted, deleted, added and/or inserted, and
a heavy chain variable region including an amino acid sequence of SEQ ID NO: 8 or the amino acid sequence in which one or more amino acids are substituted, deleted, added and/or inserted;
<MBL144-1>
(d) comprising
a light chain variable region including an amino acid sequence of SEQ ID NO: 9 or the amino acid sequence in which one or more amino acids are substituted, deleted, added and/or inserted, and
a heavy chain variable region including an amino acid sequence of SEQ ID NO: 10 or the amino acid sequence in which one or more amino acids are substituted, deleted, added and/or inserted;
<MBL184-6>
(e) comprising
a light chain variable region including an amino acid sequence of SEQ ID NO: 11 or the amino acid sequence in which one or more amino acids are substituted, deleted, added and/or inserted, and
a heavy chain variable region including an amino acid sequence of SEQ ID NO: 12 or the amino acid sequence in which one or more amino acids are substituted, deleted, added and/or inserted;
<MBL259-3>
(f) comprising
a light chain variable region including an amino acid sequence of SEQ ID NO: 13 or the amino acid sequence in which one or more amino acids are substituted, deleted, added and/or inserted, and
a heavy chain variable region including an amino acid sequence of SEQ ID NO: 14 or the amino acid sequence in which one or more amino acids are substituted, deleted, added and/or inserted;
<MBL292-1>
(g) comprising
a light chain variable region including an amino acid sequence of SEQ ID NO: 15 or the amino acid sequence in which one or more amino acids are substituted, deleted, added and/or inserted, and
a heavy chain variable region including an amino acid sequence of SEQ ID NO: 16 or the amino acid sequence in which one or more amino acids are substituted, deleted, added and/or inserted; and
<MBL352-34>
(h) comprising
a light chain variable region including an amino acid sequence of SEQ ID NO: 17 or the amino acid sequence in which one or more amino acids are substituted, deleted, added and/or inserted, and
a heavy chain variable region including an amino acid sequence of SEQ ID NO: 18 or the amino acid sequence in which one or more amino acids are substituted, deleted, added and/or inserted.

Another preferable embodiment of the antibody of the present invention is the MBL023-1 antibody described in the present Examples. A hybridoma producing the antibody has been deposited at International Patent Organism Depositary, National Institute of Advanced Industrial Science and Technology (Central 6, 1-1-1, Higashi, Tsukuba, Ibaraki (postal code 305-8566), Japan) under an accession number of FERM ABP-11377 since Apr. 20, 2011. Thus, the MBL023-1 antibody is specifically an antibody produced by a hybridoma specified under an accession number of FERM ABP-11377.

Once the above-described antibody (for example, the antibodies in the present Examples) is obtained, those skilled in the art can prepare various antibodies which recognize an epitope recognized by the antibody.

In the present invention, the "antibody" includes all classes and subclasses of immunoglobulins. The "antibody" includes a polyclonal antibody and a monoclonal antibody, and is also meant to include the form of a functional fragment of an antibody. A "polyclonal antibody" is an antibody preparation including different antibodies against different epitopes. Meanwhile, a "monoclonal antibody" means an antibody (including an antibody fragment) obtained from a substantially homogeneous antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

The antibody of the present invention includes a chimeric antibody, a humanized antibody, a human antibody, and functional fragments of these antibodies. For administration to human as a medicine, the antibody of the present invention is desirably a chimeric antibody, a humanized antibody, or a human antibody from the viewpoint of side effect reduction.

In the present invention, a "chimeric antibody" is an antibody obtained by linking a variable region of an antibody of one species to a constant region of an antibody of another species. For example, a chimeric antibody can be obtained as follows. A mouse is immunized with an antigen. A portion corresponding to an antibody variable part (variable region) which binds to an antigen is cut out from a gene of a monoclonal antibody of the mouse. The portion is linked to a gene encoding a constant part (constant region) of an antibody derived from human bone marrow. This is incorporated into an expression vector. The expression vector is introduced into a host for production of the chimeric antibody (for example, Japanese unexamined Patent Application Publication No. Hei 7-194384, Japanese Patent No. 3238049, U.S. Pat. Nos. 4,816,397, 4,816,567, 5,807,715). Moreover, in the present invention, a "humanized antibody" is an antibody obtaining by grafting (CDR grafting) a gene sequence of an antigen-binding site (CDR) of a non-human-derived antibody onto a human antibody gene. The preparation methods are known (see, for example, Japanese Patent No. 2912618, Japanese Patent No. 2828340, Japanese Patent No. 3068507, Europe Patent No. 239400, Europe Patent No. 125023, International Publication No. WO90/07861, International Publication No. WO96/02576). In the present invention, a "human antibody" is an antibody of which all regions are derived from human. In preparing a human antibody, it is possible to utilize a transgenic animal (for example, a mouse) capable of producing a repertoire of the human antibody by immunization. Preparation methods of a human antibody are known (for example, Nature, 362: 255-258 (1992), Intern. Rev. Immunol, 13: 65-93 (1995), J. Mol. Biol, 222: 581-597 (1991), Nature Genetics, 15: 146-156 (1997), Proc. Natl. Acad. Sci. USA, 97: 722-727 (2000), Japanese unexamined Patent Application Publication No. Hei 10-146194, Japanese unexamined Patent Application Publication No. Hei 10-155492, Japanese Patent No. 2938569, Japanese unexamined Patent Application Publication No. Hei 11-206387, International Application Japanese-Phase Publication No. Hei 8-509612, International Application Japanese-Phase Publication No. Hei 11-505107).

In the present invention, a "functional fragment" of an antibody means a part (partial fragment) of an antibody, which specifically recognizes human TGF-α. Specific examples thereof include Fab, Fab', F(ab')2, a variable region fragment (Fv), a disulfide bonded Fv, a single chain Fv (scFv), sc(Fv)2, a diabody, a polyspecific antibody, polymers thereof, and the like.

Here, "Fab" means a monovalent antigen-binding fragment, of an immunoglobulin, composed of a part of one light chain and a part of one heavy chain. Fab can be obtained by papain-digestion of an antibody or a recombinant method. "Fab'" differs from Fab in that a small number of residues are added to the carboxy terminus of a heavy chain CH1 domain including one or more cysteines from an antibody hinge region. "F(ab')2" means a bivalent antigen-binding fragment, of an immunoglobulin, composed of parts of both light chains and parts of both heavy chains.

A "variable region fragment (Fv)" is a smallest antibody fragment having a complete antigen recognition and binding site. An Fv is a dimer in which a heavy chain variable region and a light chain variable region are linked by non-covalent bonding. A "single-chain Fv (sFv)" includes a heavy chain variable region and a light chain variable region of an antibody, and these regions exist in a single polypeptide chain. A "sc(Fv)2" is a single chain obtained by linking two heavy chain variable regions and two light chain variable regions with a linker or the like. A "diabody" is a small antibody fragment having two antigen binding sites. The fragment includes a heavy chain variable region linked to a light chain variable region in a single polypeptide chain. Each region forms a pair with a complementary region in another chain. A "polyspecific antibody" is a monoclonal antibody having a binding specificity to at least two different antigens. For example, a polyspecific antibody can be prepared by coexpression of two immunoglobulin heavy chain/light chain pairs in which two heavy chains have mutually different specificities.

The antibody of the present invention includes antibodies whose amino acid sequences are modified without impairing desirable activities (for example, growth-suppressing activity on cancer cells having a mutated Ras gene, reactivity with wild type human TGF-α and G79A-substituted human TGF-α, activity of suppressing EGFR tyrosine phosphorylation, or activity of suppressing induction of vascular endothelial cells). An amino acid sequence mutant of the antibody of the present invention can be prepared by introduction of mutation into a DNA encoding an antibody chain of the present invention or by peptide synthesis. Examples of such a modification include substitution, deletion, addition and/or insertion of a residue in the amino acid sequence of the antibody of the present invention. A site where the amino acid sequence of the antibody is modified may be a constant region of a heavy chain or a light chain of the antibody or a variable region (framework region and CDR) thereof, as long as the resulting antibody has activities equivalent to those of the antibody before the modification. It is conceivable that modification on an amino acid other than those in CDR has relatively small influence on binding affinity for an antigen. As of now, there are known screening method for antibodies whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

The number of amino acids modified other than those in CDR is preferably 10 amino acids or less, more preferably 5 amino acids or less, and most preferably 3 amino acids or less (for example, 2 amino acids or less, 1 amino acid). The amino acid modification is preferably conservative substitution. In the present invention, the "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), sulfur-containing amino acids (cysteine, methionine), amino acids having an amide group (asparagine, glutamine), an amino acid having an imino group (proline), and amino acids having an aromatic group (phenylalanine, tyrosine, tryptophan).

In addition, the modification on the antibody of the present invention may be a modification on post-translational process of the antibody, for example, the change in the number of sites of glycosylation or in location or type of the glycosylation. This can improve, for example, the ADCC activity of the antibody. Glycosylation of an antibody is typically N-linked or O-linked glycosylation. The glycosylation of an antibody greatly depends on a host cell used for expression of the antibody. The glycosylation pattern can be modified by known methods such as introduction or deletion of a certain enzyme involved in carbohydrate production (Japanese unexamined Patent Application Publication No. 2008-113663, Japanese Patent No. 4368530, Japanese Patent No. 4290423, U.S. Pat. Nos. 5,047,335, 5,510,261, 5,278,299, International Publication No. WO99/54342).

Further, in the present invention, for the purpose of increasing the stability of an antibody or other purposes, an amino acid subjected to deamidation or an amino acid adjacent to the amino acid subjected to deamidation may be substituted with a different amino acid to suppress the deamidation. Moreover, the stability of an antibody can also increased by substituting glutamic acid with a different amino acid. The present invention also provides an antibody thus stabilized.

When the antibody of the present invention is a polyclonal antibody, the polyclonal antibody can be obtained as follows. Specifically, an animal to be immunized is immunized with an antigen (TGF-α, a partial peptide thereof, cells expressing these, or the like). The polyclonal antibody can be obtained by purification of an antiserum obtained from the animal by conventional means (for example, salting-out, centrifugation, dialysis, column chromatography, or the like). Meanwhile, a monoclonal antibody can be prepared by a hybridoma method or a recombinant DNA method.

A typical example of the hybridoma method is a method by Kohler and Milstein (Kohler & Milstein, Nature, 256: 495 (1975)). Antibody-producing cells used in cell fusion process of this method are spleen cells, lymph node cells, peripheral blood leukocytes, and the like of an animal (for example, mouse, rat, hamster, rabbit, monkey, goat) immunized with an antigen (human TGF-α, a partial peptide thereof, cells expressing these, or the like). It is also possible to use antibody-producing cells obtained by causing the antigen to act, in a medium, on the above-described types of cells, lymphocyte, or the like, which are isolated from non-immunized animals in advance. As myeloma cells, known various cell lines can be used. The antibody-producing cells and the myeloma cells may be ones originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to human TGF-α can be obtained. The monoclonal antibody against human TGF-α can be obtained by culturing the hybridoma, or from the ascites of a mammal to which the hybridoma is administered.

The recombinant DNA method is a method by which the antibody of the present invention is produced as a recombinant antibody as follows. A DNA encoding the antibody of the present invention or a peptide thereof is cloned from a hybridoma, B cells, or the like. The cloned DNA is incorporated into an appropriate vector, which is introduced into host cells (for example, a mammalian cell line, *Escherichia coli*, yeast cells, insect cells, plant cells, or the like) for the production (for example, P. J. Delves, Antibody Production: Essential Techniques, 1997 WILEY, P. Shepherd and C. Dean, Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding a heavy chain and a light chain may be incorporated into expression vectors, respectively, to transform the host cells. Alternatively, DNAs encoding a heavy chain and a light chain may be incorporated into a single expression vector to transform the host cells (see International Publication No. WO94/11523). The antibody of the present invention can be obtained in a substantially pure and homogeneous form by culturing the host cells, followed by separation and purification from the host cells or the culture solution. For the separation and purification of the antibody, normal methods used for polypeptide purification can be employed. When a transgenic animal (cattle, goat, sheep, pig, or the like) in which an antibody gene is incorporated is produced using a transgenic animal production technique, a large amount of monoclonal antibodies derived from the antibody gene can also be obtained from milk of the transgenic animal.

The present invention also provides: a DNA encoding the antibody or peptide of the present invention; a vector comprising the DNA; host cells comprising the DNA; and a method for producing the antibody, comprising culturing the host cells and recovering the antibody.

As described above, it has been found out in the present invention that there is a high correlation between low reactivity of anti-human TGF-α antibodies with human TGF-α having mutated glycine at position 79 (for example, G79A-substituted human TGF-α) and the growth-suppressing activity on cancer cells having a mutated Ras gene. Based on such a knowledge, anti-human TGF-α antibodies showing a growth-suppressing activity on cancer cells having a mutated Ras gene can be produced by selecting an antibody less reactive with human TGF-α having mutated glycine at position 79 (for example, G79A-substituted human TGF-α) than with wild type human TGF-α. Thus, the present invention also provides a method for producing an anti-human TGF-α antibody showing a growth-suppressing activity on cancer cells having a mutated Ras gene, the method comprising the steps of:

(a) preparing antibodies capable of binding to human TGF-α; and (b) selecting, from the prepared antibodies, an antibody less reactive with human TGF-α having mutated glycine at position 79 than with wild type human TGF-α. The reactivity of an antibody with wild type human TGF-α or human TGF-α having mutated glycine at position 79 (for example, G79A-substituted human TGF-α) can be evaluated, for example, by preparing 293T cells each expressing TGF-α on the cell surface and analyzing the reactivity between the cell and a test antibody by flow cytometry (see Example 7). Furthermore, the present invention also provides human TGF-α having mutated glycine at position 79 (for example, G79A-substituted human TGF-α) that is useful in such a method for producing an anti-human TGF-α antibody.

Since having a growth-suppressing activity on cancer cells having a mutated Ras gene, the antibody of the present invention can be utilized as an anti-cancer agent. Thus, the present invention also provides: an anti-cancer agent comprising the antibody of the present invention as an active ingredient; and a method for treating a cancer, comprising the step of administering a therapeutically effective amount of the antibody of the present invention to a mammal including a human. The treatment method of the present invention is applicable to, other than human, various mammals including, for example, dogs, cats, cattle, horses, sheep, pigs, goats, rabbits, and so forth. The antibody of the present invention is effective also in treatment of Ras mutated cancers highly resistant to available drugs.

The anti-cancer agent comprising the antibody of the present invention as an active ingredient can be used in the form of a composition comprising the antibody of the present invention and any component, for example, a saline, an aqueous glucose solution, a phosphate buffer, or the like. The anti-cancer agent of the present invention may be formulated, as necessary, in a liquid or lyophilized form, and may optionally comprise a pharmaceutically acceptable carrier or medium, for example, a stabilizer, a preservative, an isotonic agent, or the like.

Examples of the pharmaceutically acceptable carrier include: mannitol, lactose, saccharose, human albumin, and the like for a lyophilized preparation; and a saline, water for injection, a phosphate buffer, aluminium hydroxide, and the like for a liquid preparation. However, the examples are not limited thereto.

The method for administering the anti-cancer agent of the present invention differs depending on the age, weight, gender, general health state, and the like of an administration target. The administration can be carried out by any administration route of oral administration and parenteral administration (for example, intravenous administration, intraarterial administration, local administration). A preferable administration method is parenteral administration. The dose of the anti-cancer agent of the present invention varies depending on the age, weight, gender, and health state of a patient, the degree of cancer progress, and components of the anti-cancer agent to be administered. In a case of intravenous administration, the dose is generally 0.1 to 1000 mg, preferably 1 to 100 mg, per kg body weight per day for an adult.

It is conceivable that the antibody of the present invention is applicable not only to treatment of cancers but also to diagnosis of cancers. The present inventors have found out that antibodies less reactive with human TGF-α having mutated glycine at position 79 (for example, G79A-substituted human TGF-α) than with wild type human TGF-α are also useful for diagnosis of a cancer particularly having a mutated Ras gene. When the antibody of the present invention is used for diagnosis of a cancer or detection of a cancer, the antibody of the present invention may be labeled. As such a label, it is possible to use, for example, a radioactive substance, a fluorescent dye, a chemiluminescent substance, an enzyme, and a coenzyme. Specific examples thereof include radioisotopes, fluoresceins, rhodamines, dansyl chloride, luciferases, peroxidases, alkaline phosphatases, lysozymes, biotin/avidin, and the like. When the antibody of the present invention is to be prepared as a diagnostic agent, the diagnostic agent can be obtained in any dosage form by adopting any means suitable for the purpose. For example, a purified antibody is measured for the antibody titer and appropriately diluted with PBS (phosphate buffer containing saline) or the like; thereafter, a preservative such as 0.1% sodium azide can be added thereto. Alternatively, for example, the antibody of the present invention adsorbed to latex or the like is determined for the antibody titer and appropriately diluted, and a preservative can be added thereto for use.

EXAMPLES

Hereinafter, the present invention will be described more specifically based on Examples and Comparative Example. However, the present invention is not limited to the following Examples.

[Methods and Materials]

1. Method for Producing Anti-TGF-α Monoclonal Antibodies (1) Preparations of Immunogens and Antigens for Screening Antibodies In order to obtain mouse monoclonal antibodies against TGF-α, the following two immunogens were prepared. As for the first one, a gene corresponding to positions 24 to 89 in the amino acid sequence (positions 70 to 267 in the base sequence) of human TGF-α was amplified from a placenta cDNA library by a PCR method. The PCR product thus obtained was cloned in an expression vector pSecTag2 (Invitrogen Corporation) used for cultured animal cells. Further, the human TGF-α (positions 70 to 267 in the base sequence) containing the leader sequence derived from pSecTag2 was subcloned in a retroviral vector pQCXIP (Takara Bio Inc.). The vector was designed in such a way that myc and His were consecutively fused as a tag on the C-terminal side of TGF-α. Using Lipofectamine 2000, the gene was introduced together with the prepared vector and env vector (pVSVG) into GP293 cells, which are viral packaging cells. Next, a virus fluid obtained from the culture supernatant was used to infect 293T cells. Thereby, a cell line stably producing TGF-α was obtained. The supernatant obtained after culturing for 10 days was passed through a column filled with a TALON resin (Takara Bio Inc.). The column was washed with a binding buffer solution containing 5 mM imidazole in a 10-fold amount of the resin. Then, the bound material was eluted with a 100-mM imidazole solution. After overnight dialysis with PBS, a part of the eluate was subjected to SDS electrophoresis. A target band was observed to have a molecular weight around 19 to kDa (FIG. 1a). This was used as an immunogen (hereinafter, this immunogen is referred to as proTGF-α-mH). As for the second one, a gene corresponding to positions 1 to 89 in the amino acid sequence (positions 1 to 267 in the base sequence) of human TGF-α was amplified from the placenta cDNA library by the PCR method, and cloned in pCAGGS (gratefully received from Professor Junichi Miyazaki at Graduate School of Medicine/Faculty of Medicine, Osaka University. Gene (1991) 108 (2): 193-199). The vector was designed in such a way that the gene of the Fc portion of mouse immunoglobulin G2a was fused on the 3' side. The vector was introduced into human cultured cells 293T using a gene introduction reagent Lipofectamine 2000 (Invitrogen Corporation). The culture supernatant was collected by centrifugal operation. The amount of the plasmid DNA, cell count, and the amount of Lipofectamine were as described in the product leaflet. The obtained supernatant was passed through a column filled with Protein G beads (GE Company). The column was washed with a binding buffer solution in a 10-fold amount of the beads. Then, the material adsorbed to the column was eluted with a glycine hydrochloride solution at pH 2.3. After promptly neutralized with a Tris-HCl buffer solution at pH 8.0, the resultant was subjected to overnight dialysis with PBS. A part of the extract was subjected to SDS electrophoresis. A target single band was observed to have a molecular weight around 40 to 44 kDa (FIG. 1b). This was used as an immunogen (hereinafter, this immunogen is referred to as proTGF-α-mFc).

Moreover, in order to prepare antigens for screening to check the reactivity of antibodies to be obtained with TGF-α, the following four expression vectors were constructed. As for the first vector, a gene corresponding to positions 40 to 89 in the amino acid sequence (positions 118 to 267 in the base sequence) of mature TGF-α of human TGF-α was amplified from the placenta cDNA library by the PCR method. The PCR product thus obtained was cloned in an expression vector pSecTag2 used for cultured animal cells. Then, the human TGF-α (positions 118 to 267 in the base sequence) containing the leader sequence derived from pSecTag2 was subcloned in a pcDNA3.1 vector (Invitrogen Corporation). The vector was designed in such a way that the gene of the Fc portion of human immunoglobulin G1 was fused on the C-terminal side of TGF-α (hereinafter, an antigen prepared with this expression vector is referred to as TGF-α-hFc). As for the second vector, a gene corresponding to positions 1 to 89 in the amino acid sequence (positions 1 to 267 in the base sequence) of human TGF-α was amplified from the placenta cDNA library by the PCR method. The PCR product thus obtained was cloned in an expression vector pcDNA3.1 used for cultured animal cells. The vector was designed in such a way that the Fc portion of human immunoglobulin G1 was fused on the C-terminal side of TGF-α (hereinafter, an antigen prepared with this expression vector is referred to as proTGF-α-hFc). As the third vector, for the purpose of examining a non-specific reaction of an antibody with the Fc portion of human immunoglobulin G1, a vector pcDNA-GITR-hFc was constructed in which the gene sequence (1 to 495 bases) corresponding to the length of the extracellular region of human GITR was fused with the gene of the Fc portion of human immunoglobulin G1 (hereinafter, an antigen prepared with this expression vector is referred to as GITR-hFc). Each of the expression vectors was introduced into human cultured cells 293T by lipofection. After 3 to 4 days, the culture supernatant was collected. The antigens for screening antibodies, TGF-α-hFc, proTGF-α-hFc, and GITR-hFc, contained in the culture supernatant were recovered and purified in accordance with the above-described method for preparing the immunogens (FIGS. 1c-e). The fourth expression vector was constructed for the purpose of examining the reactivity with transmembrane TGF-α expressed on the cell surface. A gene corresponding to positions 1 to 160 in the amino acid sequence (positions 1 to 480 in the base sequence) of human TGF-α was cloned in an expression vector pcDNA3.1 used for animal cells. The vector was designed in such a way that the ribosome entry site IRES and the gene of a fluorescent protein GFP (Cell Biolabs, Inc.) are linked on the 3' side of the TGF-α gene (hereinafter, this expression vector is referred to as pDIG-TGF-α). This expression vector is characterized by having such a mechanism that when the expression vector is transiently introduced into 293T cells by lipofection, the GFP exhibits fluorescence only in cells expressing transmembrane TGF-α. After a primary antibody and a PE-labeled secondary antibody are reacted with these cells, a two-dimensional separation is carried out with flow cytometry. In this case, if an antigen-antibody reaction occurs, data is obtained such that dots representing only cells having the GFP exhibiting fluorescence are shifted to the upper right (FIG. 1f) (hereinafter, 293T cells into which this expression vector is transiently introduced are referred to as TGF-α/293T).

(2) Immunization with Immunogens and Establishment of Hybridoma

As the immunogen, proTGF-α-mFc alone or a combination of proTGF-α-mFc and proTGF-α-mH was used. Each solution of these was mixed with an equal amount of Complete Freund's Adjuvant. Then, mice of BALB/c strain, C57BL/6 strain, C3H strain, and MRL strain, 60 mice in total, were immunized therewith twice a week, 6 to 8 times in total. On day 3 after the final administration, the spleens or the lymph nodes were extracted from the immunized mice, and lymphocytes were collected from the inside of the tissues. The collected lymphocytes were mixed with a mouse myeloma cell line P3U1, and washed with an RPMI medium (Sigma-Aldrich Co.) twice. To the cell precipitate, an equal amount of polyethylene glycol 4000 solution (Wako Pure Chemical Industries, Ltd.) diluted by 50% with RPMI was added. After pipetting of the cell suspension for 1 minute, the cells were washed with a 20-fold amount of RPMI 3 times. Thereafter, the cells were suspended in an RPMI medium containing 15% bovine serum (Equitech-Bio, Inc.), 2% HAT (Invitrogen Corporation), a 1/100 amount of a BM medium (Roche Ltd.), and penicillin and streptomycin at a final concentration of 5 ng/mL. The resultant was seeded in a 96-well plate and subjected to static culturing in a $CO_2$ incubator at 37° C. On day 5 from the seeding, the culture solution was replaced with a fresh medium, and the culturing was continued for another 5 days.

(3) Antibody Screening 1: Antigen Solid Phase ELISA

On day 10 from the seeding, culture supernatants were collected from wells in which the number of hybridomas was increased, Enzyme-Linked Immuno Sorbent Assay (hereinafter, referred to as ELISA) was carried out using a 96-well plate on which the antigen proTGF-α-hFc for screening was immobilized in an amount of 0.2 μg/well. As the color was developed in the ELISA, a supernatant having an OD value (absorbance at 450 nm/620 nm) of 0.2-0.5 or higher was determined as primary positive, and 1,007 types of hybridomas were selected. The positive hybridomas were transferred to 24-well plates, and cultured for another 3 days.

(4) Antibody Screening 2: Flow Cytometry

Using TGF-α/293T cells that were 293T cells transiently expressing full-length TGF-α, a flow cytometry analysis was carried out with the supernatant of the aforementioned 24-well plates by the following method. With 50 μL of the hybridoma supernatant per sample, $1 \times 10^5$ cells of the TGF-α/293T were reacted at 4° C. for 60 minutes. The cells were washed with PBS containing 2 mM EDTA and 0.5% BSA, and then reacted with a PE-labeled anti-mouse IgG antibody (MBL CO., LTD.) at 4° C. for 30 minutes. Further, the cells were washed by centrifugation at 400×g. Subsequently, the cell precipitate was suspended in 500 μL of PBS containing 2 mM EDTA and 0.5% BSA, and analyzed by flow cytometry (FC500, Beckman Coulter, Inc.).

(5) Antibody Screening 3: Immunoprecipitation Method

Figure 4:
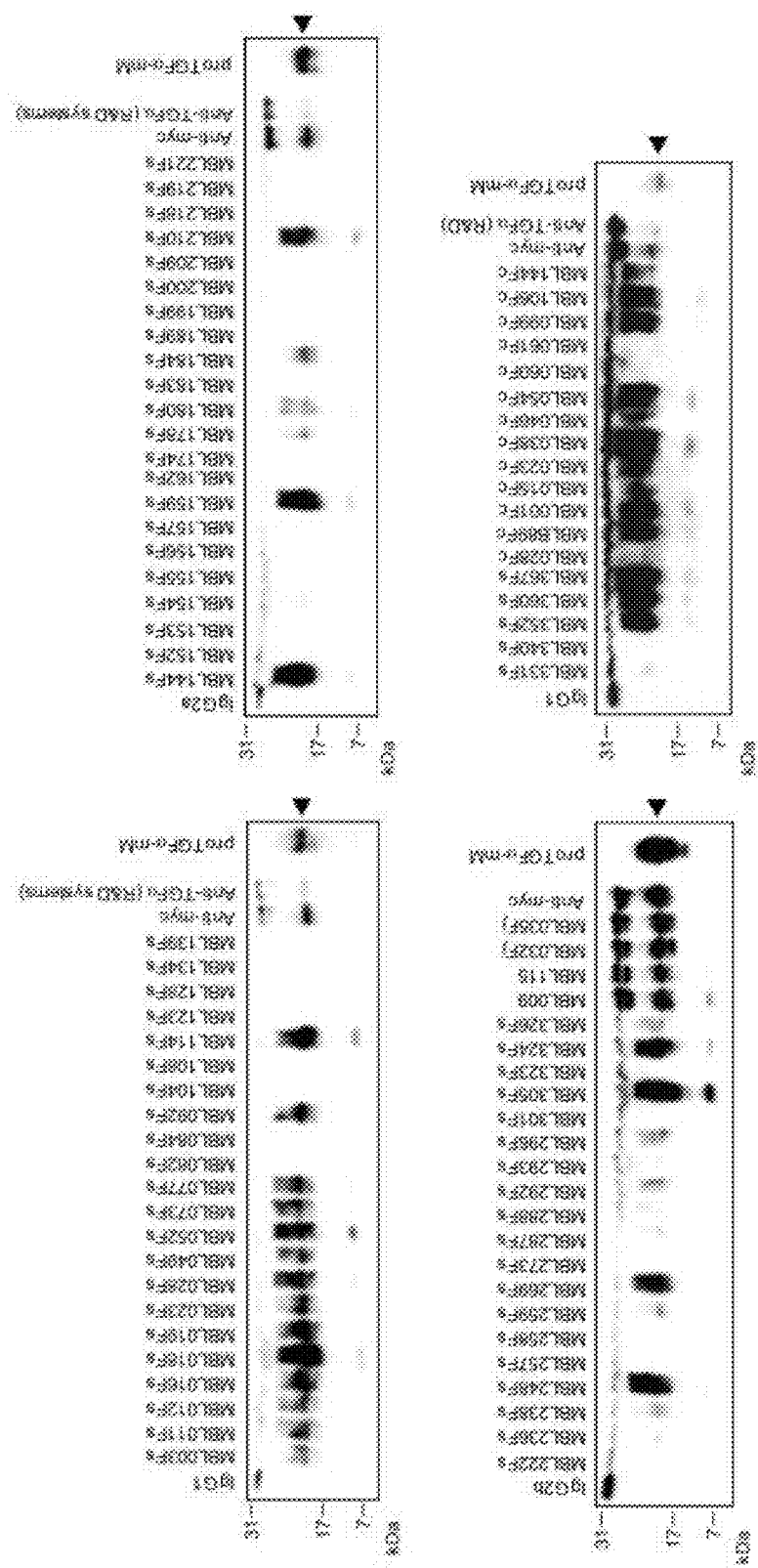
FIG. 4 shows photographs for illustrating the result of detecting, by an immunoprecipitation method, the reactivity of each anti-TGF-α antibody candidate (hybridoma supernatant) with the proTGF-α-mH antigen. In the detection of the immunoprecipitated antigen, an anti-myc tag antibody was used. In order to confirm that a detected band is of proTGF-α-mH, proTGF-α-mH is spread on the right-side end of a lane of a gel.

The hybridoma supernatant having shown reactivity with transmembrane TGF-α in the flow cytometry was then subjected to immunoprecipitation with proTGF-α-mH as the antigen by the following method. Per one hybridoma, 700 μL of the culture supernatant was collected, and 15 μL of protein G sepharose (GE Company) was added thereto, and allowed for reaction overnight with stirring at 4° C. To a sepharose precipitate obtained by washing the sepharose with PBS four times, 1 mL of proTGF-α-mH having a concentration of 3 μg/mL was added, and further allowed for reaction overnight with stirring at 4° C. To the sepharose precipitate obtained after the PBS washing, an SDS sample buffer solution was added in an equal amount to the precipitate, followed by boiling for 10 minutes to obtain the supernatant. Each 15-μL supernatant was applied to a 15%-SDS electrophoresis gel. As positive control antibodies of the immunoprecipitation, commercially-available anti-myc antibody (MBL CO., LTD.) and anti-TGF-α polyclonal antibody (R&D systems Inc.) were used. Moreover, as a positive control of immunoblotting, proTGF-α-mH was simultaneously applied. SDS electrophoresis was carried out, and proteins were transferred onto a PVDF membrane. Then, a blocking treatment was performed on the membrane using PBS containing 5% skim milk at room temperature for 1 hour. As a detection, a 500-fold diluted anti-myc antibody (MBL CO., LTD.) was used, and allowed to react with the PVDF membrane for 1 hour at room temperature. After the membrane was washed with PBS containing 0.05% Tween 20 (hereinafter referred to as washing solution), target bands were detected using a commercially-available chemiluminescent substrate (Millipore Corporation) (FIG. 4).

Figure 2:
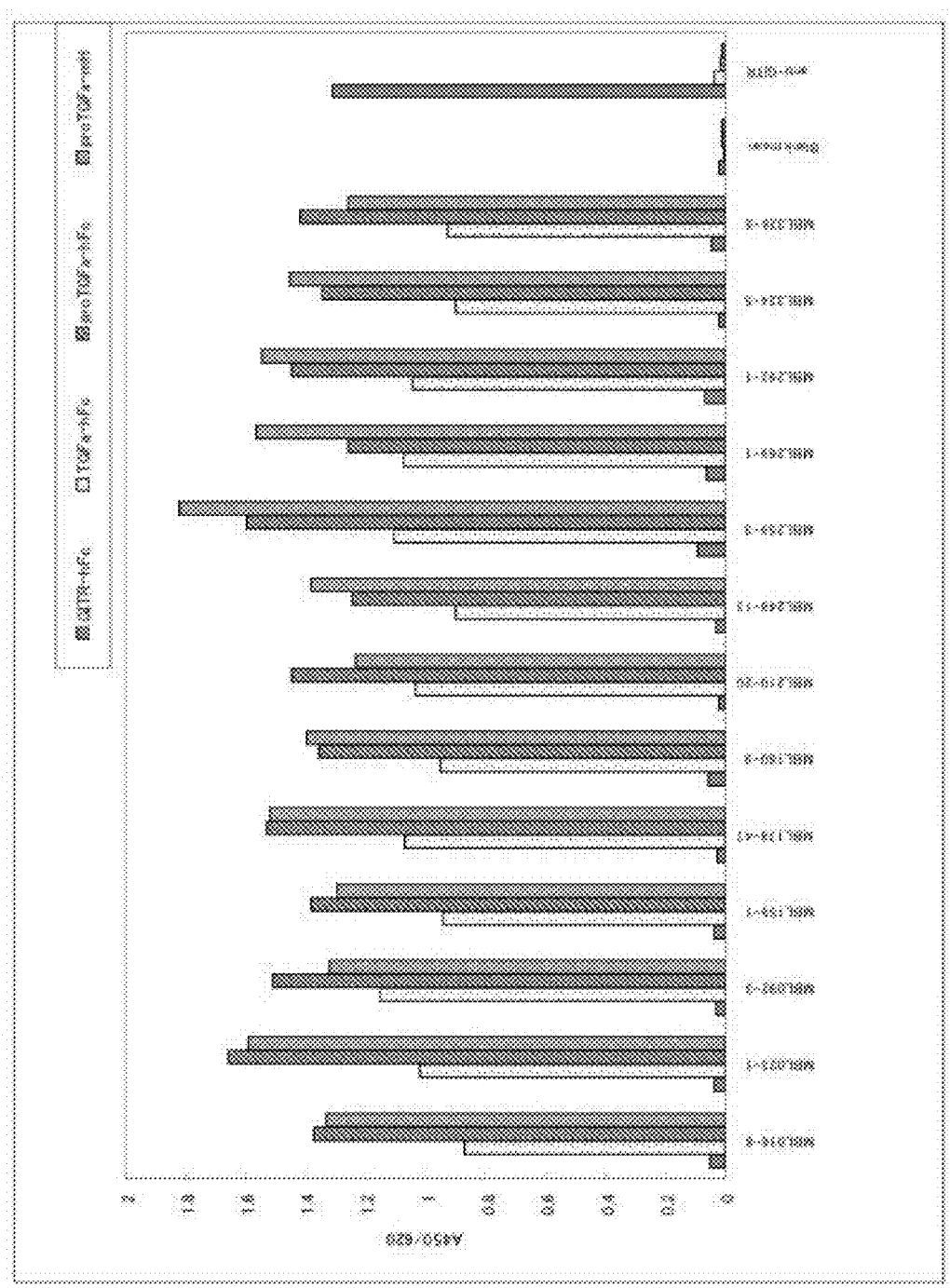
FIG. 2 is a graph showing examples of the reactivity of each anti-TGF-α antibody candidate (purified and labeled with biotin) in solid phase ELISA using the immunogens and the antigens for screening. Shown is the result of detecting the reactivity of each anti-TGF-α antibody (purified and labeled with biotin) with four antigens in ELISA. The absorbances at 450 nm/620 nm (the vertical axis, OD value) of GITR-hFc, TGF-α-hFc, proTGF-α-hFc, and proTGF-α-mH are shown in the graph and arranged in this order from the left.
Figure 3:
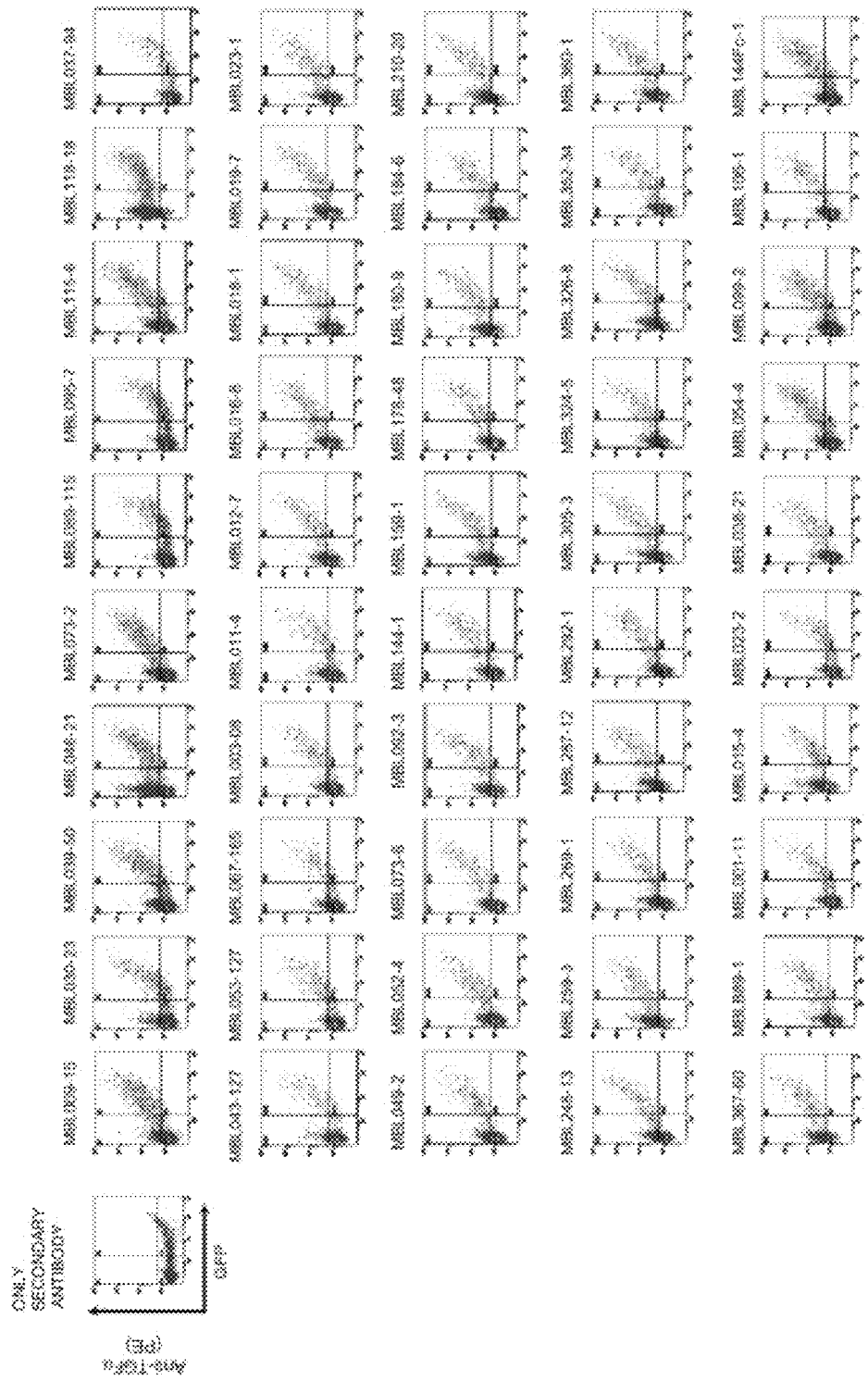
FIG. 3 shows graphs for illustrating examples of the result of analyzing, by flow cytometry, the reactivity of each anti-TGF-α antibody candidate (purified antibody) with 293T cells forced to express transmembrane TGF-α. Fluorescence by GFP was spread along the X axis, while fluorescence by the anti-TGF-α antibodies and a PE-labeled anti-mouse IgG antibody was spread along the Y axis. If the antibodies react with transmembrane TGF-α, the dots are shifted to the upper right in comparison with the negative control.

From the results of antigen solid phase ELISA, flow cytometry and immunoprecipitation, the hybridoma supernatant was selected, and monoclones were produced from the hybridomas by a limiting dilution method. To check the reactivity between the purified antibodies and TGF-α, FIG. 2 illustrates part of data for examining the reactivity of the purified antibodies (labeled with biotin) using ELISA plates on which GITR-hFc, TGF-α-hFc, proTGF-α-hFc, and proTGF-α-mH were respectively immobilized (in an amount of 0.2 μg/well). It was observed that the purified antibodies did not react with the negative control GITR-hFc at the OD value of 0.1 or higher, but reacted with TGF-α-hFc, proTGF-α-hFc, and proTGF-α-mH at the OD value of 0.5 or higher. FIG. 3 shows the result of checking the reactivity of the purified antibodies with the TGF-α/293T cells by flow cytometry. The isotype of each antibody was determined using IsoStrip Kit (Roche Ltd.). As a result, 39 types of single antibodies produced by the hybridomas were listed as anti-TGF-α monoclonal antibodies, and used for the subsequent experiments (Table 1).

TABLE 1

| Clone name of anti-TGF-α antibody | Isotype mouse | | Immunogen | Solid phase ELISA proTGFα-hFc | Solid phase ELISA TGFα-hFc | IP proTGFα-mH | FCM TGFα/293T |
|---|---|---|---|---|---|---|---|
| MBL009-15 | IgG1 | κ | proTGFα-mFc | 1.508 | 0.879 | ++ | +++ |
| MBL030-23 | IgG1 | κ | proTGFα-mFc | 1.167 | 0.952 | + | + |
| MBL039-60 | IgG2b | κ | proTGFα-mFc | 1.403 | 0.435 | + | ++ |
| MBL046-21 | IgG1 | κ | proTGFα-mFc | 1.026 | 1.041 | + | + |
| MBL073-2 | IgG1 | κ | proTGFα-mFc | 1.55 | 0.878 | + | +++ |
| MBL095-7 | IgG3 | κ | proTGFα-mFc | 1.337 | 0.824 | + | + |
| MBL115-6 | IgG2b | κ | proTGFα-mFc | 1.476 | 0.859 | ++ | ++ |
| MBL118-18 | IgG1 | κ | proTGFα-mFc | 0.91 | 0.419 | + | ++ |
| MBL032-10 | IgG1 | κ | proTGFα-mFc | 1.693 | 0.737 | ++ | +++ |
| MBL035-73 | IgG1 | κ | proTGFα-mFc | 1.596 | 0.622 | ++ | +++ |
| MBL043-127 | IgG1 | κ | proTGFα-mFc | 0.947 | 0.538 | + | + |

TABLE 1-continued

| Clone name of anti-TGF-α antibody | Isotype mouse | | Immunogen | Solid phase ELISA proTGFα-hFc | Solid phase ELISA TGFα-hFc | IP proTGFα-mH | FCM TGFα/293T |
|---|---|---|---|---|---|---|---|
| MBL003-8 | IgG1 | κ | proTGFα-mFc + proTGFα-mH | 1.122 | 0.561 | ++ | ++ |
| MBL016-8 | IgG2a | κ | proTGFα-mFc + proTGFα-mH | 1.373 | 0.869 | ++ | ++ |
| MBL018-1 | IgG1 | κ | proTGFα-mFc + proTGFα-mH | 1.509 | 0.703 | +++ | ++ |
| MBL019-7 | IgG1 | κ | proTGFα-mFc + proTGFα-mH | 1.018 | 0.404 | ++ | ++ |
| MBL023-1 | IgG1 | κ | proTGFα-mFc + proTGFα-mH | 1.657 | 1.017 | ++ | ++ |
| MBL052-4 | IgG1 | κ | proTGFα-mFc + proTGFα-mH | 1.453 | 0.702 | +++ | ++ |
| MBL073-6 | IgG1 | κ | proTGFα-mFc + proTGFα-mH | 1.114 | 0.427 | ++ | ++ |
| MBL092-3 | IgG2a | κ | proTGFα-mFc + proTGFα-mH | 1.511 | 1.15 | ++ | ++ |
| MBL144-1 | IgG1 | κ | proTGFα-mFc + proTGFα-mH | 1.422 | 0.65 | +++ | ++ |
| MBL159-1 | IgG1 | κ | proTGFα-mFc + proTGFα-mH | 1.379 | 0.939 | +++ | ++ |
| MBL178-47 | IgG1 | κ | proTGFα-mFc + proTGFα-mH | 1.528 | 1.07 | ++ | ++ |
| MBL180-9 | IgG1 | κ | proTGFα-mFc + proTGFα-mH | 1.358 | 0.952 | ++ | +++ |
| MBL184-6 | IgG1 | κ | proTGFα-mFc + proTGFα-mH | 1.396 | 0.745 | ++ | ++ |
| MBL210-20 | IgG1 | κ | proTGFα-mFc + proTGFα-mH | 1.448 | 1.033 | +++ | +++ |
| MBL248-13 | IgG1 | κ | proTGFα-mFc + proTGFα-mH | 1.242 | 0.902 | +++ | +++ |
| MBL259-3 | IgG2a | κ | proTGFα-mFc + proTGFα-mH | 1.594 | 1.106 | ++ | +++ |
| MBL269-1 | IgG1 | κ | proTGFα-mFc + proTGFα-mH | 1.259 | 1.076 | +++ | ++ |
| MBL287-12 | IgG1 | κ | proTGFα-mFc + proTGFα-mH | 1.131 | 0.906 | ++ | +++ |
| MBL292-1 | IgG1 | κ | proTGFα-mFc + proTGFα-mH | 1.45 | 1.044 | ++ | ++ |
| MBL305-3 | IgG1 | κ | proTGFα-mFc + proTGFα-mH | 1.25 | 0.951 | +++ | ++ |
| MBL324-5 | IgG1 | κ | proTGFα-mFc + proTGFα-mH | 1.346 | 0.9 | +++ | +++ |
| MBL326-8 | IgG1 | κ | proTGFα-mFc + proTGFα-mH | 1.418 | 0.927 | ++ | ++ |
| MBL352-34 | IgG1 | κ | proTGFα-mFc + proTGFα-mH | 1.349 | 0.704 | +++ | ++ |
| MBL360-1 | IgG1 | κ | proTGFα-mFc + proTGFα-mH | 1.234 | 0.96 | +++ | ++ |
| MBL367-60 | IgG1 | κ | proTGFα-mFc + proTGFα-mH | 1.19 | 0.936 | +++ | +++ |
| MBLB89-1 | IgG1 | κ | proTGFα-mFc + proTGFα-mH | 1.443 | 0.614 | +++ | ++ |
| MBL015-4 | IgG1 | κ | proTGFα-mFc + proTGFα-mH | 0.806 | 0.699 | ++ | ++ |
| MBL054-4 | IgG1 | κ | proTGFα-mFc + proTGFα-mH | 1.289 | 0.707 | +++ | ++ |

2. Selection of Anti-TGF-α Antibodies Inhibiting EGFR Tyrosine Phosphorylation (1) Western Blotting Using Anti-Tyrosine Phosphorylation EGFR Antibodies Using an EGFR-overexpressing human squamous cell carcinoma cell line A431, anti-TGF-α antibodies which inhibited TGF-α-stimulated EGFR tyrosine phosphorylation were searched for by the following method. The A431 cells were cultured in a OMEN medium containing 10% bovine serum. Two days before the assay, $1 \times 10^5$ cells were seeded per well in 24-well plates. On the day before the assay, the supernatant was eliminated, and the cell surface was washed once with DMEM not supplemented with a serum, and the same serum-free medium was added by 500 μL per well. On the day of the assay, DMEM containing 20 ng/mL of commercially-available secreted TGF-α biosynthesized by *Escherichia coli* (R&D systems Inc.) was prepared. To this, 39 types of anti-TGF-α antibodies or anti-EGFR antibody (clone 225: the original antibody of cetuximab, Calbiochem) were added in an amount twice the concentration shown in FIG. 5, and allowed for reaction at 4° C. for 1 hour with stirring. Thereafter, each 500-μL amount was added to the A431 cell-culture well. After 30 minutes, the supernatant was eliminated, and 150 μL of an SDS sample buffer solution was immediately added. After stirring by pipetting, the mixture was transferred to a 1.5-mL tube, and subjected to a boiling treatment for 5 minutes. After centrifugation, the supernatant was collected. Subsequently, each 15-μL sample was added to a 7.5%-SDS electrophoresis gel, and subjected to electrophoresis. After proteins were transferred onto a PVDF membrane, the membrane was subjected to blocking with PBS containing 5% BSA (hereinafter referred to as blocking solution) at 4° C. overnight. The membrane was washed with a washing solution, and then allowed to react at room temperature for 1 hour with anti-tyrosine phosphorylation EGFR (P-Tyr1173) antibody (9H2) 200-fold diluted with a blocking solution. The membrane was washed with a washing solution, and then allowed to react at room temperature for 1 hour with a POD-labeled anti-mouse IgG antibody (MBL CO., LTD.) 5,000-fold diluted with a blocking solution. After the membrane was washed with a washing solution, target bands were detected using a commercially-available chemiluminescent substrate (Millipore Corporation), and image data were recorded using LAS-3000.

(2) Re-Blotting with Anti-EGFR Antibody

Subsequently, in order to remove the antibodies from the PVDF membrane thus used, the membrane was treated with distilled water containing 0.2% NaOH at room temperature for 5 minutes, and then promptly washed with a washing solution. Using PBS(–) containing 5% skim milk (Snow Brand Milk Products Co., Ltd.), blocking was performed at 4° C. overnight, and allowed to react with an anti-EGFR antibody (MBL CO., LTD.) at room temperature for 1 hour. The membrane was washed, and then allowed to react at room temperature for 1 hour with a POD-labeled anti-mouse IgG antibody (MBL CO., LTD.) 5,000-fold diluted with a blocking solution. After washing, bands derived from EGFR were detected using a commercially-available chemiluminescent substrate (Millipore Corporation) (FIG. 5).

3. Flow Cytometry Analysis on Established Cancer Cells Using Anti-TGF-αAntibody MBL259-3

In a flow cytometry analysis using 293T cells forced to express TGF-α, an anti-TGF-α antibody MBL259-3 observed to have relatively strong reactivity was used to carry out flow cytometry on each established cancer cell as follows. A colorectal cancer-derived cell line SW620 (K-Ras G12V, homo mutation) and a lung cancer-derived cell line A427 (K-Ras G12D, hetero mutation) were subcultured on 10-cm plates using a L15 liquid medium (Invitrogen Corporation) containing 10% bovine serum and a MEM medium (Invitrogen Corporation) containing 10% bovine serum, respectively. When the cell density reached a 70 to 80% confluent stage, the supernatant was eliminated, and the cell surface was washed with 10 mL of PBS. Thereafter, in order to detach the cells from the plate, 3 mL of 5 mM EDTA/PBS was added, followed by a treatment in a $CO_2$ incubator at 37° C. for 5 minutes. After 7 mL of PBS was additionally added, the cells were thoroughly suspended with a 10-mL pipette. The resulting cell suspension was transferred to a 15-cc centrifugal tube (BID Falcon) while passed through a 70-μm cell strainer (BD Falcon). After centrifugation at 400×g for 3 minutes, the supernatant was discarded. The resultant was re-suspended in 5 mL of PBS. The cell suspension was dispensed in a 50- to 100-μL capacity tube, and human IgG (MBL CO., LTD.) was added thereto to bring the final concentration to 100 μg/mL. The mixture was left standing at 4° C. for 15 minutes. After centrifugation at 400×g for 2 minutes, the supernatant was discarded. Then, the anti-TGF-α antibody MBL259-3 having a final concentration of 10 μg/mL or isotype control mouse IgG was added and allowed for reaction at 4° C. for 1 hour. After the cells were washed with PBS containing 0.5% BSA and 2 mM EDTA twice, a PE fluorescence-labeled anti-mouse IgG antibody (MBL CO., LTD.) 200-fold diluted with a washing solution was allowed to react therewith at 4° C. for 1 hour. After washing with a washing solution at 400×g for 2 minutes 3 times, the cells was suspended in 500 μL of a washing solution, and subjected to a flow cytometry analysis with FC500 (Beckman Coulter, Inc.) (FIG. 6).

Figure 7A:
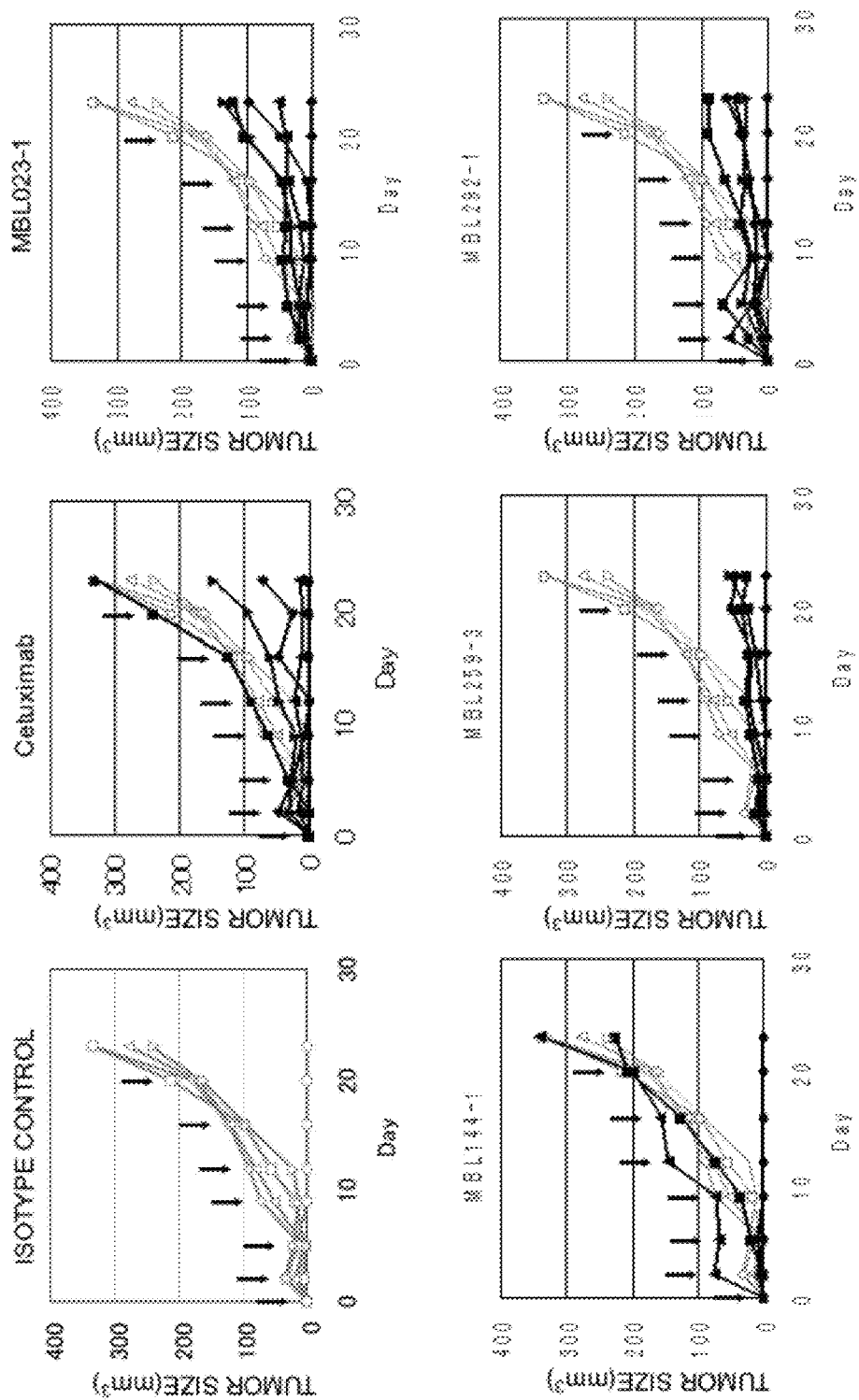
FIG. 7a shows graphs for illustrating the result of detecting the anti-tumor activity of each anti-TGF-α antibody in a cancer-bearing mouse model having a lung cancer cell line A427 transplanted. As a control, an EGFR blocking antibody cetuximab was used. The X axis represents the day from the antibody administration, and the Y axis represents the tumor volume, mm$^3$. The experiment was conducted using 5 mice, and the change in the tumor size of all the mice was plotted on the graphs. In the graphs, the grey lines show the result of administering an isotype control, and the black lines show the result of administering each anti-TGF-α antibody and cetuximab.
Figure 7B:
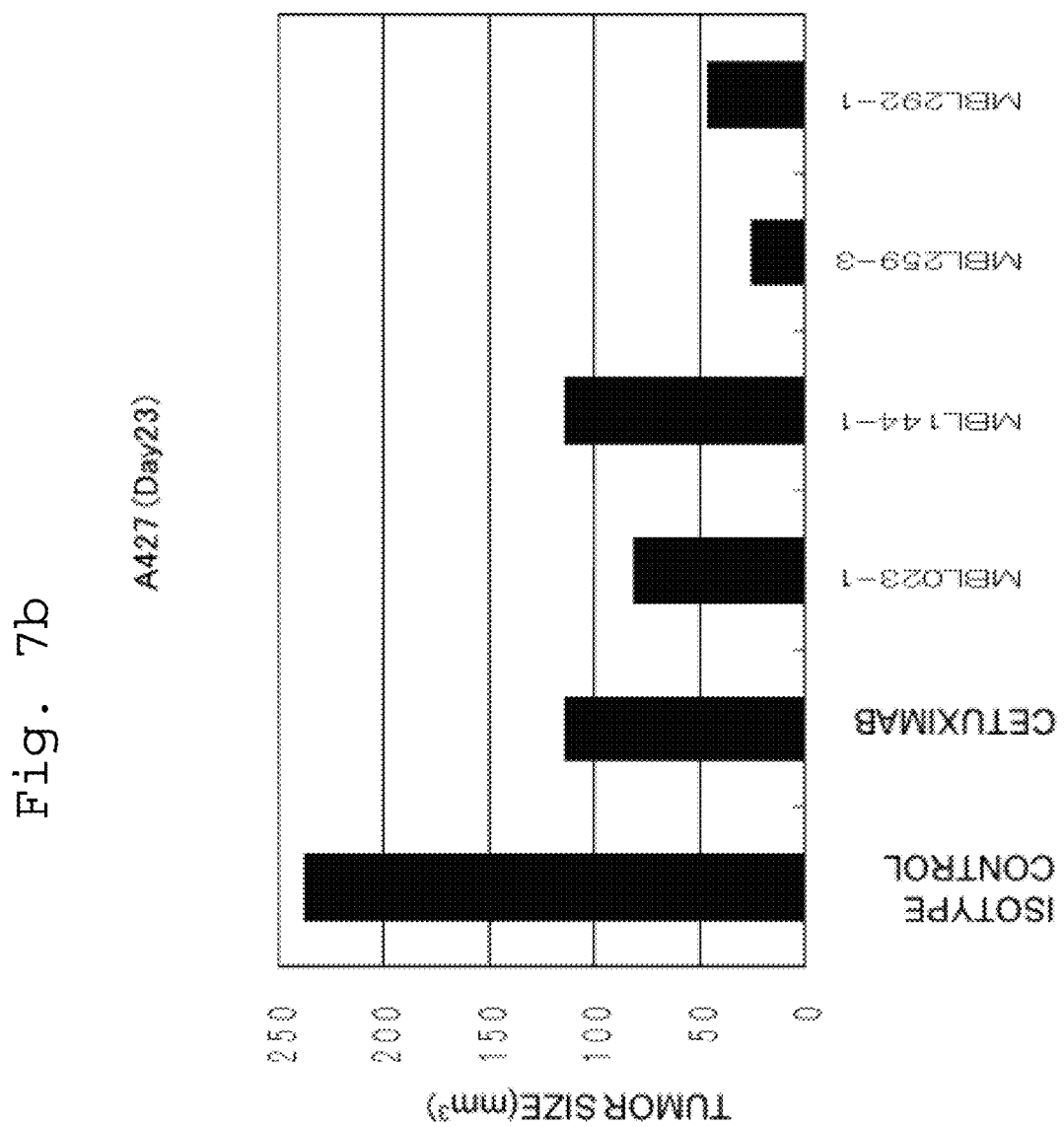
FIG. 7b shows a graph for illustrating the result of detecting the anti-tumor activity of each anti-TGF-α antibody in the cancer-bearing mouse model having the lung cancer cell line A427 transplanted. As the control, the EGFR blocking antibody cetuximab was used. The X axis represents the day from the antibody administration, and the Y axis represents the tumor volume, mm$^3$. The graph shows the average values of the tumor size (average of 5 mice) on day 23 from the antibody administration.
Figure 8A:
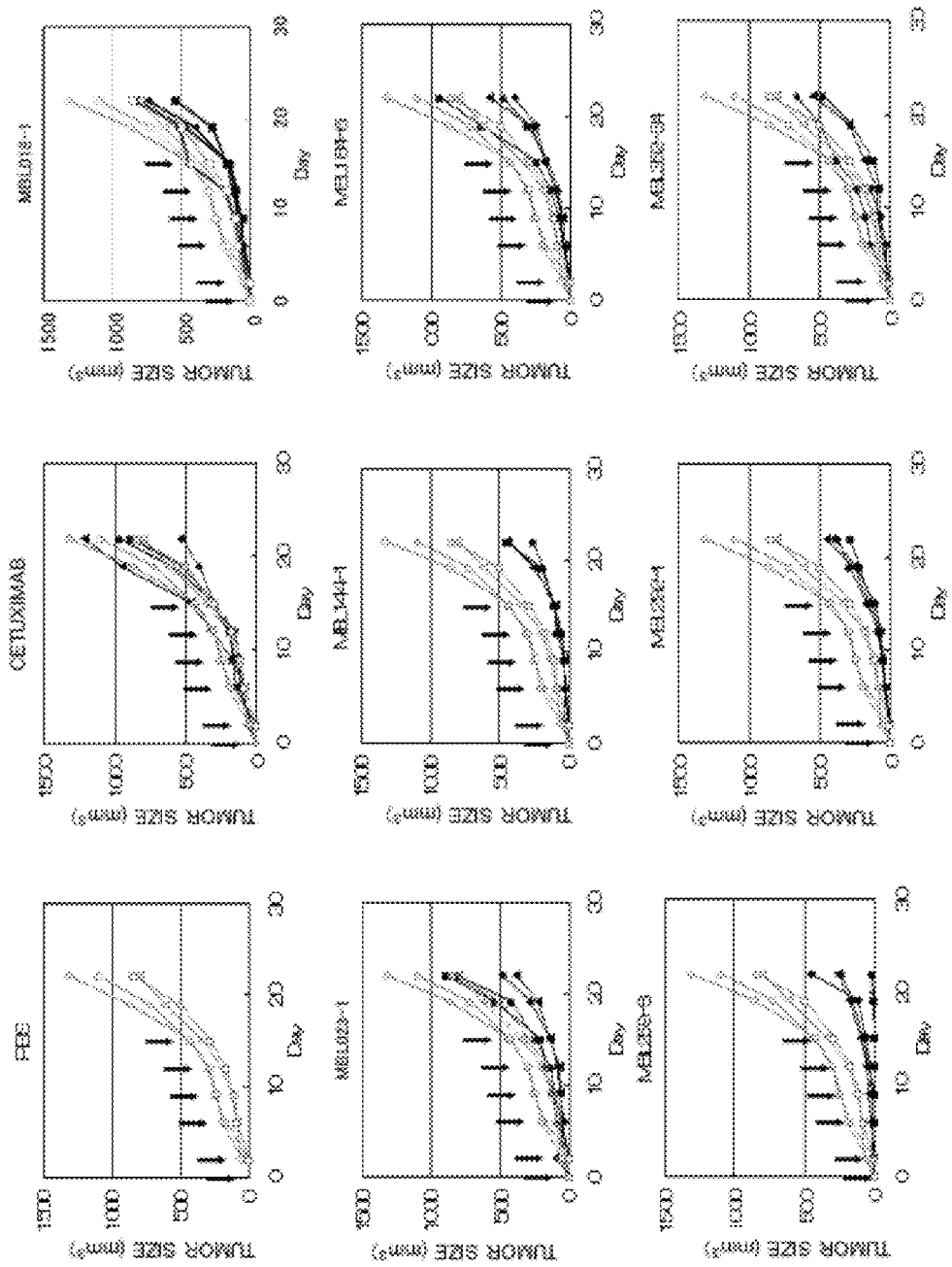
FIG. 8a shows graphs for illustrating the anti-tumor activity of each anti-TGF-α antibody in a cancer-bearing mouse model having a colorectal cancer cell line SW620 transplanted. As a control, the EGFR blocking antibody cetuximab was used. The X axis represents the day from the administration, and the Y axis represents the tumor volume, mm$^3$. The experiment was conducted using 4 mice, and the change in the tumor size of all the mice was plotted on the graphs. In the graphs, the gray lines show the result of administering PBS (−), and the black lines show the result of administering each anti-TGF-α antibody and cetuximab.
Figure 8B:
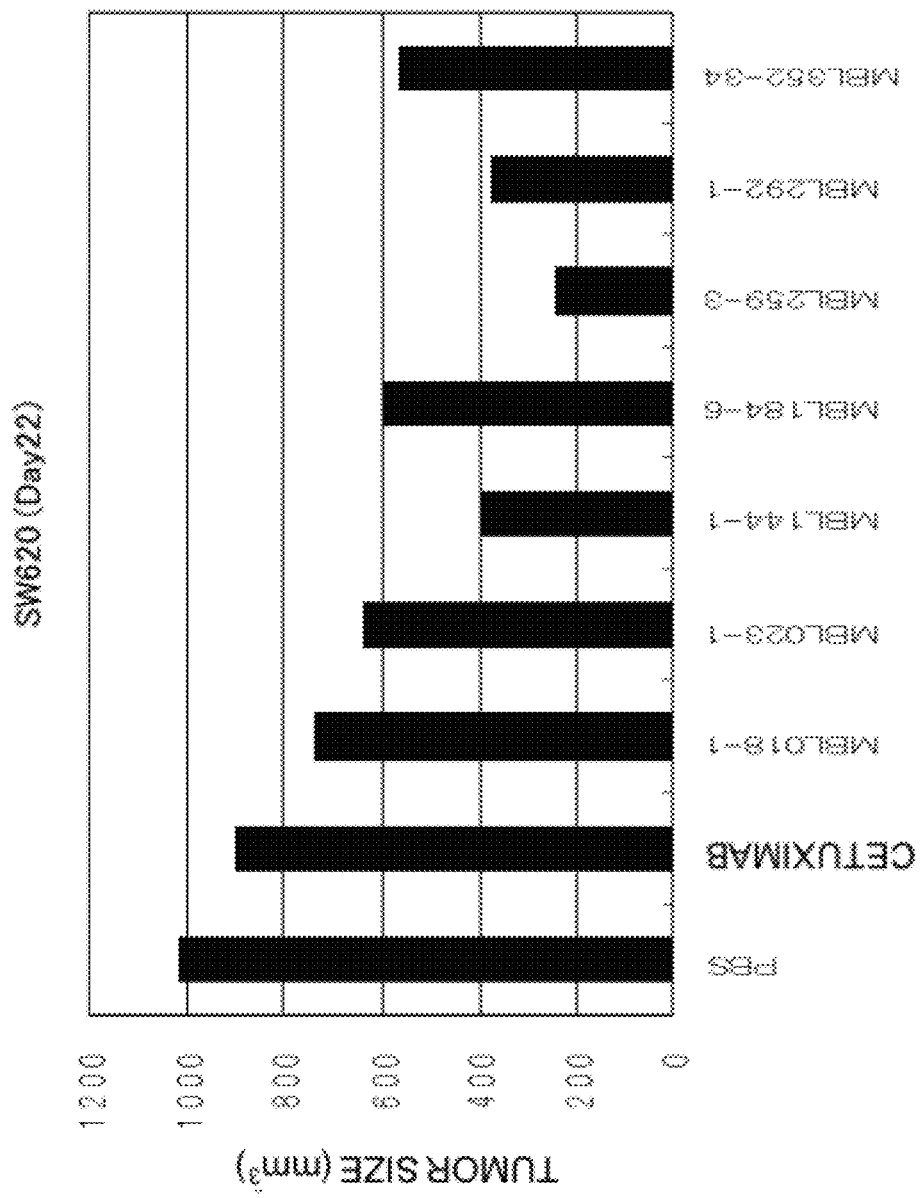
FIG. 8b shows the anti-tumor activity of each anti-TGF-α antibody in the cancer-bearing mouse model having the colorectal cancer cell line SW620 transplanted. As the control, the EGFR blocking antibody cetuximab was used. The X axis represents the day from the administration, and the Y axis represents the tumor volume, mm$^3$. The graph shows the average values of the tumor size (average of four mice) on day 22 from the antibody administration.

4. Tumor-Suppressing Effect of Anti-TGF-α Antibodies in Cancer-Bearing Mouse Model Having Ras Mutated Cancer Transplanted SW620 (K-Ras gene G12V, homo mutation) and A427 (K-Ras gene G12D, hetero mutation) cells used for transplantation were subcultured by the above-described method, and suspended in PBS(−) containing various anti-TGF-α antibodies (3 mg/mL) or cetuximab (Merck KGaA) to 5×10$^7$ cells/mL. Using a 1-mL syringe with a 23G needle (Terumo Corporation), the cancer cells were subcutaneously transplanted into the right dorsal part of 4-week old female BALB/c nude mice (Japan SLC, Inc.) by 100 μL/mouse. Thereafter, each of the anti-TGF-α antibodies and cetuximab were directly administered into the cancer tissues, respectively, twice a week by 300 μg/mouse (100 to 200 μL/mouse) using a 1-mL syringe with a 26G needle 6 or 7 times in total. As a negative control, PBS(−) or mouse IgG2a was used. In measuring the tumor size, two or three measurers individually measured the long axis and the short axis of the cancer with a vernier caliper every time before the agent was administered. The tumor volume was calculated by "tumor volume (mm$^3$)=long axis (mm)×short axis (mm)$^2$×π/6." The averages of the calculated values by the measurers were plotted on graphs (FIGS. 7, 8).

Figure 9:
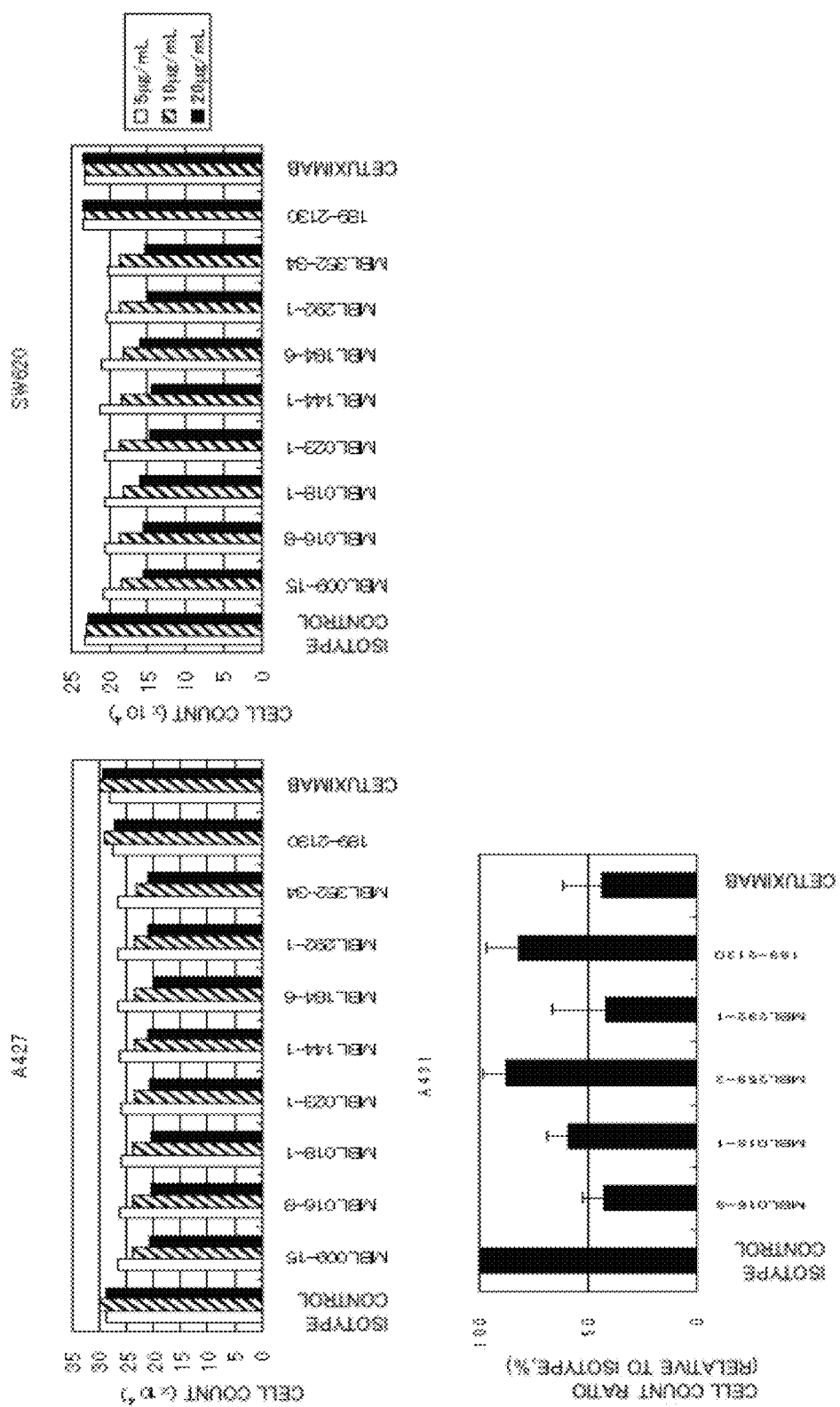
FIG. 9 shows graphs for illustrating the growth-inhibiting effect of each anti-TGF-α antibody on cancer cells in a three-dimensional cell culture system. As the cancer cells, A427 and SW620 were used, on which a tumor-suppressing effect of the antibody of the present invention was observed in the in vivo test. Moreover, the EGFR-overexpressing cell line A431 was used as a positive control to confirm the effect of cetuximab.

5. Growth-Inhibiting Effect of Anti-TGF-α Antibodies on Various Cancer Cells in Three-Dimensional Culture System Various cancer cells were three-dimensionally cultured using commercially-available 3D Culture BME Cell Proliferation Assay (Trevigen Inc.) by the following method. BME (Basement membrane extract) was dispensed in a 96-well plate by 35 μL/well. Then, in order to completely eliminate air bubbles, a centrifugal operation at 800×g at 4° C. was performed for 10 minutes. After it was visually checked that the BME was spreading all over the wells uniformly, the BME gel was formed by incubation at 37° C. in a 5%-CO$_2$ environment for 1 hour. Various cancer cells (SW620, A427, and A431) were detached from the plates by treatment using PBS(−) containing 5 mM EDTA, washed with PBS twice, and then suspended in a liquid medium containing 2%-BME at 1×10$^5$ cells/mL. The cell suspension was seeded onto the BME gel by 100 μL/well. The cells were colonized on the gel by culturing at 37° C. in a 5%-CO$_2$ environment. Thereafter, an anti-TGF-α antibody solution or cetuximab was added by 100 μL/well to bring the final concentration to 50 μg/mL. As a negative control, isotype mouse IgG2a was used. After culturing for 80 hours from the antibody addition, 3D Culture Cell Proliferation Reagent was added by 15 μL/well and allowed for reaction for 3 hours. Thereafter, the absorbance at 450 nm/620 nm was measured with a plate reader (Ultramark, Bio-Rad Laboratories, Inc.) (FIG. 9).

6. Angiogenesis-Inhibiting Effect of Anti-TGF-α Antibodies in Angiogenesis Evaluation System in Mouse Hypodermis An angiogenesis evaluation system in a mouse hypodermis was carried out using commercially-available Directed In Vivo Angiogenesis Assay (Trevigen Inc.) by the following method. Growth Factor Reduced BME (GFR-BME) thawed on ice was mixed with commercially-available human TGF-α (R&D systems Inc., 20 ng/angioreactor), a heparin solution (1 μL/angioreactor), and an anti-TGF-α antibody (6.25 μg/angioreactor). In this event, PBS(−) was used for correction, so that the total volume of the added materials was 10% of the BME. As a negative control, BME to which PBS(−) was added by 10% was used. Moreover, as a positive control of the experimental system, used was BME to which angiogenesis-inducing factors VEGF (12.5 ng/angioreactor) and FGF-2 (37.5 ng/angioreactor) were added and to which an anti-VEGF antibody bevacizumab (trade name Avastin: Roche Ltd.) was further added by 2.5 μg or 12.5 μg/angioreactor. The above-described mixture solution was poured into silicone tubes (angioreactors) by 20 μL per tube, and left standing for reaction at 37° C. under 5% CO$_2$ for 1 hour, and the BME gel was formed.

Figure 10:
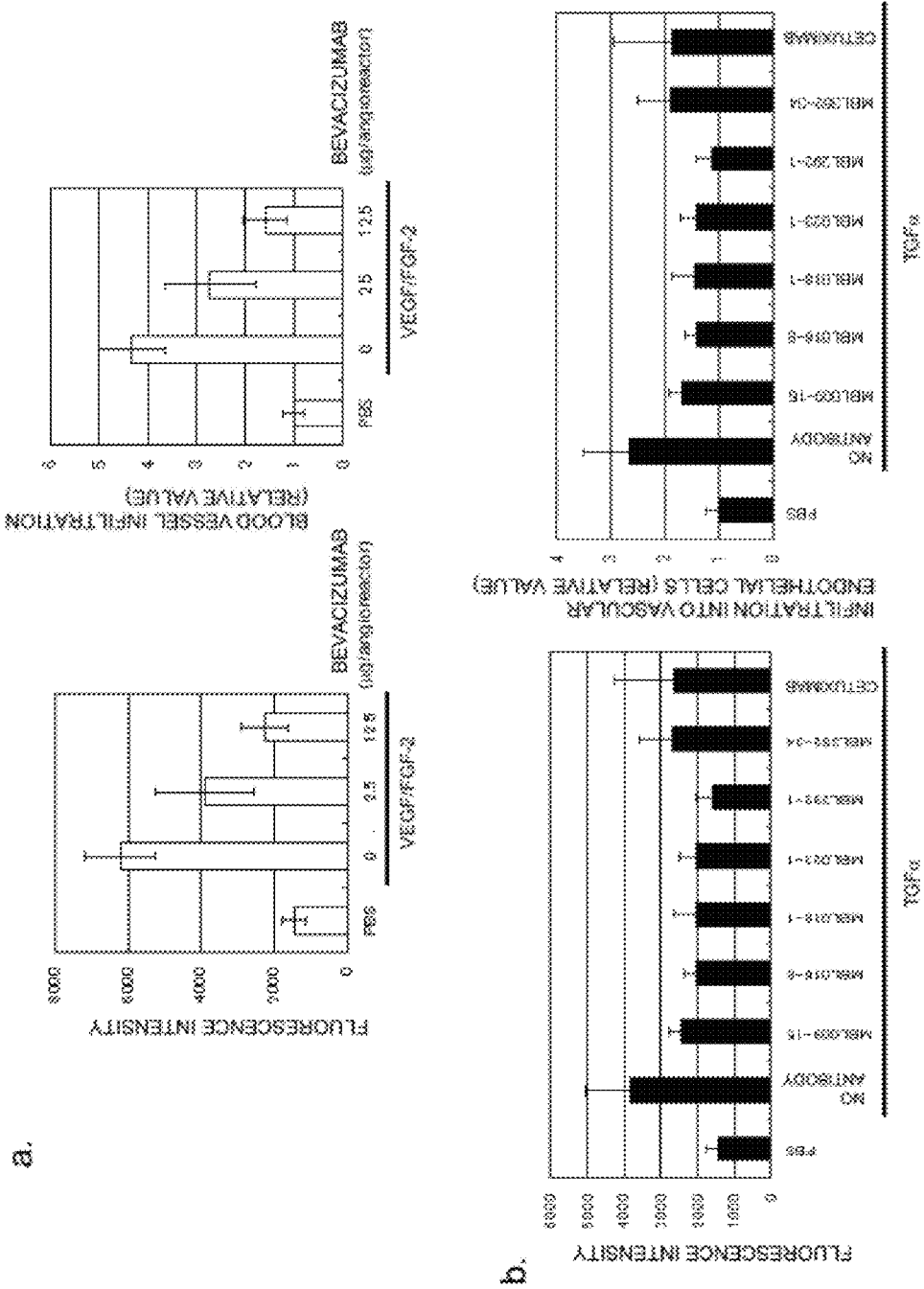
FIG. 10 shows graphs for illustrating the inhibition effect of each anti-TGF-α antibody in an angiogenesis evaluation system utilizing a mouse hypodermis. (a) A mixture solution of VEGF and FGF-2 was used as a positive control of an angiogenesis-inducing factor. Moreover, a VEGF blocking antibody bevacizumab was used as a positive control of an angiogenesis inhibiting antibody. Shown were fluorescence intensity indicating infiltration into vascular endothelial cells (left) and relative values with 1 being the fluorescence intensity when PBS was added (right). (b) The angiogenesis inhibiting ability of various antibodies was examined in the presence of TGF-α. Shown were fluorescence intensity indicating infiltration into vascular endothelial cells (left) and relative values with 1 being the fluorescence intensity when PBS was added (right).

For anesthesia, 1 mg of pentobarbital (Schering-Plough Corporation) was intraperitoneally injected into 7-week old female BALB/c nude mice. Angioreactors were subcutaneously inserted into dorsal flanks, two in one dorsal flank, a total of four per mouse. The skin was sutured with AUTO-CLIP 9 mm (BD Co.). After nurturing for 15 days, the nude mice were euthanized by diethyl ether inhalation, and the implanted angioreactors were extracted. The open end of each angioreactor and the opposite end were cut apart with a scalpel, and a BME gel inside the angioreactor was collected into a sterilized 1.5-mL tube in an extruding manner. Further, the inside of the angioreactor was rinsed with 300 μL of CellSperse liquid, and the rinsing liquid was collected. The collected gel was incubated at 37° C. for 3 hours, followed by centrifugation at 250×g for 5 minutes. The cells having migrated into the reactor were collected as a precipitated fraction. The cell precipitate was suspended in 500 μL of a DMEM containing 10% FCS, and left standing at 37° C. for 1 hour. Thereafter, centrifugation at 250×g was performed at room temperature for 10 minutes, and the cells were washed. After the cells were further washed with Wash Buffer attached to the kit twice, 200 μL of FITC-Lectin was added to the precipitate for suspension, and allowed for reaction at 4° C. overnight. After washed with Wash Buffer 3 times, the cells were suspended in 100 μL of Wash Buffer, the fluorescence amount was measured with a fluorometer (Arvo, PerkinElmer Inc.) (excitation: 485 nm, emission: 510 nm). The data was represented by a relative value [(fluorescence intensity of each sample)/(average fluorescence intensity of negative control)]. The average value and standard deviation were calculated for each condition, and a statistical analysis was performed by Student's t-test (FIG. 10).

7. Immunohistostaining Method

Figure 11:
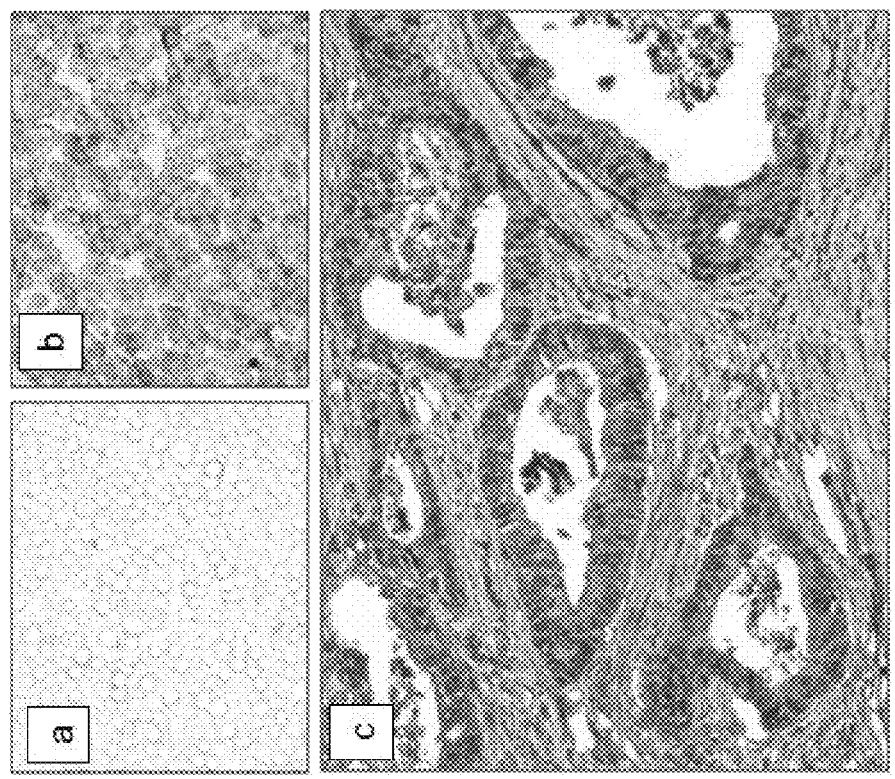
FIG. 11 shows photographs of immunohistostaining on the colorectal cancer cell line SW620 and colorectal cancer tissue section using the anti-TGF antibody MBL259-3. Shown are immunohistostaining images of K-Ras gene-homo mutated colorectal cancer cell line SW620 (embedded in paraffin) using the isotype control mouse IgG2a (a), and using the anti-TGF-α antibody MBL259-3 (b). An immunohistostaining image of the colorectal cancer (adenocarcinoma) patient-derived cancer tissue section (embedded in paraffin) using MBL259-3 is shown in (c).

A colorectal cancer-derived cell line SW620 (K-Ras G12V, homo mutation) was subcultured on a 10-cm plate using an L15 liquid medium (Invitrogen Corporation) containing 10% bovine serum. When the cell density reached a 70 to 80% confluent stage, the cell surface was washed with 10 mL of PBS once. After addition of 3 mL of 5 mM EDTA/PBS and a treatment in a CO$_2$ incubator at 37° C. for 5 minutes, 7 mL of PBS was additionally added, and the cells were thoroughly suspended with a 10-mL pipette. The resulting cell suspension was transferred to a 15-cc centrifugal tube (BD Falcon). After centrifugation at 400×g for 3 minutes, the supernatant was discarded. The cells were re-suspended in 5 mL of PBS. To this, 5 mL of a 8% formalin buffer solution was added, lightly stirred, and then left standing on ice for 1 hour. After centrifugation at 400×g for 3 minutes, the precipitated cell mass was washed with PBS once. Then, for the purpose of dehydration, the resultant was treated with 70% ethanol for 10 minutes twice, 80% ethanol for 10 minutes twice, 90% ethanol for 10 minutes once, 95% ethanol for 10 minutes once, 100% ethanol for 10 minutes twice, xylene for 10 minutes 3 times, xylene/paraffin for 10 minutes twice, and paraffin at 60° C. for 10 minutes 3 times. The prepared paraffin block was stored in a freezer at −30° C. until a staining test. After the cell mass paraffin block of SW620 was sliced to a thickness of 3 to 5 μm with a microtome, the obtained section was placed on a microscope slide. Meanwhile, a colorectal cancer patient-derived paraffin-embedded cancer tissue section was purchased from Shanghai Outdo Biotech Co., Ltd., China. For the paraffin removal treatment, the SW620 cell mass section and the colorectal cancer-derived tissue section were treated with xylene for 5 minutes 3 times, 100% ethanol for 5 minutes twice, 90% ethanol for 5 minutes once, 80% ethanol for 5 minutes once, 70% ethanol for 5 minutes once, and PBS for 5 minutes 3 times all at room temperature. Next, in order to activate the antigen, the sections were immersed in a 10 mM citrate buffer solution containing 0.05% Tween-20 at pH 6.0, and treated in an autoclave at 125° C. for 5 minutes. Next, in order to quench the endogenous peroxidase activity, the sections were treated with PBS containing 3% hydrogen peroxide at room temperature for 10 minutes, and then treated with PBS containing 5% normal rat serum and 0.5% BSA (blocking solution) at room temperature for 30 minutes. After the excessive solution was wiped with a cloth, the anti-TGF antibody MBL259-3 and an isotype control (mouse IgG2a, MBL CO., LTD.) diluted to 10 μg/mL with a blocking solution were added by appropriate amounts (enough to immerse the tissue sections therein), and allowed for reaction at room temperature for 2 hours. After washing with PBS containing 0.05% Tween-20 at room temperature for 5 minutes 3 times, a secondary antibody reaction solution of an ENVISION kit (Dako) was added by an appropriate amount (enough to immerse the tissue sections therein), and allowed for reaction at room temperature for 60 minutes. After washing with PBS containing 0.05% Tween-20 at room temperature for 5 minutes 3 times, a reaction with a DAB substrate solution was allowed for 10 minutes. The reaction was ceased by washing the tissue sections with water. After staining with hematoxylin, dehydration was performed with ethanol and xylene. Specimens were prepared with a specimen-preparation solution (Matsunami Glass Ind., Ltd.), and microscopic examination and recording were performed with a bright field microscope (IX71, Olympus Corporation) (FIG. 11).

8. Antigen Epitope Analysis of Anti-TGF-αAntibodies (1) Examination of Antigen Site by Flow Cytometry Analysis Using Amino Acid Point-Substituted TGF-α

Figure 12A:
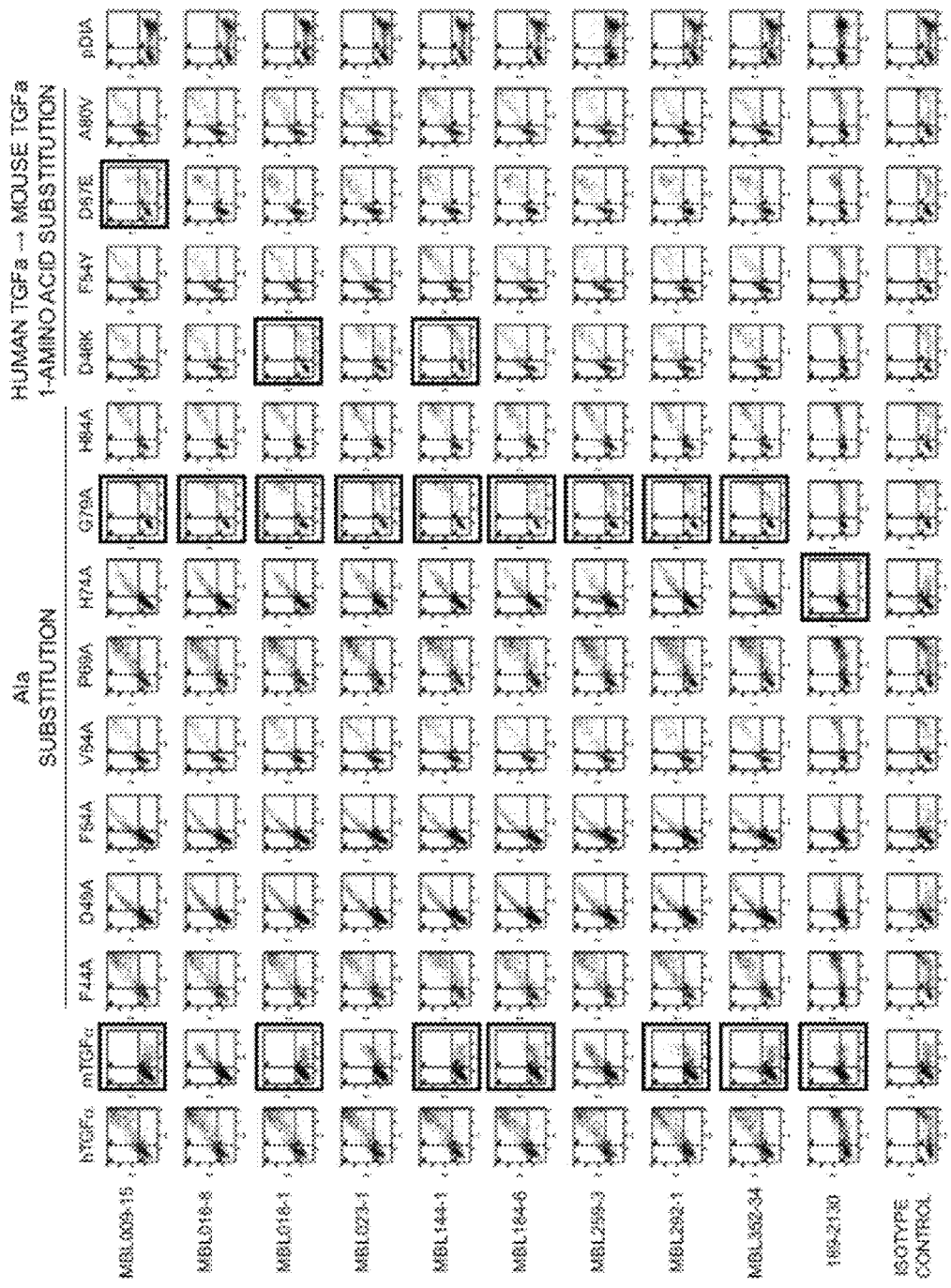
FIG. 12a shows graphs for illustrating the result of analyzing, by flow cytometry, the reactivity of each anti-TGF-α antibody with amino acid-point-substituted TGF-α (indicated by plotted dots). (a) The data on the antibodies whose reactivity was lowered were encompassed by square frames. Nine antibodies from MBL009-15 to MBL352-34 having demonstrated a growth-suppressing effect on the cancer cells in the three-dimensional culture system or the cancer-bearing mouse model commonly became non-reactive in a case of G79A substitution. Meanwhile, the TGF-α neutralized antibody 189-2130 having been observed not to demonstrate a growth-suppressing effect on cancers did not change the reactivity by the G79A substitution, but became non-reactive by H74A substitution.
Figure 12B:
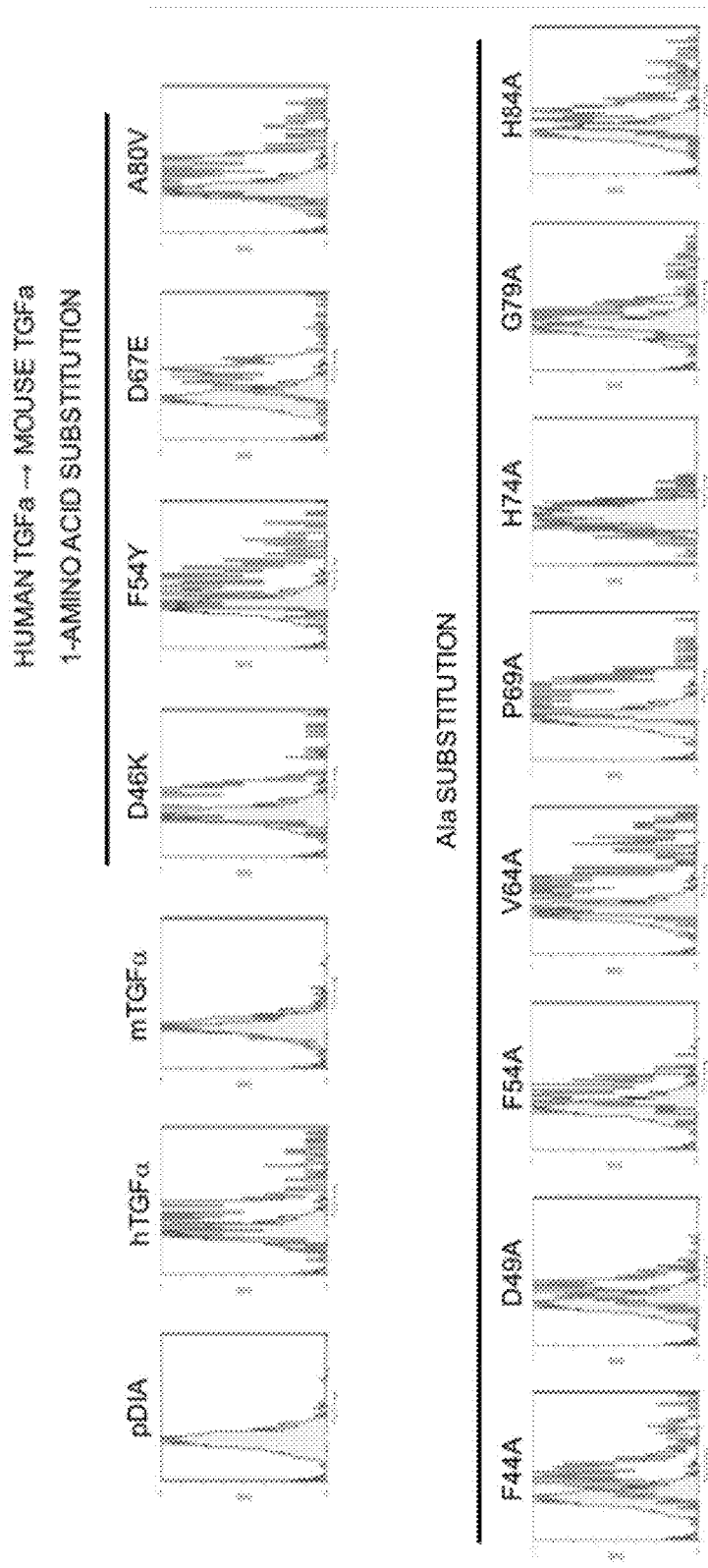
FIG. 12b shows graphs for illustrating the result of analyzing, by flow cytometry, the reactivity of 189-2130 with the amino acid point-substituted TGF-α (indicated by histograms). The reactivity was retained in the case of G79A substitution, while the reactivity was lost in the case of the H74A substitution.

Between positions 40 and 89 in the amino acid sequence of mature TGF-α, there are four amino acid residues which are different between human and mouse amino acid sequences. Expression vectors were constructed for amino acid point-substituted TGF-α, in which one of the four residues was substituted with a mouse amino acid (D46K, F54Y, D67E, and A80V), based on pDIG-TGF-α using AMAP Multi Site-Directed Mutagenesis Kit (Amalgaam Co., Ltd.). Moreover, amino acid point-substituted TGF-α in which one residue at the 44th, 49th, 54th, 64th, 69th, 74th, 79th, or 84th amino acid was substituted with alanine (F44A, D49A, F54A, V64A, P69A, H74A, G79A, and H84A) was also prepared using the same kit. Further, in order to prepare a mouse wild type TGF-α expression vector, a mouse wild type TGF-α gene (1st to 477th bases in the base sequence) (OriGene Technologies, Inc.) was cloned in an expression vector phmAG1 used for animal cells (Amalgaam Co., Ltd.). The vector was designed in such a way that IRES and the gene of a fluorescent protein Azami-Green are linked on the 3' side of the mouse TGF-α gene (hereinafter, the vector is referred to as pDIA-TGF-α). Each of 15 types of expression vectors in total including the expression vectors for these amino acid point-substituted TGF-α, the human wild type TGF-α expression vector, and the mouse wild type TGF-α expression vector, were translently expressed in 293T cells by lipofection (Invitrogen Corporation). The cells ($1 \times 10^5$ cells per sample) were washed with a wash buffer (PBS (−) containing 0.5% BSA and 2 mM EDTA) twice, and then allowed to react with various anti-TGF-α antibodies (diluted to 5 μg/mL with a wash buffer) at 4° C. for 60 minutes. After washed with a wash buffer twice, the cells were allowed to react with a 200-fold diluted PE-labeled anti-mouse IgG antibody (MBL CO., LTD.) at 4° C. for 60 minutes. After washing with a wash buffer twice, the cells were suspended in 500 μL of a wash buffer, and subjected to a flow cytometry analysis with FC-500 (Beckman Coulter, Inc.) to compare and examine the reactivity of the TGF-α antibodies with the human wild type TGF-α and the amino acid point-substituted TGF-α (FIG. 12).

(2) Antigen Site Analysis Using Overlapping Peptide (OLP)

Based on the sequence of mature TGF-α (40-89), the following 11 OLPs were artificially synthesized.

```
                                            (SEQ ID NO: 67)
[OLP-1  (TGF-α 40-48): VVSHFNDCP]

(SEQ ID NO: 68)
[OLP-2  (TGF-α 40-54): VVSHFNDCPDSHTQF]

(SEQ ID NO: 69)
[OLP-3  (TGF-α 48-55): PDSHTQFC]

(SEQ ID NO: 70)
[OLP-4  (TGF-α 50-59): SHTQFCFHGT]

(SEQ ID NO: 71)
[OLP-5  (TGF-α 56-66): FHGTCRFLVQE]

(SEQ ID NO: 72)
[OLP-6  (TGF-α 56-70): FHGTCRFLVQEDKPA]

(SEQ ID NO: 73)
[OLP-7  (TGF-α 61-72): RFLVQEDKPACV]

(SEQ ID NO: 74)
[OLP-8  (TGF-α 72-81): VCHSGYVGAR]

(SEQ ID NO: 75)
[OLP-9  (TGF-α 74-89): HSGYVGARCEHADLLA]

(SEQ ID NO: 76)
[OLP-10 (TGF-α 77-89): YVGARCEHADLLA]

(SEQ ID NO: 77)
[OLP-11 (TGF-α 80-89): ARCEHADLLA]
```

As a positive control antigen, proTGF-α-hFc was used. Moreover, as a negative control antibody, isotype control mouse IgG2a (MBL CO., LTD.) was used.

Figure 13:
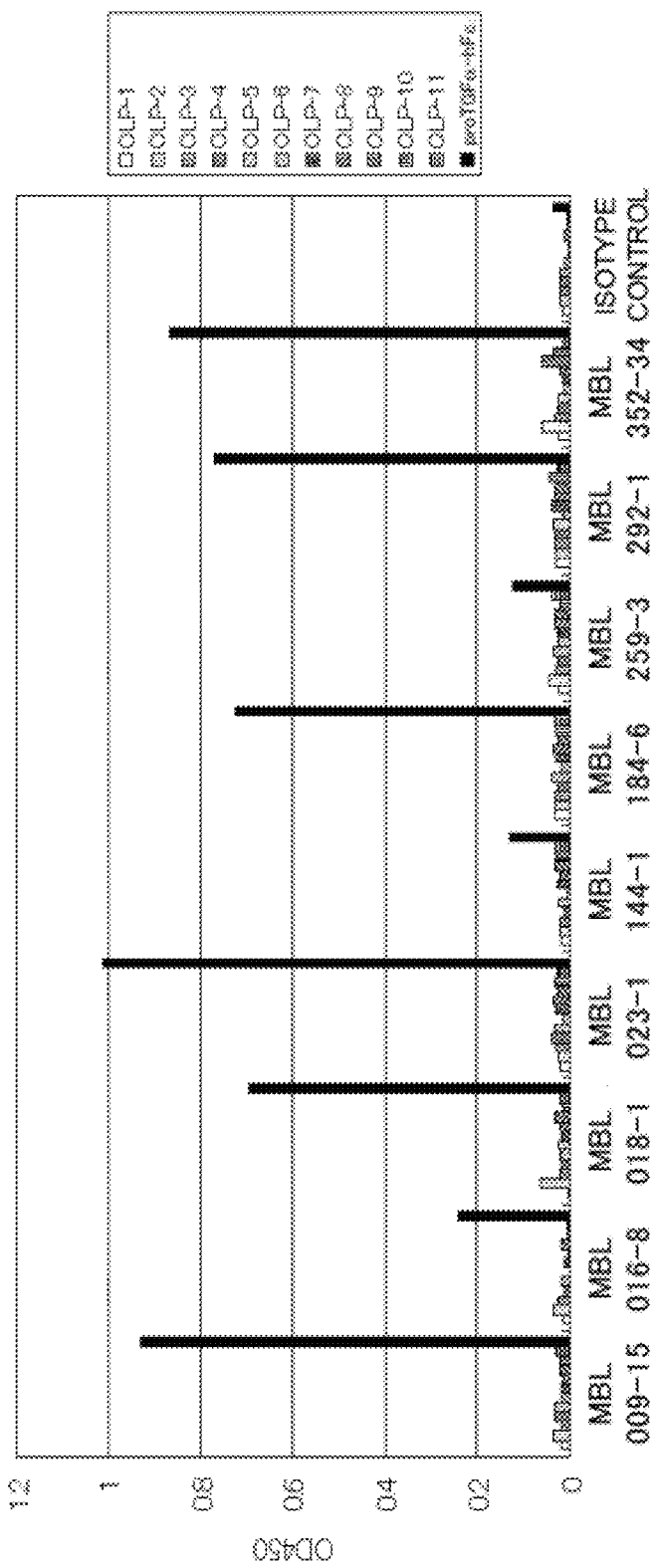
FIG. 13 shows a graph for illustrating the reactivity of each anti-TGF-α antibody with plates on which TGF-α polypeptide fragments were immobilized. Each polypeptide has overlapping portions with others. As a positive control of the antigen-antibody reaction, proTGF-α-hFc was used.

PBS(−) containing each of the OLPs and the positive control antigen at 1 μg/mL was added to a 96-well plate (F96 Maxisorp NUNC-Immuno plate (NUNC A/S)) by 50 μL per well and allowed for reaction at 4° C. overnight, so that the antigen was adsorbed to the plate. After the supernatant was discarded, a blocking solution (PBS(−) containing 1% BSA and 0.1% NaN$_3$) was added thereto at 100 μL/well, and left standing at 4° C. overnight. After the blocking solution was completely removed, PBS(−) containing each anti-TGF-α antibody by 5 μg/mL was added to each well by 50 μL, and allowed for reaction at room temperature for 1 hour. After the plate was washed with PBS(−) 5 times, POD-labeled anti-mouse IgG (20,000-fold diluted, enzyme-labeled antibody-diluted solution (20 mM HEPES, 1% bovine serum albumin, 0.135 M NaCl, 0.1% para-hydroxyphenylacetate, 0.15% Kathon CG, 0.05% BPB)) was added thereto by 50 μL/well, and incubated at room temperature for 1 hour. After the plate was washed with PBS(−) 5 times, TMB (3,3′,5,5′-tetramethylbenzidine) was added by 50 μL/well and incubated at room temperature for 30 minutes for coloration. A 0.5-N phosphoric acid solution was added by 50 μL/well to cease the reaction, and the absorbance was measured at 450 nm/620 nm (FIG. 13).

9. Determination of Antibody Sequence

The sequence determination by a PCR method was carried out according to Antibody Engineering (J. McCAFFERTY, H. R. Hoogenboom, D. J. Chiswell eds.). Specifically, 1×10$^5$ cells of hybridomas producing the anti-TGF-α antibodies were collected, and total RNA was purified and recovered with RNeasy mini kit (Qiagen GmbH). The variable regions of mouse IgG were amplified by the PCR method using KOD Plus (Toyobo Co., Ltd.) as the DNA synthesizing enzyme and the following cloning primers.

```
[Sense primers for L chain]
                                           (SEQ ID NO: 78)
MKV1:  5'-ATGAAGTTGCCTGTTAGGCTGTTGGTGCTG-3'

(SEQ ID NO: 79)
MKV2:  5'-ATGGAGWCAGACACACTCCTGYTATGGGTG-3'

(SEQ ID NO: 80)
MKV3:  5'-ATGAGTGTGCTCACTCAGGTCCTGGSGTTG-3'

(SEQ ID NO: 81)
MKV4:  5'-ATGAGGRCCCCTGCTCAGWTTYTTGGMWTCTTG-3'

(SEQ ID NO: 82)
MKV5:  5'-ATGGATTTWCAGGTGCAGATTWTCAGCTTC-3'

(SEQ ID NO: 83)
MKV6:  5'-ATGAGGTKCYYTGYTSAGYTYCTGRGG-3'

(SEQ ID NO: 84)
MKV7:  5'-ATGGGCWTCAAGATGGAGTCACAKWYYCWGG-3'

(SEQ ID NO: 85)
MKV8:  5'-ATGTGGGAYCTKTTTYCMMTTTTTCAATTG-3'

(SEQ ID NO: 86)
MKV9:  5'-ATGGTRTCCWCASCTCAGTTCCTTG-3'

(SEQ ID NO: 87)
MKV10: 5'-ATGTATATATGTTTGTTGTCTATTTCT-3'

(SEQ ID NO: 88)
MKV11: 5'-ATGGAAGCCCCAGCTCAGCTTCTCTTCC-3'

[Antisense primer for L chain]
                                           (SEQ ID NO: 89)
MKC:   5'-ACTGGATGGTGGGAAGATGG-3'

[Sense primers for H chain]
                                           (SEQ ID NO: 90)
MHV1:  5'-ATGAAATGCAGCTGGGGCATSTTCTTC-3'

(SEQ ID NO: 91)
MHV2:  5'-ATGGGATGGAGCTRTATCATSYTCTT-3'

(SEQ ID NO: 92)
MHV3:  5'-ATGAAGWTGTGGTTAAACTGGGTTTTT-3'

(SEQ ID NO: 93)
MHV4:  5'-ATGRACTTTGGGYTCAGCTTGRTTT-3'

(SEQ ID NO: 94)
MHV5:  5'-ATGGACTCCAGGCTCAATTTAGTTTTCCTT-3'

(SEQ ID NO: 95)
MHV6:  5'-ATGGCTGTCYTRGSGCTRCTCTTCTGC-3'

(SEQ ID NO: 96)
MHV7:  5'-ATGGRATGGAGCKGGRTCTTTMTCTT-3'

(SEQ ID NO: 97)
MHV8:  5'-ATGAGAGTGCTGATTCTTTTGTG-3'

(SEQ ID NO: 98)
MHV9:  5'-ATGGMTTGGGTGTGGAMCTTGCTATTCCTG-3'

(SEQ ID NO: 99)
MHV10: 5'-ATGGGCAGACTTACATTCTCATTCCTG-3'

(SEQ ID NO: 100)
MHV11: 5'-ATGGATTTTGGGCTGATTTTTTTTATTG-3'

(SEQ ID NO: 101)
MHV12: 5'-ATGATGGTGTTAAGTCTTCTGTACCTG-3'

[Antisense primer for IgG1]
                                           (SEQ ID NO: 102)
MHCG1: 5'-CAGTGGATAGACAGATGGGGG-3'

[Antisense primers for IgG2a]
                                           (SEQ ID NO: 103)
MHCG2a: 5'-CAGTGGATAGACAGATGGGGC-3'
```

The amplified products by PCR were incorporated into a cloning vector (pBluescriptII, Toyobo Co., Ltd.), and the gene sequence was analyzed (ABI3130, Life Technologies Corporation). Utilizing IgBLAST, the framework and CDR of the obtained antibody sequence were specified.

Next, in order to verify that the obtained variable regions were capable of recognizing TGF-α, a humanized chimeric antibody was produced using H chain- and L chain-variable region genes by the following method. The human constant regions utilized were Human IgG1 constant regions shown in Non Patent Literature (Sequence of proteins of Immunological interest (NIH Publication No. 91-3242, 1991)) by Kabat et al.

The genes were amplified using [sense primers for H chain constant region]: 5′-AAGCTTCGTACGCCCGCTCT-TCGCCTCCACCAAGGGCCCATC-3′ (SEQ ID NO: 104), [antisense primer]: 5′-CGCCTGACGCGTCCCTCATT-TACCCGGAGACAGGGAGAGACTCTTCTGCGT GTAG-3′ (SEQ ID NO: 105), [sense primers for L chain constant region]: 5′-AAGCTTCGTACGCCCGCTCT-TCACTGTGGCTCACCATCTGT-3′ (SEQ ID NO: 106), and [antisense primer]: 5′-CGCCTGACGCGTCCCCTAA-CACTCTCCCCTGTTGA-3′ (SEQ ID NO: 107). The obtained H chain constant region gene sequence fragment and L chain constant region gene sequence fragment were introduced into pEHX1.1 and pELX2.1 (Toyobo Co., Ltd.) digested with a restriction enzyme SmaI using In-Fusion PCR Cloning Kit (Takara Bio Inc.) (hereinafter, the expression vectors are respectively referred to as "hHC-pEHX" and "hLC-pELX").

Next, by amplification with primers for humanized chimeric antibody production shown below, H chain- and L chain-DNA fragments of each anti-TGF-α antibody were obtained and respectively introduced by an In-Fusion method into hHC-pEHX and hLC-pELX digested with a restriction enzyme SapI.

```
<MBL009-15>
H chain
Sense:
                                  (SEQ ID NO: 108)
5'-GCCCGCTCTTCGCCTATGAGAGTGCTGATTCTTTTGT-3'

Antisense:
                                  (SEQ ID NO: 109)
5'-GGCCCTTGGTGGAGGCTGCAGAGACAGTGACCAGAGT-3'

L chain
Sense:
                                  (SEQ ID NO: 110)
5'-GCCCGCTCTTCACTGATGGTGTCCTCAGCTCAGTTCCTTG-3'

Antisense:
                                  (SEQ ID NO: 111)
5'-ATGGTGCAGCCACAGTTTTGATTTCCAGCTTGGTGCC-3'

<MBL016-8>
H chain
Sense:
                                  (SEQ ID NO: 112)
5'-GCCCGCTCTTCGCCTATGAAATGCAGCTGGGGCATG-3'

Antisense:
                                  (SEQ ID NO: 113)
5'-GGCCCTTGGTGGAGGCTGCAGAGACAGTGACCAGAGT-3'

L chain
Sense:
                                  (SEQ ID NO: 114)
5'-GCCCGCTCTTCACTGATGAGGTTCTCTGTTGAGTTC-3'

Antisense:
                                  (SEQ ID NO: 115)
5'-ATGGTGCAGCCACAGTTTTTATTTCCAGCTTGGTCCC-3'

<MBL018-1>
H chain
Sense:
                                  (SEQ ID NO: 116)
5'-GCCCGCTCTTCGCCTATGGAATGTAACTGGATACTT-3'

Antisense:
                                  (SEQ ID NO: 117)
5'-GGCCCTTGGTGGAGGCTGAGGAGACGGTGACTGAGGT-3'

L chain
Sense:
                                  (SEQ ID NO: 118)
5'-GCCCGCTCTTCACTGATGGGCATCAAGATGGAGTCA-3'

Antisense:
                                  (SEQ ID NO: 119)
5'-ATGGTGCAGCCACAGTTCTGATTTCCAGTTTGGTGCC-3'

<MBL144-1>
H chain
Sense:
                                  (SEQ ID NO: 120)
5'-GCCCGCTCTTCGCCTATGATGGTGTTAAGTCTTCTG-3'

Antisense:
                                  (SEQ ID NO: 121)
5'-GGCCCTTGGTGGAGGCTGAGGAGACTGTGAGAGTGGT-3'

L chain
Sense:
                                  (SEQ ID NO: 122)
5'-GCCCGCTCTTCACTGATGGTATCCTCAGCTCAGTTC-3'

Antisense:
                                  (SEQ ID NO: 123)
5'-ATGGTGCAGCCACAGTTTTGATTTCCAGCTTGGTGCC-3'

<MBL184-6>
H chain
Sense:
                                  (SEQ ID NO: 124)
5'-GCCCGCTCTTCGCCTATGAAATGCAGCTGGGGCATC-3'

Antisense:
                                  (SEQ ID NO: 125)
5'-GGCCCTTGGTGGAGGCTGAGGAGACTGTGAGAGTGGT-3'

L chain
Sense:
                                  (SEQ ID NO: 126)
5'-GCCCGCTCTTCACTGATGAAGTTTCCTTTTCAACTT-3'

Antisense:
                                  (SEQ ID NO: 127)
5'-ATGGTGCAGCCACAGTTTTGATTTCCAGTTTGGTGCC-3'

<MBL259-3>
H chain
Sense:
                                  (SEQ ID NO: 128)
5'-GCCCGCTCTTCGCCTATGAAATGCAGCTGGGGCATG-3'

Antisense:
                                  (SEQ ID NO: 129)
5'-GGCCCTTGGTGGAGGCTGCAGAGACAGTGACCAGAGT-3'

L chain
Sense:
                                  (SEQ ID NO: 130)
5'-GCCCGCTCTTCACTGATGAGTGTGCTCACTCAGGTC-3'

Antisense:
                                  (SEQ ID NO: 131)
5'-ATGGTGCAGCCACAGTTTTTATTTCCAGTTTGGTCCC-3'

<MBL292-1>
H chain
Sense:
                                  (SEQ ID NO: 132)
5'-GCCCGCTCTTCGCCTATGAAATGCAGCTGGGGCATC-3'

Antisense:
                                  (SEQ ID NO: 133)
5'-GGCCCTTGGTGGAGGCTGAGGAGACTGTGAGAGTGGT-3'

L chain
Sense:
                                  (SEQ ID NO: 134)
5'-GCCCGCTCTTCACTGATGAAGTTTCCTTTTCAACTT-3'

Antisense:
                                  (SEQ ID NO: 135)
5'-ATGGTGCAGCCACAGTTTTGATTTCCAGCTTGGTGCC-3'

<MBL352-34>
H chain
Sense:
                                  (SEQ ID NO: 136)
5'-GCCCGCTCTTCGCCTATGAAATGCAGCTGGGGCATG-3'

Antisense:
                                  (SEQ ID NO: 137)
5'-GGCCCTTGGTGGAGGCTGAGGAGACTGTGAGAGTGGT-3'

L chain
Sense:
                                  (SEQ ID NO: 138)
5'-GCCCGCTCTTCACTGATGAAGTTTCCTTTTCAACTT-3'

Antisense:
                                  (SEQ ID NO: 139)
5'-ATGGTGCAGCCACAGTTTTGATTTCCAGCTTGGTGCC-3'
```

The humanized chimeric antibody expression vectors thus prepared were co-transfected into 293T cells. A flow cytometry analysis was carried out on the culture supernatant in the same manner as described above to check the reactivity with the 293T cells expressing transmembrane TGF-α.

As to an antibody gene whose sequence was not determined by the above-described PCR method, the antibody gene was cloned by a 5'-RACE method. The 5'-RACE method was carried out using Gene Racer Kit (Invitrogen Corporation) by the following method. Total RNA recovered with RNeasy mini kit (Qiagen GmbH) was treated with a bovine intestine-derived phosphatase. 5'-Dephosphorylated RNA recovered by ethanol precipitation was treated with tobacco acid pyrophosphatase to remove the 5'-cap structure. To the 5'-decapped RNA recovered by ethanol precipitation, Gene Racer RNA oligo was added using T4 RNA ligase. This RNA adduct was recovered by ethanol precipitation, and a reverse transcription reaction was carried out with Super Script III RT. The antibody gene was amplified using the cDNA thus synthesized as a template, GeneRacer 5' primer, antisense primers specific respectively to the L chain and the H chain (H chain: 5'-GATGGGGGTGTCGTTTTGGC-3' (SEQ ID NO: 140), L chain: GTTGGTGCAGCATCAGCCCG-3' (SEQ ID NO: 141)), and KOD plus. The amplified DNA was introduced into a pCR-Blunt II-TOPO vector, and the gene sequence was determined (ABI3130). The construction of the expression vector for the humanized chimeric antibody and the checking of the activity of the obtained humanized chimeric antibody were performed according to the above-described methods.

Example 1

Acquisition of Anti-TGF-α Monoclonal Antibodies

As the immunogen, proTGF-α-mFc alone or a combination of proTGF-α-mFc and proTGF-α-mH was used. Various strains of mice, 60 mice in total, were immunized with solutions of these together with Complete Freund's Adjuvant (FIGS. 1a, b). Using the supernatant of hybridomas obtained by fusing lymphocytes of the immunized mice with a myeloma, the reactivity with the immunogens or the antigens for screening was evaluated by antigen solid phase ELISA. Next, using TGF-α/293T cells that were 293T cells transiently expressing full-length TGF-α, a flow cytometry analysis was carried out to select the hybridoma supernatant showing the reactivity with transmembrane TGF-α and also the hybridoma supernatant capable of immunoprecipitation of the secreted antigen proTGF-α-mH (FIG. 4). After monoclones were produced from the hybridomas by the limiting dilution method, immunogen solid phase ELISA and immunoprecipitation were carried out again. Thus, 39 types of anti-TGF-α monoclonal antibodies were selected in total (Table 1). In order to check the reactivity of the purified antibodies with TGF-α, ELISA was performed in which various TGF-α and negative control were immobilized (FIG. 2), and the reactivity was checked by flow cytometry using the TGF-α/293T cells (FIG. 3).

Example 2

Selection of TGF-α Neutralized Antibodies Capable of Inhibiting Binding Between TGF-α and EGFR In order to select an antibody having an activity of inhibiting binding between TGF-α and EGFR (neutralized antibody) from the obtained anti-TGF-α antibodies, the following experiment was conducted using EGFR-overexpressing cancer cells A431. When TGF-α is added to A431 cultured in a serum-free medium, the EGFR tyrosine phosphorylation level is transiently increased. The antibody searched for was one that did not increase the EGFR phosphorylation level in comparison with the PBS control when A431 was treated with the TGF-α solution having been reacted with each anti-TGF-α antibody in advance. As a result, it was revealed that when the antibodies were added at a concentration of 10 μg/mL, MBL352-34, MBL292-1, MBL184-6, MBL016-8, MBL144-1, MBL023-1, and MBL018-1 inhibited EGFR tyrosine phosphorylation (P-Tyr1173) by 70% to 100% or more (FIGS. 5a, b). Meanwhile, the TGF-α neutralized antibody 189-2130 (NPL 50) and EGFR-blocking antibody 225 used as the controls inhibited EGFR phosphorylation only by approximately 20% and 40%, respectively.

Example 3

Examination of Transmembrane TGF-α or Membrane-Bound TGF-α in Cancer Cells

Next, in order to verify the presence of TGF-α on the cell surfaces of cancer cells having a mutated K-Ras gene, a flow cytometry analysis was carried using MBL259-3 having been observed to have relatively favorable reactivity with the TGF-α/293T cells. As a result, colorectal cancer-derived K-Ras gene G12V-homo mutated cancer cells SW620 and lung cancer-derived K-Ras gene G12D-hetero mutated cell line A427 were reacted with MBL259-3 (FIG. 6).

Example 4

Tumor-Suppressing Effect of Anti-TGF-α Antibodies in Cancer-Bearing Mouse Model Having K-Ras Gene Mutated Cancer Transplanted Each of the K-Ras gene mutated cancer cells A427 and SW620 having been observed to have the reactivity with the anti-TGF-α antibody in FIG. 6 was subcutaneously transplanted into a nude mouse. At the same time, various anti-TGF-α antibodies were subcutaneously administered thereto. Thereafter, the antibodies were administered 6 or 7 times as frequently as twice a week, and the tumor size was measured. As a result, among the A427 cancer-bearing mice, a certain cancer-proliferation suppression was observed in the EGFR blocking antibody cetuximab-administered group. Meanwhile, significant cancer suppressions were observed in the groups to which MBL023-1, MBL259-3, and MBL292-1 were administered among the anti-TGF-α antibodies obtained by the present inventors, in comparison with cetuximab (FIGS. 7a, b). Moreover, among the SW620 cancer-bearing mice, no anti-tumor effect was observed in the cetuximab-administered group, whereas significant cancer-proliferation suppressions were observed in the groups to which the anti-TGF-α antibodies MBL144-1, MBL259-3, and MBL292-1 were administered (FIGS. 8a, b).

Example 5

Growth-Suppressing Effect of Anti-TGF-α Antibodies in Three-Dimensional Cell Culture System TGF-α not only directly acts on cancer cell proliferation, but also induces a blood vessel for transporting nutrients to cancer tissues and promotes proliferation of a stroma serving as the scaffold, thereby comprehensively assisting the enlargement of the cancer tissues. For this reason, examined was whether the anti-TGF-α antibodies observed to have a tumor-suppressing effect in the cancer-bearing mouse model directly suppressed cancer proliferation, suppressed angiogenesis, or suppressed both. First, using the three-dimensional cell culture system in which cells were cultured in a gel medium, A427 and SW620 were allowed to proliferate. To the culture system, various anti-TGF-α antibodies were added to examine the influence against cancer cell proliferation (FIG. 9). As a result, the anti-TGF-α antibodies MBL009-15, MBL016-8, MBL018-1, MBL023-1, MBL144-1, MBL184-6, MBL292-1, and MBL352-34 suppressed the proliferation of A427 and SW620 in a concentration-dependent manner. Meanwhile, the growth-suppressing effect was hardly observed in the TGF-α neutralized antibody 189-2130 (NPL 50) and the EGFR blocking antibody cetuximab. Moreover, in order to check that cetuximab used in the experiment was not inactivated, a proliferation inhibition test was carried out on A431. As a result, a strong growth-suppressing activity was observed from cetuximab. Note that in this experimental system also, the anti-TGF-α antibodies obtained by the present inventors demonstrated a strong growth-suppressing effect.

Example 6

Inhibiting Effect of Anti-TGF-α Antibodies on Angiogenesis

Next, using the angiogenesis experimental system for inducing angiogenesis in a mouse hypodermis, the angiogenesis-inhibiting effect by the anti-TGF-α antibodies was evaluated. In the positive control experiment, it was confirmed that the migration of vascular endothelial cells into an angioreactor due to VEGF/FGF-2 was suppressed in a concentration-dependent manner by the anti-VEGF antibody bevacizumab (FIG. 10a). When TGF-α was added to the angioreactor, the migration of the vascular endothelial cells was enhanced in comparison with a case of adding only PBS. When each of the anti-TGF-α antibodies (MBL009-15, MBL016-8, MBL018-1, MBL023-1, MBL292-1, MBL352-34) was added to the system, a suppression of vascular endothelial cell induction was observed. Particularly, MBL292-1 suppressed the migration almost at the same level as in the case of adding only PBS (FIG. 10b).

The above results revealed that most of the anti-TGF-α antibodies demonstrating a growth-suppressing effect on cancer cells had an antagonistic activity on binding of TGF-α to EGFR, and further demonstrated an activity of suppressing angiogenesis induction.

Example 7

Reactivity of Anti-TGF-α Antibody with K-Ras Gene Mutated Colorectal Cancer Cells SW620 and Colorectal Cancer Patient-Derived Specimen in Immunohistostaining Immunohistostaining was carried out on a thin section of paraffin-embedded K-Ras gene mutated cancer SW620 using the anti-TGF-α antibody MBL259-3. Obvious staining was observed in comparison with the isotype control antibody (FIGS. 11a, 11b). Further, with respect to the colorectal cancer patient-derived paraffin-embedded cancer tissue section, MBL259-3 strongly stained the cancer tissue. In addition, staining was also observed in this event at a part of an interstitial tissue developed near the cancer site.

Example 8

Antigen Epitope Analysis of Anti-TGF-α Antibodies Showing Growth-Suppressing Effect on Cancer Cells In order to find common features to the anti-TGF-α antibodies demonstrating the cancer cell-proliferation suppression, amino acid point-substituted TGF-α was produced by modifying one of amino acids of TGF-α with another amino acid, and the reactivity with each anti-TGF-α antibody was examined.

As the amino acid point-substituted TGF-α used in the experiment, produced were D46K-substituted, F54Y-substituted, D67E-substituted, and A80V-substituted TGF-α, in which a human TGF-α amino acid was point-substituted with a mouse TGF-α amino acid. Moreover, one residue at the 44th, 49th, 54th, 64th, 60th, 74th, 79th, or 84th amino acid was substituted with alanine to prepared F44A-substituted, D49A-substituted, F54A-substituted, V64A-substituted, P69A-substituted, H74A-substituted, G79A-substituted, and H84A-substituted TGF-α. These were respectively expressed on the cell surfaces of 293T cells, and the reactivity with each anti-TGF-α antibody was examined by flow cytometry. As a result, in all of nine clones of the anti-TGF-α antibodies observed to have a growth-suppressing effect on the K-Ras gene mutated cancer in vivo or in vitro (MBL009-15, MBL016-8, MBL018-1, MBL023-1, MBL144-1, MBL184-6, MBL259-3, MBL292-1, and MBL352-34), the reactivity with the G79A substitution analog was significantly lowered in common (FIG. 12). Meanwhile, as to the antibody 189-2130 (NPL 50) not observed to have a cancer growth-suppressing effect despite the neutralizing activity, the lowering in the reactivity with the G79A substitution analog was not observed. Although the reactivity of 189-2130 with the H74A substitution analog was lowered, any of the anti-TGF-α antibodies obtained by the present inventors reacted with the H74A substitution analog as strongly as with the human wild type. Additionally, among the anti-TGF-α antibodies developed by the present inventors, MBL046-21, MBL092-3, MBL159-1, MBL210-20, MBL287-12, MBL305-3, and MBL324-5 (Table 1), which had no growth-suppressing effect on SW620, reacted with the G79A substitution analog at the same level as reacting with the human wild type TGF-α, and thus strongly reacted therewith. Meanwhile, the overlapping peptides (OLPs) of TGF-α were artificially synthesized, and the reactivity with the above-described nine clones of the anti-TGF-α antibodies was examined by ELISA. As a result, these nine clones reacted with proTGF-α-hFc used as the positive control antigen, but any of the antibodies had significantly low reactivity with 11 types of OLPs ($OD_{450}$ value: below 0.06) in comparison with the positive control antigen. Moreover, the OLPs were added to the proTGF-α-hFc solution for competition in the antigen-antibody reaction, but the lowering in the reactivity with proTGF-α-hFc was not observed in any of the antibodies. Hence, it was revealed that even if the reactivity of an antibody was analyzed by utilizing polypeptide fragments of TGF-α, an anti-TGF-α antibody having an anti-tumor effect was not successfully selected.

The above results revealed that selecting an anti-TGF-α antibody based on the reactivity with G79A-substituted TGF-α made it possible to obtain an anti-TGF-α antibody demonstrating a growth-suppressing effect on cancers (including Ras gene mutated type).

Example 9

Figure 14:
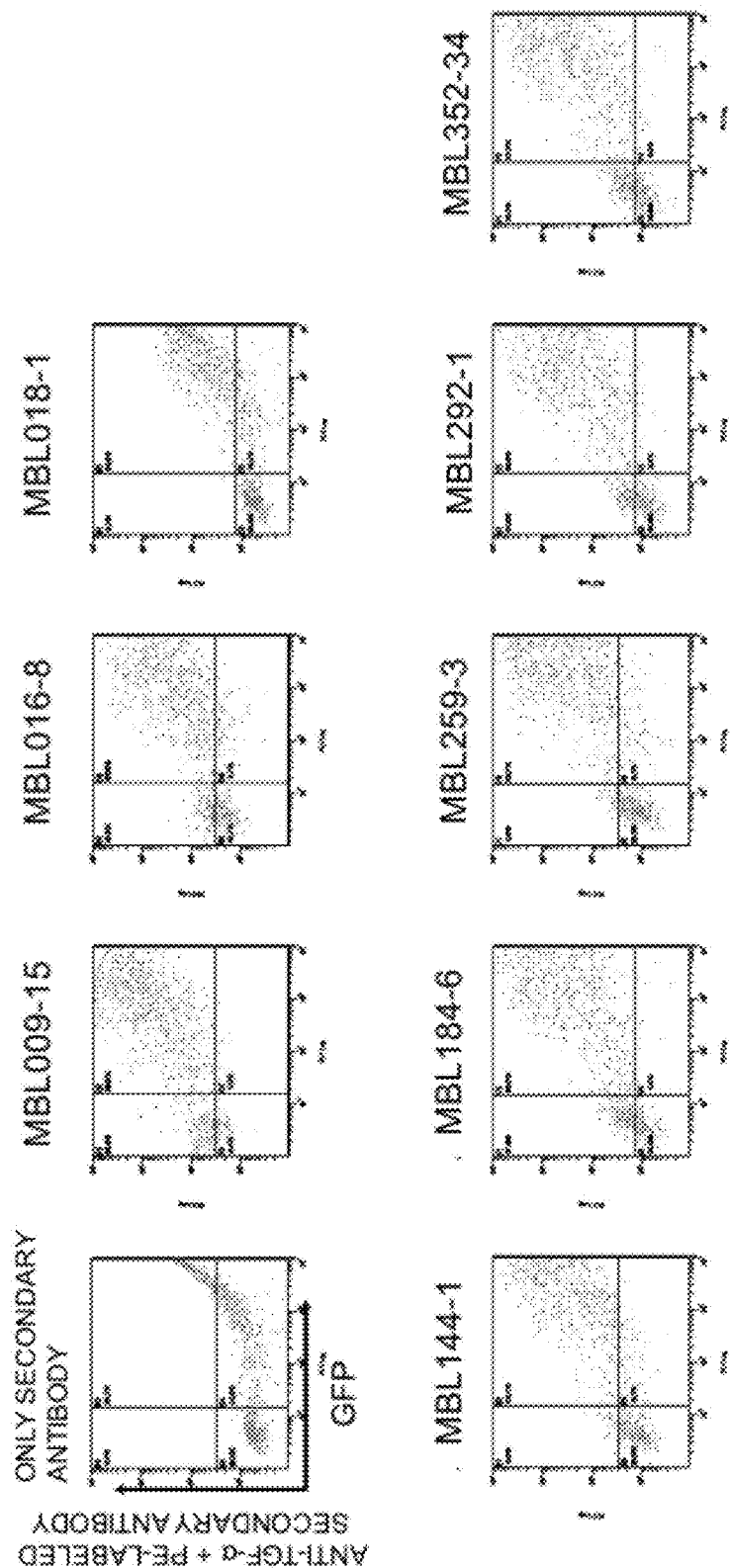
FIG. 14 shows graphs for illustrating the result of analyzing, by flow cytometry, the reactivity of each humanized chimeric anti-TGF-α antibody with transmembrane TGF-α/293T.

Sequence Analysis of Anti-TGF-αAntibodies Demonstrating Growth-Suppressing Effect on Ras Gene Mutated Cancers By the PCR method or 5'-RACE method, the antibody gene was recovered from cells producing each antibody, and H chain- and L chain-gene sequences were determined. In order to confirm that the combination of the H chain and the L chain was correct, the antibody genes of the H chain and the L chain were amplified utilizing primers in Table 11, then introduced into animal expression vectors, and co-expressed in 293T cells. In order to confirm that the obtained recombinant antibodies obtained in the culture supernatant were capable of reacting with TGF-α, the culture supernatant was reacted with transmembrane TGF-α/293T, and subjected to a flow cytometry analysis as in the case of Example 1. As a result, it was confirmed that all of the recombinant antibodies reacted with transmembrane TGF-α (FIG. 14).

[Industrial Applicability]

The antibody of the present invention has an excellent growth-suppressing activity on cancer cell, and accordingly can be used for treatment of cancers. Since demonstrating a strong growth-suppressing effect on Ras mutated cancers highly resistant to available drugs also, the antibody of the present invention is quite useful in the medical field. Moreover, the antibody of the present invention is capable of recognizing a cancer cell expressed on the surface of TGF-α, and thus applicable also to diagnosis of a cancer as well as detection, screening, and the like, of cancer cells.

[Sequence Listing Free Text]

SEQ ID NO: 3
<223> MBL009-15 VL
SEQ ID NO: 4
<223> MBL009-15 VH
SEQ ID NO: 5
<223> MBL016-8 VL
SEQ ID NO: 6
<223> MBL016-8 VH
SEQ ID NO: 7
<223> MBL018-1 VL
SEQ ID NO: 8
<223> MBL018-1 VH
SEQ ID NO: 9
<223> MBL144-1 VL
SEQ ID NO: 10
<223> 144-1 VH
SEQ ID NO: 11
<223> MBL184-6 VL
SEQ ID NO: 12
<223> MBL184-6 VH
SEQ ID NO: 13
<223> MBL259-3 VL
SEQ ID NO: 14
<223> MBL259-3 VH
SEQ ID NO: 15
<223> MBL292-1 VL
SEQ ID NO: 16
<223> MBL292-1 VH
SEQ ID NO: 17
<223> MBL352-34 VL
SEQ ID NO: 18
<223> MBL352-34 VH
SEQ ID NO: 19
<223> MBL009-15 VL CDR1
SEQ ID NO: 20
<223> MBL009-15 VL CDR2
SEQ ID NO: 21
<223> MBL009-15 VL CDR3
SEQ ID NO: 22
<223> MBL009-15 VH CDR1
SEQ ID NO: 23
<223> MBL009-15 VH CDR2
SEQ ID NO: 24
<223> MBL009-15 VH CDR3
SEQ ID NO: 25
<223> MBL016-8 VL CDR1
SEQ ID NO: 26
<223> MBL016-8 VL CDR2
SEQ ID NO: 27
<223> MBL016-8 VL CDR3
SEQ ID NO: 28
<223> MBL016-8 VH CDR1
SEQ ID NO: 29
<223> MBL016-8 VH CDR2
SEQ ID NO: 30
<223> MBL016-8 VH CDR3
SEQ ID NO: 31
<223> MBL018-1 VL CDR1
SEQ ID NO: 32
<223> MBL018-1 VL CDR2
SEQ ID NO: 33
<223> MBL018-1 VL CDR3
SEQ ID NO: 34
<223> MBL018-1 VH CDR1
SEQ ID NO: 35
<223> MBL018-1 VH CDR2
SEQ ID NO: 36
<223> MBL018-1 VH CDR3
SEQ ID NO: 37
<223> MBL144-VL CDR1
SEQ ID NO: 38
<223> MBL144-VL CDR2
SEQ ID NO: 39
<223> MBL144-VL CDR3
SEQ ID NO: 40
<223> MBL144-1 VH CDR1
SEQ ID NO: 41
<223> MBL144-1 VH CDR2
SEQ ID NO: 42
<223> MBL144-1 VH CDR3
SEQ ID NO: 43
<223> MBL184-6 VL CDR1
SEQ ID NO: 44
<223> MBL184-6 VL CDR2
SEQ ID NO: 45
<223> MBL184-6 VL CDR3
SEQ ID NO: 46
<223> MBL184-6 VH CDR1
SEQ ID NO: 47
<223> MBL184-6 VH CDR2
SEQ ID NO: 48
<223> MBL184-6 VH CDR3
SEQ ID NO: 49
<223> MBL259-3 VL CDR1
SEQ ID NO: 50
<223> MBL259-3 VL CDR2
SEQ ID NO: 51
<223> MBL259-3 VL CDR3
SEQ ID NO: 52
<223> MBL259-3 VH CDR1

SEQ ID NO: 53
<223> MBL259-3 VH CDR2
SEQ ID NO: 54
<223> MBL259-3 VH CDR3
SEQ ID NO: 55
<223> MBL292-1 VL CDR1
SEQ ID NO: 56
<223> MBL292-1 VL CDR2
SEQ ID NO: 57
<223> MBL292-1 VL CDR3
SEQ ID NO: 58
<223> MBL292-1 VH CDR1
SEQ ID NO: 59
<223> MBL292-1 VH CDR2
SEQ ID NO: 60
<223> MBL292-1 VH CDR3
SEQ ID NO: 61
<223> MBL352-34 VL CDR1
SEQ ID NO: 62
<223> MBL352-34 VL CDR2
SEQ ID NO: 63
<223> MBL352-34 VL CDR3
SEQ ID NO: 64
<223> MBL352-34 VH CDR1
SEQ ID NO: 65
<223> MBL352-34 VH CDR2
SEQ ID NO: 66
<223> MBL352-34 VH CDR3
SEQ ID NO: 67
<223> artificially synthesized peptide sequence; OLP-1
SEQ ID NO: 68
<223> artificially synthesized peptide sequence; OLP-2
SEQ ID NO: 69
<223> artificially synthesized peptide sequence; OLP-3
SEQ ID NO: 70
<223> artificially synthesized peptide sequence; OLP-4
SEQ ID NO: 71
<223> artificially synthesized peptide sequence; OLP-5
SEQ ID NO: 72
<223> artificially synthesized peptide sequence; OLP-6
SEQ ID NO: 73
<223> artificially synthesized peptide sequence; OLP-7
SEQ ID NO: 74
<223> artificially synthesized peptide sequence; OLP-8
SEQ ID NO: 75
<223> artificially synthesized peptide sequence; OLP-9
SEQ ID NO: 76
<223> artificially synthesized peptide sequence; OLP-10
SEQ ID NO: 77
<223> artificially synthesized peptide sequence; OLP-11
SEQ ID NO: 78
<223> artificially synthesized primer sequence; MKV1
SEQ ID NO: 79
<223> artificially synthesized primer sequence; MKV2
SEQ ID NO: 80
<223> artificially synthesized primer sequence; MKV3
SEQ ID NO: 81
<223> artificially synthesized primer sequence; MKV4
SEQ ID NO: 82
<223> artificially synthesized primer sequence; MKV5
SEQ ID NO: 83
<223> artificially synthesized primer sequence; MKV6
SEQ ID NO: 84
<223> artificially synthesized primer sequence; MKV7
SEQ ID NO: 85
<223> artificially synthesized primer sequence; MKV8
SEQ ID NO: 86
<223> artificially synthesized primer sequence; MKV9
SEQ ID NO: 87
<223> artificially synthesized primer sequence; MKV10
SEQ ID NO: 88
<223> artificially synthesized primer sequence; MKV11
SEQ ID NO: 89
<223> artificially synthesized primer sequence; MKC
SEQ ID NO: 90
<223> artificially synthesized primer sequence; MHV1
SEQ ID NO: 91
<223> artificially synthesized primer sequence; MHV2
SEQ ID NO: 92
<223> artificially synthesized primer sequence; MHV3
SEQ ID NO: 93
<223> artificially synthesized primer sequence; MHV4
SEQ ID NO: 94
<223> artificially synthesized primer sequence; MHV5
SEQ ID NO: 95
<223> artificially synthesized primer sequence; MHV6
SEQ ID NO: 96
<223> artificially synthesized primer sequence; MHV7
SEQ ID NO: 97
<223> artificially synthesized primer sequence; MHV8
SEQ ID NO: 98
<223> artificially synthesized primer sequence; MHV9
SEQ ID NO: 99
<223> artificially synthesized primer sequence; MHV10
SEQ ID NO: 100
<223> artificially synthesized primer sequence; MHV11
SEQ ID NO: 101
<223> artificially synthesized primer sequence; MHV12
SEQ ID NO: 102
<223> artificially synthesized primer sequence; MHCG1
SEQ ID NO: 103
<223> artificially synthesized primer sequence; MHCG2a
SEQ ID NO: 104
<223> artificially synthesized primer sequence; human IgG1 CH sense primer
SEQ ID NO: 105
<223> artificially synthesized primer sequence; human IgG1 CH antisense primer
SEQ ID NO: 106
<223> artificially synthesized primer sequence; human IgG1 CL sense primer
SEQ ID NO: 107
<223> artificially synthesized primer sequence; human IgG1 CL antisense primer
SEQ ID NO: 108
<223> artificially synthesized primer sequence; MBL009-15 H sense primer
SEQ ID NO: 109
<223> artificially synthesized primer sequence; MBL009-15 H antisense primer
SEQ ID NO: 110
<223> artificially synthesized primer sequence; MBL009-15 L sense primer
SEQ ID NO: 111
<223> artificially synthesized primer sequence; MBL009-15 L antisense primer
SEQ ID NO: 112
<223> artificially synthesized primer sequence; MBL016-8 H sense primer
SEQ ID NO: 113
<223> artificially synthesized primer sequence; MBL016-8 H antisense primer SEQ ID NO: 114
<223> artificially synthesized primer sequence; MBL016-8 L sense primer
SEQ ID NO: 115
<223> artificially synthesized primer sequence; MBL016-8 L antisense primer
SEQ ID NO: 116
<223> artificially synthesized primer sequence; MBL018-1 H sense primer
SEQ ID NO: 117
<223> artificially synthesized primer sequence; MBL018-1 H antisense primer
SEQ ID NO: 118
<223> artificially synthesized primer sequence; MBL018-1 L sense primer
SEQ ID NO: 119
<223> artificially synthesized primer sequence; MBL018-1 L antisense primer
SEQ ID NO: 120
<223> artificially synthesized primer sequence; MBL144-1 H sense primer
SEQ ID NO: 121
<223> artificially synthesized primer sequence; MBL144-1 H antisense primer
SEQ ID NO: 122
<223> artificially synthesized primer sequence; MBL144-1 L sense primer
SEQ ID NO: 123
<223> artificially synthesized primer sequence; MBL144-1 L antisense primer
SEQ ID NO: 124
<223> artificially synthesized primer sequence; MBL184-6 H sense primer
SEQ ID NO: 125
<223> artificially synthesized primer sequence; MBL184-6 H antisense primer
SEQ ID NO: 126
<223> artificially synthesized primer sequence; MBL184-6 L sense primer
SEQ ID NO: 127
<223> artificially synthesized primer sequence; MBL184-6 L antisense primer
SEQ ID NO: 128
<223> artificially synthesized primer sequence; MBL259-3 H sense primer
SEQ ID NO: 129
<223> artificially synthesized primer sequence; MBL259-3 H antisense primer
SEQ ID NO: 130
<223> artificially synthesized primer sequence; MBL259-3 L sense primer
SEQ ID NO: 131
<223> artificially synthesized primer sequence; MBL259-3 L antisense primer
SEQ ID NO: 132
<223> artificially synthesized primer sequence; MBL292-1 H sense primer
SEQ ID NO: 133
<223> artificially synthesized primer sequence; MBL292-1 antisense primer
SEQ ID NO: 134
<223> artificially synthesized primer sequence; MBL292-1 L sense primer
SEQ ID NO: 135
<223> artificially synthesized primer sequence; MBL292-1 L antisense primer
SEQ ID NO: 136
<223> artificially synthesized primer sequence; MBL352-34 H sense primer
SEQ ID NO: 137
<223> artificially synthesized primer sequence; MBL352-34 H antisense primer
SEQ ID NO: 138
<223> artificially synthesized primer sequence; MBL352-34 L sense primer
SEQ ID NO: 139
<223> artificially synthesized primer sequence; MBL352-34 L antisense primer
SEQ ID NO: 140
<223> artificially synthesized primer sequence; 5'-RACE H antisense primer
SEQ ID NO: 141
<223> artificially synthesized primer sequence; 5'-RACE L antisense primer
SEQ ID NO: 142
<223> MBL009-15 VL cDNA
SEQ ID NO: 143
<223> MBL009-15 VH cDNA
SEQ ID NO: 144
<223> MBL016-8 VL cDNA
SEQ ID NO: 145
<223> MBL016-8 VH cDNA
SEQ ID NO: 146
<223> MBL018-1 VL cDNA
SEQ ID NO: 147
<223> MBL018-1 VH cDNA
SEQ ID NO: 148
<223> MBL144-1 VL cDNA
SEQ ID NO: 149
<223> MBL144-1 VH cDNA
SEQ ID NO: 150
<223> MBL184-6 VL cDNA
SEQ ID NO: 151
<223> MBL184-6 VH cDNA
SEQ ID NO: 152
<223> MBL259-3 VL cDNA
SEQ ID NO: 153
<223> MBL259-3 VH cDNA
SEQ ID NO: 154
<223> MBL292-1 VL cDNA
SEQ ID NO: 155
<223> MBL292-1 VH cDNA
SEQ ID NO: 156
<223> MBL352-34 VL cDNA
SEQ ID NO: 157
<223> MBL352-34 VH cDNA

The invention claimed is:

1. An antibody that specifically binds to human TGF-α, wherein the antibody comprises any one of the following characteristics (a) to (h):
   (a) a light chain variable region including the amino acid sequences of SEQ ID NOs: 19 to 21, and
   a heavy chain variable region including the amino acid sequences of SEQ ID NOs: 22 to 24;
   (b) a light chain variable region including the amino acid sequences of SEQ ID NOs: 25 to 27, and
   a heavy chain variable region including the amino acid sequences of SEQ ID NOs: 28 to 30;
   (c) a light chain variable region including the amino acid sequences of SEQ ID NOs: 31 to 33, and
   a heavy chain variable region including the amino acid sequences of SEQ ID NOs: 34 to 36;
   (d) a light chain variable region including the amino acid sequences of SEQ ID NOs: 37 to 39, and
   a heavy chain variable region including the amino acid sequences of SEQ ID NOs: 40 to 42;
   (e) a light chain variable region including the amino acid sequences of SEQ ID NOs: 43 to 45, and
   a heavy chain variable region including the amino acid sequences of SEQ ID NOs: 46 to 48;
   (f) a light chain variable region including the amino acid sequences of SEQ ID NOs: 49 to 51, and
   a heavy chain variable region including the amino acid sequences of SEQ ID NOs: 52 to 54;
   (g) a light chain variable region including the amino acid sequences of SEQ ID NOs: 55 to 57, and
   a heavy chain variable region including the amino acid sequences of SEQ ID NOs: 58 to 60; and
   (h) a light chain variable region including the amino acid sequences of SEQ ID NOs: 61 to 63, and
   a heavy chain variable region including the amino acid sequences of SEQ ID NOs: 64 to 66.

2. The antibody according to claim 1 having a growth-suppressing activity on cancer cells having a mutated Ras gene.

3. The antibody according to claim 1, wherein the antibody binds human TGF-α having a mutated glycine at a position corresponding to position 79 of SEQ ID NO:2 with lower affinity than to wild type human TGF-α.

4. The antibody according to claim 3, wherein the human TGF-α having the mutated glycine at a position corresponding to position 79 of SEQ ID NO:2 is a G79A-substituted human TGF-α.

5. The antibody according to claim 1, which has an activity of suppressing EGFR tyrosine phosphorylation.

6. The antibody according to claim 1, which has an activity of suppressing induction of vascular endothelial cells.

7. A DNA encoding the antibody according to claim 1.

8. A hybridoma comprising the DNA according to claim 7.

9. An expression vector comprising the DNA of claim 7.

10. A host cell transformed with the expression vector of claim 9.

11. A method of producing an antibody, comprising culturing the host cell of claim 10, and purifying the antibody expressed by the expression vector.

12. A hybridoma producing the antibody according to claim 1.

13. A composition comprising the antibody according to claim 1, and a pharmaceutically acceptable carrier.

14. An antibody that specifically binds to human TGF-α, wherein the antibody comprises any one of the following characteristics (a) to (h):
   (a) a light chain variable region including the amino acid sequence of SEQ ID NO: 3, and
   a heavy chain variable region including the amino acid sequence of SEQ ID NO: 4;
   (b) a light chain variable region including the amino acid sequence of SEQ ID NO: 5, and
   a heavy chain variable region including the amino acid sequence of SEQ ID NO: 6;
   (c) a light chain variable region including the amino acid sequence of SEQ ID NO: 7, and
   a heavy chain variable region including the amino acid sequence of SEQ ID NO: 8;

(d) a light chain variable region including the amino acid sequence of SEQ ID NO: 9, and
a heavy chain variable region including the amino acid sequence of SEQ ID NO: 10;
(e) a light chain variable region including the amino acid sequence of SEQ ID NO: 11, and
a heavy chain variable region including the amino acid sequence of SEQ ID NO: 12;
(f) a light chain variable region including the amino acid sequence of SEQ ID NO: 13, and
a heavy chain variable region including the amino acid sequence of SEQ ID NO: 14;
(g) a light chain variable region including the amino acid sequence of SEQ ID NO: 15, and
a heavy chain variable region including the amino acid sequence of SEQ ID NO: 16; and
(h) a light chain variable region including the amino acid sequence of SEQ ID NO: 17, and
a heavy chain variable region including the amino acid sequence of SEQ ID NO: 18.

15. A DNA encoding the antibody according to claim 14.

16. An expression vector comprising the DNA of claim 15.

17. A host cell transformed with the expression vector of claim 16.

18. A method of producing an antibody, comprising culturing the host cell of claim 17, and purifying the antibody expressed by the expression vector.

19. An antibody produced by a hybridoma specified under an accession number of FERM ABP-11377.

* * * * *

SEQUENCE LISTING

<160> NUMBER OF SEQ ID NOS: 173

<210> SEQ ID NO 1
<211> LENGTH: 483
<212> TYPE: DNA

<213> ORGANISM: Homo sapiens
<220> FEATURE:
<221> NAME/KEY: CDS
<222> LOCATION: (1)..(480)

<400> SEQUENCE: 1

```
atg gtc ccc tcg gct gga cag ctc gcc ctg ttc gct ctg ggt att gtg    48
Met Val Pro Ser Ala Gly Gln Leu Ala Leu Phe Ala Leu Gly Ile Val
1               5                   10                  15 ttg gct gcg tgc cag gcc ttg gag aac agc acg tcc ccg ctg agt gca    96
Leu Ala Ala Cys Gln Ala Leu Glu Asn Ser Thr Ser Pro Leu Ser Ala
                20                  25                  30 gac ccg ccc gtg gct gca gca gtg gtg tcc cat ttt aat gac tgc cca   144
Asp Pro Pro Val Ala Ala Ala Val Val Ser His Phe Asn Asp Cys Pro
            35                  40                  45 gat tcc cac act cag ttc tgc ttc cat gga acc tgc agg ttt ttg gtg   192
Asp Ser His Thr Gln Phe Cys Phe His Gly Thr Cys Arg Phe Leu Val
        50                  55                  60 cag gag gac aag cca gca tgt gtc tgc cat tct ggg tac gtt ggt gca   240
Gln Glu Asp Lys Pro Ala Cys Val Cys His Ser Gly Tyr Val Gly Ala
65                  70                  75                  80 cgc tgt gag cat gcg gac ctc ctg gcc gtg gtg gct gcc agc cag aag   288
Arg Cys Glu His Ala Asp Leu Leu Ala Val Val Ala Ala Ser Gln Lys
                85                  90                  95 aag cag gcc atc acc gcc ttg gtg gtg gtc tcc atc gtg gcc ctg gct   336
Lys Gln Ala Ile Thr Ala Leu Val Val Val Ser Ile Val Ala Leu Ala
                100                 105                 110 gtc ctt atc atc aca tgt gtg ctg ata cac tgc tgc cag gtc cga aaa   384
Val Leu Ile Ile Thr Cys Val Leu Ile His Cys Cys Gln Val Arg Lys
            115                 120                 125 cac tgt gag tgg tgc cgg gcc ctc atc tgc cgg cac gag aag ccc agc   432
His Cys Glu Trp Cys Arg Ala Leu Ile Cys Arg His Glu Lys Pro Ser
        130                 135                 140 gcc ctc ctg aag gga aga acc gct tgc tgc cac tca gaa aca gtg gtc   480
Ala Leu Leu Lys Gly Arg Thr Ala Cys Cys His Ser Glu Thr Val Val
145                 150                 155                 160 tga                                                                483
```

<210> SEQ ID NO 2
<211> LENGTH: 160
<212> TYPE: PRT
<213> ORGANISM: Homo sapiens

<400> SEQUENCE: 2

```
Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Ala Val Val Ser His Phe Asn Asp Cys Pro
            35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
                100                 105                 110

Val Leu Ile Ile Thr Cys Val Leu Ile His Cys Cys Gln Val Arg Lys
```

```
              115                 120                 125
    His Cys Glu Trp Cys Arg Ala Leu Ile Cys Arg His Glu Lys Pro Ser
        130                 135                 140
    Ala Leu Leu Lys Gly Arg Thr Ala Cys Cys His Ser Glu Thr Val Val
    145                 150                 155                 160

<210> SEQ ID NO 3
<211> LENGTH: 107
<212> TYPE: PRT
<213> ORGANISM: Mus musculus
<220> FEATURE:
<221> NAME/KEY: DOMAIN
<222> LOCATION: (1)..(107)
<223> OTHER INFORMATION: MBL009-15 VL

<400> SEQUENCE: 3

Asp Ile Gln Met Thr Gln Thr Thr Ser Ser Leu Ser Ala Ser Leu Gly
1               5                  10                  15

Asp Arg Leu Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 4
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: MBL009-15 VH

<400> SEQUENCE: 4

Val Gln Leu Gln Glu Ser Gly Pro Gly Leu Val Lys Pro Ser Gln Ser
1               5                  10                  15

Leu Ser Leu Thr Cys Thr Val Thr Gly Tyr Ser Ile Thr Ser Asp Tyr
            20                  25                  30

Ala Trp Asn Trp Ile Arg Gln Phe Pro Gly Asn Lys Leu Glu Trp Met
        35                  40                  45

Gly Tyr Ile Ser Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Gly Gly Ile Thr Arg Phe Ala Tyr Trp Gly Gln Gly Thr Leu Val
            100                 105                 110

Thr Val Ser Ala
        115

<210> SEQ ID NO 5
```

```
<211> LENGTH: 107
<212> TYPE: PRT
<213> ORGANISM: Mus musculus
<220> FEATURE:
<221> NAME/KEY: DOMAIN
<222> LOCATION: (1)..(107)
<223> OTHER INFORMATION: MBL016-8 VL

<400> SEQUENCE: 5

Asp Ile Gln Met Thr Gln Ser Pro Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Phe Ile
            35                  40                  45

His Tyr Thr Ser Lys Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys
            100                 105

<210> SEQ ID NO 6
<211> LENGTH: 112
<212> TYPE: PRT
<213> ORGANISM: Mus musculus
<220> FEATURE:
<221> NAME/KEY: DOMAIN
<222> LOCATION: (1)..(112)
<223> OTHER INFORMATION: MBL016-8 VH

<400> SEQUENCE: 6

Val Gln Leu Gln Gln Ser Gly Ala Glu Leu Val Arg Pro Gly Ala Ser
1               5                   10                  15

Val Lys Leu Ser Cys Thr Ala Ser Gly Phe Asn Ile Lys Asp Asp Tyr
            20                  25                  30

Met Tyr Trp Val Lys Gln Arg Pro Glu Gln Gly Leu Glu Trp Ile Gly
            35                  40                  45

Arg Ile Asp Pro Ala Asn Gly Asn Thr Lys Tyr Ala Pro Lys Phe Gln
    50                  55                  60

Asp Lys Ala Thr Ile Thr Ala Asp Thr Ser Ser Asn Thr Ala Tyr Leu
65                  70                  75                  80

His Leu Ser Ser Leu Thr Ser Glu Asp Thr Ala Val Phe Tyr Cys Ala
                85                  90                  95

Tyr Arg Arg Ala Tyr Trp Gly Gln Gly Thr Leu Val Thr Val Ser Ala
            100                 105                 110

<210> SEQ ID NO 7
<211> LENGTH: 106
<212> TYPE: PRT
<213> ORGANISM: Mus musculus
<220> FEATURE:
<221> NAME/KEY: DOMAIN
<222> LOCATION: (1)..(106)
<223> OTHER INFORMATION: MBL018-1 VL

<400> SEQUENCE: 7

Ile Val Met Thr Gln Thr Pro Lys Leu Leu Pro Val Ser Ala Gly Asp
1               5                   10                  15
```

Arg Val Thr Met Thr Cys Lys Ala Ser Gln Ser Val Asp Asn Ser Val
            20                  25                  30

Ala Trp Tyr Gln Gln Lys Pro Gly Gln Ser Pro Lys Leu Leu Ile Phe
            35                  40                  45

Tyr Ala Ser Asn His Tyr Thr Gly Val Pro Asp Arg Phe Thr Ala Ser
50                  55                  60

Gly Ser Gly Thr Asp Phe Thr Phe Thr Ile Ser Ser Val Gln Val Glu
65                  70                  75                  80

Asp Leu Ala Val Tyr Phe Cys Gln Gln His Phe Ser Ser Pro Arg Thr
                85                  90                  95

Phe Gly Gly Gly Thr Lys Leu Glu Ile Arg
            100                 105

<210> SEQ ID NO 8
<211> LENGTH: 115
<212> TYPE: PRT
<213> ORGANISM: Mus musculus
<220> FEATURE:
<221> NAME/KEY: DOMAIN
<222> LOCATION: (1)..(115)
<223> OTHER INFORMATION: MBL018-1 VH

<400> SEQUENCE: 8

Glu Val Gln Leu Gln Gln Ser Gly Thr Val Leu Thr Arg Pro Gly Ala
1               5                   10                  15

Ser Val Lys Met Ser Cys Lys Ala Ser Gly Tyr Thr Phe Thr Asn Phe
            20                  25                  30

Trp Ile His Trp Val Lys Gln Arg Pro Gly Gln Gly Leu Asp Trp Ile
            35                  40                  45

Gly Ala Ile Tyr Pro Gly Asn Thr Asn Thr Asp Tyr Asn Gln Lys Phe
50                  55                  60

Gln Gly Lys Ala Lys Leu Thr Ala Val Ser Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Gly Ala Met Asp Tyr Trp Gly Gln Gly Thr Ser Val Thr
            100                 105                 110

Val Ser Ser
        115

<210> SEQ ID NO 9
<211> LENGTH: 107
<212> TYPE: PRT
<213> ORGANISM: Mus musculus
<220> FEATURE:
<221> NAME/KEY: DOMAIN
<222> LOCATION: (1)..(107)
<223> OTHER INFORMATION: MBL144-1 VL

<400> SEQUENCE: 9

Asp Ile Leu Met Thr Gln Ser Pro Ala Thr Leu Ser Val Thr Pro Gly
1               5                   10                  15

Glu Thr Val Ser Leu Ser Cys Arg Ala Ser Gln Asn Thr Tyr Lys Asn
            20                  25                  30

Leu His Trp Tyr Gln Gln Lys Ser His Gly Thr Pro Lys Leu Leu Ile
            35                  40                  45

Lys Tyr Ala Ser Ala Pro Ile Ser Gly Ile Pro Ser Arg Phe Thr Gly
            50                  55                  60

Ser Gly Ser Gly Thr Asp Tyr Thr Leu Ser Ile Asn Ser Val Lys Pro

```
                 65                   70                   75                   80
Glu Asp Glu Gly Ile Tyr Tyr Cys Leu Gln Gly Tyr Ser Met Pro Trp
                 85                   90                   95

Thr Phe Gly Gly Gly Thr Lys Leu Glu Ile Lys
                100                  105
```

```
<210> SEQ ID NO 10
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: 144-1 VH

<400> SEQUENCE: 10

Val Gln Leu Gln Glu Ser Gly Pro Gly Leu Ala Lys Pro Ser Gln Thr
1               5                   10                  15

Leu Ser Leu Thr Cys Ser Val Thr Gly Tyr Ser Ile Thr Ser Asp Tyr
                20                  25                  30

Trp Asn Trp Ile Arg Lys Phe Pro Gly Asn Lys Leu Glu Tyr Met Gly
            35                  40                  45

Tyr Ile Ser Tyr Ser Gly Ser Thr Tyr Tyr Asn Pro Ser Leu Lys Ser
        50                  55                  60

Arg Ile Ser Ile Thr Arg Asp Thr Ser Lys Asn Gln Tyr Tyr Leu Gln
65                  70                  75                  80

Leu Asn Ser Val Thr Thr Glu Asp Thr Ala Thr Tyr Tyr Cys Ala Arg
                85                  90                  95

Ser Tyr Asp Gly Ile Cys Phe Asp Asn Trp Gly Gln Gly Thr Thr Leu
                100                 105                 110

Thr Val Ser Ser
            115
```

```
<210> SEQ ID NO 11
<211> LENGTH: 106
<212> TYPE: PRT
<213> ORGANISM: Mus musculus
<220> FEATURE:
<221> NAME/KEY: DOMAIN
<222> LOCATION: (1)..(106)
<223> OTHER INFORMATION: MBL184-6 VL

<400> SEQUENCE: 11

Ile Gln Met Thr Gln Ser Ser Ser Leu Ser Val Ser Leu Gly Asp
1               5                   10                  15

Arg Val Thr Ile Thr Cys Lys Ala Ser Glu His Ile Asn Ser Trp Leu
                20                  25                  30

Ala Trp Tyr Gln Gln Lys Pro Gly Asn Ala Pro Arg Leu Leu Ile Ser
            35                  40                  45

Gly Ala Thr Asn Leu Lys Thr Gly Val Pro Ser Arg Phe Ser Gly Ser
        50                  55                  60

Ala Ser Gly Lys Asp Tyr Thr Leu Asn Ile Thr Ser Leu Gln Thr Glu
65                  70                  75                  80

Asp Val Ala Thr Tyr Tyr Cys Gln Gln Tyr Trp Gly Thr Pro Trp Thr
                85                  90                  95

Phe Gly Gly Gly Thr Lys Leu Glu Ile Lys
                100                 105
```

```
<210> SEQ ID NO 12
```

```
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: MBL184-6 VH

<400> SEQUENCE: 12

Glu Val Gln Leu Gln Gln Ser Gly Ala Glu Leu Val Arg Pro Gly Ala
1               5                   10                  15

Ser Val Lys Leu Ser Cys Thr Val Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Arg Ile Asp Pro Ala Asn Gly His Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Thr Arg Met Gly Leu Arg Arg Gly Tyr Trp Gly Gln Gly Thr Thr Leu
            100                 105                 110

Thr Val Ser Ser
        115

<210> SEQ ID NO 13
<211> LENGTH: 112
<212> TYPE: PRT
<213> ORGANISM: Mus musculus
<220> FEATURE:
<221> NAME/KEY: DOMAIN
<222> LOCATION: (1)..(112)
<223> OTHER INFORMATION: MBL259-3 VL

<400> SEQUENCE: 13

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Arg
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Tyr Thr Phe Gly Ser Gly Thr Lys Leu Glu Ile Lys
            100                 105                 110

<210> SEQ ID NO 14
<211> LENGTH: 114
<212> TYPE: PRT
<213> ORGANISM: Mus musculus
<220> FEATURE:
<221> NAME/KEY: DOMAIN
<222> LOCATION: (1)..(114)
<223> OTHER INFORMATION: MBL259-3 VH

<400> SEQUENCE: 14
```

-continued

```
Val Gln Leu Gln Gln Ser Gly Ala Glu Leu Val Arg Pro Gly Ala Ser
1               5                   10                  15

Val Lys Leu Ser Cys Thr Ala Ser Asp Phe Asn Ile Lys Asp Asp Tyr
            20                  25                  30

Met His Trp Met Lys Gln Arg Pro Glu Gln Gly Leu Glu Trp Ile Gly
        35                  40                  45

Arg Ile Asp Pro Ala Asn Gly Asn Thr Lys Tyr Ala Pro Lys Phe Gln
50                  55                  60

Asp Lys Ala Thr Met Thr Ala Asp Thr Ser Ser Asn Thr Ala Tyr Leu
65                  70                  75                  80

Gln Phe Ser Ser Leu Thr Ser Glu Asp Thr Ala Val Tyr Tyr Cys Ala
                85                  90                  95

Thr Ser Trp Gly Phe Pro Tyr Trp Gly Gln Gly Thr Leu Val Thr Val
            100                 105                 110

Ser Ala

<210> SEQ ID NO 15
<211> LENGTH: 106
<212> TYPE: PRT
<213> ORGANISM: Mus musculus
<220> FEATURE:
<221> NAME/KEY: DOMAIN
<222> LOCATION: (1)..(106)
<223> OTHER INFORMATION: MBL292-1 VL

<400> SEQUENCE: 15

Ile Gln Met Thr Gln Ser Ser Ser Leu Ser Val Ser Leu Gly Asp
1               5                   10                  15

Arg Val Thr Ile Thr Cys Lys Ala Ser Val His Ile Asn Ser Trp Leu
            20                  25                  30

Ala Trp Tyr Gln Gln Lys Pro Gly Asn Ala Pro Arg Leu Leu Ile Ser
        35                  40                  45

Gly Ala Thr Asn Leu Lys Thr Gly Val Pro Ser Arg Phe Ser Gly Ser
50                  55                  60

Ala Ser Gly Lys Asp Tyr Thr Leu Ser Ile Thr Ser Leu Gln Thr Glu
65                  70                  75                  80

Asp Val Ala Thr Tyr Tyr Cys Gln Gln Tyr Trp Asp Thr Pro Trp Thr
                85                  90                  95

Phe Gly Gly Gly Thr Lys Leu Glu Ile Lys
            100                 105

<210> SEQ ID NO 16
<211> LENGTH: 115
<212> TYPE: PRT
<213> ORGANISM: Mus musculus
<220> FEATURE:
<221> NAME/KEY: DOMAIN
<222> LOCATION: (1)..(115)
<223> OTHER INFORMATION: MBL292-1 VH

<400> SEQUENCE: 16

Val Gln Leu Gln Gln Ser Gly Ala Glu Leu Val Arg Pro Gly Ala Ser
1               5                   10                  15

Val Lys Leu Ser Cys Thr Ala Ser Gly Phe Asn Ile Lys Asp Asp Tyr
            20                  25                  30

Met His Trp Met Lys Gln Arg Pro Glu Gln Gly Leu Glu Trp Ile Gly
        35                  40                  45

Arg Ile Asp Pro Ala Asn Gly Asn Thr Lys Tyr Ala Pro Lys Phe Gln
50                  55                  60
```

```
Asp Lys Ala Thr Ile Thr Ala Asp Thr Ser Ser Asn Thr Ala Tyr Leu
 65                  70                  75                  80

Gln Leu Ser Ser Leu Thr Ser Glu Asp Thr Ala Val Tyr Tyr Cys Ser
                 85                  90                  95

Arg Met Gly Leu Leu Arg Gly Tyr Trp Gly Gln Gly Thr Thr Leu Thr
            100                 105                 110

Val Ser Ser
        115
```

<210> SEQ ID NO 17
<211> LENGTH: 106
<212> TYPE: PRT
<213> ORGANISM: Mus musculus
<220> FEATURE:
<221> NAME/KEY: DOMAIN
<222> LOCATION: (1)..(106)
<223> OTHER INFORMATION: MBL352-34 VL

<400> SEQUENCE: 17

```
Ile Gln Met Thr Gln Ser Ser Ser Leu Ser Val Ser Leu Gly Asp
 1               5                  10                  15

Arg Val Thr Ile Thr Cys Lys Ala Ser Glu His Ile Asn Ser Trp Leu
                 20                  25                  30

Ala Trp Tyr Gln Gln Lys Pro Gly Asn Ala Pro Arg Leu Leu Ile Ser
            35                  40                  45

Gly Ala Thr Asn Leu Lys Thr Gly Val Pro Ser Arg Phe Ser Gly Ser
        50                  55                  60

Ala Ser Gly Lys Asp Tyr Thr Leu Ser Ile Thr Ser Leu Gln Thr Glu
 65                  70                  75                  80

Asp Val Ala Thr Tyr Tyr Cys Gln Gln Tyr Trp Gly Thr Pro Trp Thr
                 85                  90                  95

Phe Gly Gly Gly Thr Lys Leu Glu Ile Lys
            100                 105
```

<210> SEQ ID NO 18
<211> LENGTH: 115
<212> TYPE: PRT
<213> ORGANISM: Mus musculus
<220> FEATURE:
<221> NAME/KEY: DOMAIN
<222> LOCATION: (1)..(115)
<223> OTHER INFORMATION: MBL352-34 VH

<400> SEQUENCE: 18

```
Val Gln Leu Gln Gln Ser Gly Ala Glu Leu Val Arg Pro Gly Ala Ser
 1               5                  10                  15

Val Lys Leu Ser Cys Thr Ala Ser Gly Phe Asn Ile Lys Asp Asp Tyr
                 20                  25                  30

Met His Trp Val Lys Gln Arg Pro Glu Gln Gly Leu Glu Trp Ile Gly
            35                  40                  45

Arg Ile Asp Pro Ala Asn Gly His Thr Lys Tyr Ala Pro Lys Phe Gln
        50                  55                  60

Asp Lys Ala Thr Ile Thr Ala Asp Thr Ser Ser Asn Thr Ala Tyr Leu
 65                  70                  75                  80

Gln Phe Ser Ser Leu Thr Ser Glu Asp Thr Ala Val Tyr Tyr Cys Thr
                 85                  90                  95

Arg Met Gly Leu Arg Arg Gly Tyr Trp Gly Gln Gly Thr Thr Leu Thr
            100                 105                 110
```

Val Ser Ser
        115

<210> SEQ ID NO 19
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL009-15 VL CDR1

<400> SEQUENCE: 19

Arg Ala Ser Gln Asp Ile Arg Asn Tyr Leu Asn
1               5                   10

<210> SEQ ID NO 20
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL009-15 VL CDR2

<400> SEQUENCE: 20

Tyr Thr Ser Arg Leu His Ser
1               5

<210> SEQ ID NO 21
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL009-15 VL CDR3

<400> SEQUENCE: 21

Gln Gln Gly Asn Thr Leu Pro
1               5

<210> SEQ ID NO 22
<211> LENGTH: 6
<212> TYPE: PRT
<213> ORGANISM: Mus musculus
<220> FEATURE:
<221> NAME/KEY: DOMAIN
<222> LOCATION: (1)..(6)
<223> OTHER INFORMATION: MBL009-15 VH CDR1

<400> SEQUENCE: 22

Ser Asp Tyr Ala Trp Asn
1               5

<210> SEQ ID NO 23
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: MBL009-15 VH CDR2

<400> SEQUENCE: 23

Tyr Ile Ser Tyr Ser Gly Ser Thr Ser Tyr Asn Pro Ser Leu Lys Ser
1               5                   10                  15

```
<210> SEQ ID NO 24
<211> LENGTH: 8
<212> TYPE: PRT
<213> ORGANISM: Mus musculus
<220> FEATURE:
<221> NAME/KEY: DOMAIN
<222> LOCATION: (1)..(8)
<223> OTHER INFORMATION: MBL009-15 VH CDR3

<400> SEQUENCE: 24

Gly Gly Ile Thr Arg Phe Ala Tyr
1               5

<210> SEQ ID NO 25
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL016-8 VL CDR1

<400> SEQUENCE: 25

Lys Ala Ser Gln Asp Ile Asn Lys Tyr Ile Ala
1               5                   10

<210> SEQ ID NO 26
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL016-8 VL CDR2

<400> SEQUENCE: 26

Tyr Thr Ser Lys Leu Gln Pro
1               5

<210> SEQ ID NO 27
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL016-8 VL CDR3

<400> SEQUENCE: 27

Leu Gln Tyr Asp Asn Leu Leu
1               5

<210> SEQ ID NO 28
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MBL016-8 VH CDR1

<400> SEQUENCE: 28

Asp Asp Tyr Met Tyr
1               5

<210> SEQ ID NO 29
<211> LENGTH: 17
<212> TYPE: PRT
<213> ORGANISM: Mus musculus
```

```
<220> FEATURE:
<221> NAME/KEY: DOMAIN
<222> LOCATION: (1)..(17)
<223> OTHER INFORMATION: MBL016-8 VH CDR2

<400> SEQUENCE: 29

Arg Ile Asp Pro Ala Asn Gly Asn Thr Lys Tyr Ala Pro Lys Phe Gln
1               5                   10                  15

Asp

<210> SEQ ID NO 30
<211> LENGTH: 4
<212> TYPE: PRT
<213> ORGANISM: Mus musculus
<220> FEATURE:
<221> NAME/KEY: DOMAIN
<222> LOCATION: (1)..(4)
<223> OTHER INFORMATION: MBL016-8 VH CDR3

<400> SEQUENCE: 30

Arg Arg Ala Tyr
1

<210> SEQ ID NO 31
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL018-1 VL CDR1

<400> SEQUENCE: 31

Lys Ala Ser Gln Ser Val Asp Asn Ser Val Ala
1               5                   10

<210> SEQ ID NO 32
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL018-1 VL CDR2

<400> SEQUENCE: 32

Tyr Ala Ser Asn His Tyr Thr
1               5

<210> SEQ ID NO 33
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL018-1 VL CDR3

<400> SEQUENCE: 33

Gln Gln His Phe Ser Ser Pro
1               5

<210> SEQ ID NO 34
<211> LENGTH: 5
<212> TYPE: PRT
<213> ORGANISM: Mus musculus
<220> FEATURE:
<221> NAME/KEY: DOMAIN
```

```
<222> LOCATION: (1)..(5)
<223> OTHER INFORMATION: MBL018-1 VH CDR1

<400> SEQUENCE: 34

Asn Phe Trp Ile His
1               5

<210> SEQ ID NO 35
<211> LENGTH: 17
<212> TYPE: PRT
<213> ORGANISM: Mus musculus
<220> FEATURE:
<221> NAME/KEY: DOMAIN
<222> LOCATION: (1)..(17)
<223> OTHER INFORMATION: MBL018-1 VH CDR2

<400> SEQUENCE: 35

Ala Ile Tyr Pro Gly Asn Thr Asn Thr Asp Tyr Asn Gln Lys Phe Gln
1               5                   10                  15

Gly

<210> SEQ ID NO 36
<211> LENGTH: 6
<212> TYPE: PRT
<213> ORGANISM: Mus musculus
<220> FEATURE:
<221> NAME/KEY: DOMAIN
<222> LOCATION: (1)..(6)
<223> OTHER INFORMATION: MBL018-1 VH CDR3

<400> SEQUENCE: 36

Gly Gly Ala Met Asp Tyr
1               5

<210> SEQ ID NO 37
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL144- VL CDR1

<400> SEQUENCE: 37

Arg Ala Ser Gln Asn Thr Tyr Lys Asn Leu His
1               5                   10

<210> SEQ ID NO 38
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL144- VL CDR2

<400> SEQUENCE: 38

Tyr Ala Ser Ala Pro Ile Ser
1               5

<210> SEQ ID NO 39
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL144- VL CDR3
```

```
<400> SEQUENCE: 39

Leu Gln Gly Tyr Ser Met Pro
1               5

<210> SEQ ID NO 40
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MBL144-1 VH CDR1

<400> SEQUENCE: 40

Ser Asp Tyr Trp Asn
1               5

<210> SEQ ID NO 41
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: MBL144-1 VH CDR2

<400> SEQUENCE: 41

Tyr Ile Ser Tyr Ser Gly Ser Thr Tyr Tyr Asn Pro Ser Leu Lys Ser
1               5                   10                  15

<210> SEQ ID NO 42
<211> LENGTH: 9
<212> TYPE: PRT
<213> ORGANISM: Mus musculus
<220> FEATURE:
<221> NAME/KEY: DOMAIN
<222> LOCATION: (1)..(9)
<223> OTHER INFORMATION: MBL144-1 VH CDR3

<400> SEQUENCE: 42

Ser Tyr Asp Gly Ile Cys Phe Asp Asn
1               5

<210> SEQ ID NO 43
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL184-6 VL CDR1

<400> SEQUENCE: 43

Lys Ala Ser Glu His Ile Asn Ser Trp Leu Ala
1               5                   10

<210> SEQ ID NO 44
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL184-6 VL CDR2

<400> SEQUENCE: 44

Gly Ala Thr Asn Leu Lys Thr
```

```
<210> SEQ ID NO 45
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL184-6 VL CDR3

<400> SEQUENCE: 45

Gln Gln Tyr Trp Gly Thr Pro
1               5

<210> SEQ ID NO 46
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MBL184-6 VH CDR1

<400> SEQUENCE: 46

Asp Asp Tyr Met His
1               5

<210> SEQ ID NO 47
<211> LENGTH: 17
<212> TYPE: PRT
<213> ORGANISM: Mus musculus
<220> FEATURE:
<221> NAME/KEY: DOMAIN
<222> LOCATION: (1)..(17)
<223> OTHER INFORMATION: MBL184-6 VH CDR2

<400> SEQUENCE: 47

Arg Ile Asp Pro Ala Asn Gly His Thr Lys Tyr Ala Pro Lys Phe Gln
1               5                   10                  15

Asp

<210> SEQ ID NO 48
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL184-6 VH CDR3

<400> SEQUENCE: 48

Met Gly Leu Arg Arg Gly Tyr
1               5

<210> SEQ ID NO 49
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: MBL259-3 VL CDR1

<400> SEQUENCE: 49

Arg Ser Ser Lys Ser Leu Leu His Arg Asn Gly Asn Thr Tyr Leu Tyr
1               5                   10                  15
```

```
<210> SEQ ID NO 50
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL259-3 VL CDR2

<400> SEQUENCE: 50

Arg Met Ser Asn Leu Ala Ser
1               5

<210> SEQ ID NO 51
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL259-3 VL CDR3

<400> SEQUENCE: 51

Leu Gln His Leu Glu Tyr Pro
1               5

<210> SEQ ID NO 52
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MBL259-3 VH CDR1

<400> SEQUENCE: 52

Asp Asp Tyr Met His
1               5

<210> SEQ ID NO 53
<211> LENGTH: 17
<212> TYPE: PRT
<213> ORGANISM: Mus musculus
<220> FEATURE:
<221> NAME/KEY: DOMAIN
<222> LOCATION: (1)..(17)
<223> OTHER INFORMATION: MBL259-3 VH CDR2

<400> SEQUENCE: 53

Arg Ile Asp Pro Ala Asn Gly Asn Thr Lys Tyr Ala Pro Lys Phe Gln
1               5                   10                  15

Asp

<210> SEQ ID NO 54
<211> LENGTH: 6
<212> TYPE: PRT
<213> ORGANISM: Mus musculus
<220> FEATURE:
<221> NAME/KEY: DOMAIN
<222> LOCATION: (1)..(6)
<223> OTHER INFORMATION: MBL259-3 VH CDR3

<400> SEQUENCE: 54

Ser Trp Gly Phe Pro Tyr
1               5

<210> SEQ ID NO 55
```

```
<210> SEQ ID NO 55
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL292-1 VL CDR1

<400> SEQUENCE: 55

Lys Ala Ser Val His Ile Asn Ser Trp Leu Ala
1               5                   10

<210> SEQ ID NO 56
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL292-1 VL CDR2

<400> SEQUENCE: 56

Gly Ala Thr Asn Leu Lys Thr
1               5

<210> SEQ ID NO 57
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL292-1 VL CDR3

<400> SEQUENCE: 57

Gln Gln Tyr Trp Asp Thr Pro
1               5

<210> SEQ ID NO 58
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MBL292-1 VH CDR1

<400> SEQUENCE: 58

Asp Asp Tyr Met His
1               5

<210> SEQ ID NO 59
<211> LENGTH: 17
<212> TYPE: PRT
<213> ORGANISM: Mus musculus
<220> FEATURE:
<221> NAME/KEY: DOMAIN
<222> LOCATION: (1)..(17)
<223> OTHER INFORMATION: MBL292-1 VH CDR2

<400> SEQUENCE: 59

Arg Ile Asp Pro Ala Asn Gly Asn Thr Lys Tyr Ala Pro Lys Phe Gln
1               5                   10                  15

Asp

<210> SEQ ID NO 60
<211> LENGTH: 7
<212> TYPE: PRT
```

```
<213> ORGANISM: Mus musculus
<220> FEATURE:
<221> NAME/KEY: DOMAIN
<222> LOCATION: (1)..(7)
<223> OTHER INFORMATION: MBL292-1 VH CDR3

<400> SEQUENCE: 60

Met Gly Leu Leu Arg Gly Tyr
1               5

<210> SEQ ID NO 61
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: MBL352-34 VL CDR1

<400> SEQUENCE: 61

Lys Ala Ser Glu His Ile Asn Ser Trp Leu Ala
1               5                   10

<210> SEQ ID NO 62
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL352-34 VL CDR2

<400> SEQUENCE: 62

Gly Ala Thr Asn Leu Lys Thr
1               5

<210> SEQ ID NO 63
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL352-34 VL CDR3

<400> SEQUENCE: 63

Gln Gln Tyr Trp Gly Thr Pro
1               5

<210> SEQ ID NO 64
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MBL352-34 VH CDR1

<400> SEQUENCE: 64

Asp Asp Tyr Met His
1               5

<210> SEQ ID NO 65
<211> LENGTH: 17
<212> TYPE: PRT
<213> ORGANISM: Mus musculus
<220> FEATURE:
<221> NAME/KEY: DOMAIN
<222> LOCATION: (1)..(17)
```

```
<223> OTHER INFORMATION: MBL352-34 VH CDR2

<400> SEQUENCE: 65

Arg Ile Asp Pro Ala Asn Gly His Thr Lys Tyr Ala Pro Lys Phe Gln
1               5                   10                  15

Asp

<210> SEQ ID NO 66
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MBL352-34 VH CDR3

<400> SEQUENCE: 66

Met Gly Leu Arg Arg Gly Tyr
1               5

<210> SEQ ID NO 67
<211> LENGTH: 9
<212> TYPE: PRT
<213> ORGANISM: Artificial
<220> FEATURE:
<223> OTHER INFORMATION: An artificially synthesized peptide sequence;
      OLP-1

<400> SEQUENCE: 67

Val Val Ser His Phe Asn Asp Cys Pro
1               5

<210> SEQ ID NO 68
<211> LENGTH: 15
<212> TYPE: PRT
<213> ORGANISM: Artificial
<220> FEATURE:
<223> OTHER INFORMATION: An artificially synthesized peptide sequence;
      OLP-2

<400> SEQUENCE: 68

Val Val Ser His Phe Asn Asp Cys Pro Asp Ser His Thr Gln Phe
1               5                   10                  15

<210> SEQ ID NO 69
<211> LENGTH: 8
<212> TYPE: PRT
<213> ORGANISM: Artificial
<220> FEATURE:
<223> OTHER INFORMATION: An artificially synthesized peptide sequence;
      OLP-3

<400> SEQUENCE: 69

Pro Asp Ser His Thr Gln Phe Cys
1               5

<210> SEQ ID NO 70
<211> LENGTH: 10
<212> TYPE: PRT
<213> ORGANISM: Artificial
<220> FEATURE:
<223> OTHER INFORMATION: An artificially synthesized peptide sequence;
      OLP-4

<400> SEQUENCE: 70

Ser His Thr Gln Phe Cys Phe His Gly Thr
1               5                   10
```

<210> SEQ ID NO 71
<211> LENGTH: 11
<212> TYPE: PRT
<213> ORGANISM: Artificial
<220> FEATURE:
<223> OTHER INFORMATION: An artificially synthesized peptide sequence;
      OLP-5

<400> SEQUENCE: 71

Phe His Gly Thr Cys Arg Phe Leu Val Gln Glu
1               5                   10

<210> SEQ ID NO 72
<211> LENGTH: 15
<212> TYPE: PRT
<213> ORGANISM: Artificial
<220> FEATURE:
<223> OTHER INFORMATION: An artificially synthesized peptide sequence;
      OLP-6

<400> SEQUENCE: 72

Phe His Gly Thr Cys Arg Phe Leu Val Gln Glu Asp Lys Pro Ala
1               5                   10                  15

<210> SEQ ID NO 73
<211> LENGTH: 12
<212> TYPE: PRT
<213> ORGANISM: Artificial
<220> FEATURE:
<223> OTHER INFORMATION: An artificially synthesized peptide sequence;
      OLP-7

<400> SEQUENCE: 73

Arg Phe Leu Val Gln Glu Asp Lys Pro Ala Cys Val
1               5                   10

<210> SEQ ID NO 74
<211> LENGTH: 10
<212> TYPE: PRT
<213> ORGANISM: Artificial
<220> FEATURE:
<223> OTHER INFORMATION: An artificially synthesized peptide sequence;
      OLP-8

<400> SEQUENCE: 74

Val Cys His Ser Gly Tyr Val Gly Ala Arg
1               5                   10

<210> SEQ ID NO 75
<211> LENGTH: 16
<212> TYPE: PRT
<213> ORGANISM: Artificial
<220> FEATURE:
<223> OTHER INFORMATION: An artificially synthesized peptide sequence;
      OLP-9

<400> SEQUENCE: 75

His Ser Gly Tyr Val Gly Ala Arg Cys Glu His Ala Asp Leu Leu Ala
1               5                   10                  15

<210> SEQ ID NO 76
<211> LENGTH: 13
<212> TYPE: PRT
<213> ORGANISM: Artificial
<220> FEATURE:
<223> OTHER INFORMATION: An artificially synthesized peptide sequence;
      OLP-10

<400> SEQUENCE: 76

Tyr Val Gly Ala Arg Cys Glu His Ala Asp Leu Leu Ala
1               5                   10

<210> SEQ ID NO 77
<211> LENGTH: 10
<212> TYPE: PRT
<213> ORGANISM: Artificial
<220> FEATURE:
<223> OTHER INFORMATION: An artificially synthesized peptide sequence;
      OLP-11

<400> SEQUENCE: 77

Ala Arg Cys Glu His Ala Asp Leu Leu Ala
1               5                   10

<210> SEQ ID NO 78
<211> LENGTH: 30
<212> TYPE: DNA
<213> ORGANISM: Artificial
<220> FEATURE:
<223> OTHER INFORMATION: An artificially synthesized primer sequence;
      MKV1

<400> SEQUENCE: 78
atgaagttgc ctgttaggct gttggtgctg                                   30

<210> SEQ ID NO 79
<211> LENGTH: 30
<212> TYPE: DNA
<213> ORGANISM: Artificial
<220> FEATURE:
<223> OTHER INFORMATION: An artificially synthesized primer sequence;
      MKV2

<400> SEQUENCE: 79
atggagwcag acacactcct gytatgggtg                                   30

<210> SEQ ID NO 80
<211> LENGTH: 30
<212> TYPE: DNA
<213> ORGANISM: Artificial
<220> FEATURE:
<223> OTHER INFORMATION: An artificially synthesized primer sequence;
      MKV3

<400> SEQUENCE: 80
atgagtgtgc tcactcaggt cctggsgttg                                   30

<210> SEQ ID NO 81
<211> LENGTH: 33
<212> TYPE: DNA
<213> ORGANISM: Artificial
<220> FEATURE:
<223> OTHER INFORMATION: An artificially synthesized primer sequence;
      MKV4

<400> SEQUENCE: 81
atgaggrccc ctgctcagwt tyttggmwtc ttg                               33

<210> SEQ ID NO 82
<211> LENGTH: 30
<212> TYPE: DNA
<213> ORGANISM: Artificial
<220> FEATURE:
<223> OTHER INFORMATION: An artificially synthesized primer sequence;

MKV5

<400> SEQUENCE: 82
atggatttwc aggtgcagat twtcagcttc                                      30

<210> SEQ ID NO 83
<211> LENGTH: 27
<212> TYPE: DNA
<213> ORGANISM: Artificial
<220> FEATURE:
<223> OTHER INFORMATION: An artificially synthesized primer sequence;
      MKV6

<400> SEQUENCE: 83
atgaggtkcy ytgytsagyt yctgrgg                                         27

<210> SEQ ID NO 84
<211> LENGTH: 31
<212> TYPE: DNA
<213> ORGANISM: Artificial
<220> FEATURE:
<223> OTHER INFORMATION: An artificially synthesized primer sequence;
      MKV7

<400> SEQUENCE: 84
atgggcwtca agatggagtc acakwyycwg g                                    31

<210> SEQ ID NO 85
<211> LENGTH: 31
<212> TYPE: DNA
<213> ORGANISM: Artificial
<220> FEATURE:
<223> OTHER INFORMATION: An artificially synthesized primer sequence;
      MKV8

<400> SEQUENCE: 85 atgtgggay ctktttycmm tttttcaatt g                                     31

<210> SEQ ID NO 86
<211> LENGTH: 25
<212> TYPE: DNA
<213> ORGANISM: Artificial
<220> FEATURE:
<223> OTHER INFORMATION: An artificially synthesized primer sequence;
      MKV9

<400> SEQUENCE: 86
atggtrtccw casctcagtt ccttg                                           25

<210> SEQ ID NO 87
<211> LENGTH: 27
<212> TYPE: DNA
<213> ORGANISM: Artificial
<220> FEATURE:
<223> OTHER INFORMATION: An artificially synthesized primer sequence;
      MKV10

<400> SEQUENCE: 87
atgtatatat gtttgttgtc tatttct                                         27

<210> SEQ ID NO 88
<211> LENGTH: 28
<212> TYPE: DNA
<213> ORGANISM: Artificial
<220> FEATURE:
<223> OTHER INFORMATION: An artificially synthesized primer sequence;
      MKV11

<400> SEQUENCE: 88
atggaagccc cagctcagct tctcttcc                28

<210> SEQ ID NO 89
<211> LENGTH: 20
<212> TYPE: DNA
<213> ORGANISM: Artificial
<220> FEATURE:
<223> OTHER INFORMATION: An artificially synthesized primer sequence;
      MKC

<400> SEQUENCE: 89
actggatggt gggaagatgg                20

<210> SEQ ID NO 90
<211> LENGTH: 27
<212> TYPE: DNA
<213> ORGANISM: Artificial
<220> FEATURE:
<223> OTHER INFORMATION: An artificially synthesized primer sequence;
      MHV1

<400> SEQUENCE: 90
atgaaatgca gctggggcat sttcttc                27

<210> SEQ ID NO 91
<211> LENGTH: 26
<212> TYPE: DNA
<213> ORGANISM: Artificial
<220> FEATURE:
<223> OTHER INFORMATION: An artificially synthesized primer sequence;
      MHV2

<400> SEQUENCE: 91
atgggatgga gctrtatcat sytctt                26

<210> SEQ ID NO 92
<211> LENGTH: 27
<212> TYPE: DNA
<213> ORGANISM: Artificial
<220> FEATURE:
<223> OTHER INFORMATION: An artificially synthesized primer sequence;
      MHV3

<400> SEQUENCE: 92
atgaagwtgt ggttaaactg ggttttt                27

<210> SEQ ID NO 93
<211> LENGTH: 25
<212> TYPE: DNA
<213> ORGANISM: Artificial
<220> FEATURE:
<223> OTHER INFORMATION: An artificially synthesized primer sequence;
      MHV4

<400> SEQUENCE: 93
atgractttg ggytcagctt grttt                25

<210> SEQ ID NO 94
<211> LENGTH: 30
<212> TYPE: DNA
<213> ORGANISM: Artificial
<220> FEATURE:
<223> OTHER INFORMATION: An artificially synthesized primer sequence;
      MHV5

```
<400> SEQUENCE: 94
atggactcca ggctcaattt agttttcctt                                           30

<210> SEQ ID NO 95
<211> LENGTH: 27
<212> TYPE: DNA
<213> ORGANISM: Artificial
<220> FEATURE:
<223> OTHER INFORMATION: An artificially synthesized primer sequence;
      MHV6

<400> SEQUENCE: 95
atggctgtcy trgsgctrct cttctgc                                              27

<210> SEQ ID NO 96
<211> LENGTH: 26
<212> TYPE: DNA
<213> ORGANISM: Artificial
<220> FEATURE:
<223> OTHER INFORMATION: An artificially synthesized primer sequence;
      MHV7

<400> SEQUENCE: 96
atggratgga gckggrtctt tmtctt                                               26

<210> SEQ ID NO 97
<211> LENGTH: 23
<212> TYPE: DNA
<213> ORGANISM: Artificial
<220> FEATURE:
<223> OTHER INFORMATION: An artificially synthesized primer sequence;
      MHV8

<400> SEQUENCE: 97
atgagagtgc tgattctttt gtg                                                  23

<210> SEQ ID NO 98
<211> LENGTH: 30
<212> TYPE: DNA
<213> ORGANISM: Artificial
<220> FEATURE:
<223> OTHER INFORMATION: An artificially synthesized primer sequence;
      MHV9

<400> SEQUENCE: 98
atggmttggg tgtggamctt gctattcctg                                           30

<210> SEQ ID NO 99
<211> LENGTH: 27
<212> TYPE: DNA
<213> ORGANISM: Artificial
<220> FEATURE:
<223> OTHER INFORMATION: An artificially synthesized primer sequence;
      MHV10

<400> SEQUENCE: 99
atgggcagac ttacattctc attcctg                                              27

<210> SEQ ID NO 100
<211> LENGTH: 28
<212> TYPE: DNA
<213> ORGANISM: Artificial
<220> FEATURE:
<223> OTHER INFORMATION: An artificially synthesized primer sequence;
      MHV11

<400> SEQUENCE: 100
```

```
atggattttg ggctgatttt ttttattg                                              28

<210> SEQ ID NO 101
<211> LENGTH: 27
<212> TYPE: DNA
<213> ORGANISM: Artificial
<220> FEATURE:
<223> OTHER INFORMATION: An artificially synthesized primer sequence;
      MHV12

<400> SEQUENCE: 101
atgatggtgt aagtcttct gtacctg                                                27

<210> SEQ ID NO 102
<211> LENGTH: 21
<212> TYPE: DNA
<213> ORGANISM: Artificial
<220> FEATURE:
<223> OTHER INFORMATION: An artificially synthesized primer sequence;
      MHCG1

<400> SEQUENCE: 102
cagtggatag acagatgggg g                                                     21

<210> SEQ ID NO 103
<211> LENGTH: 21
<212> TYPE: DNA
<213> ORGANISM: Artificial
<220> FEATURE:
<223> OTHER INFORMATION: An artificially synthesized primer sequence;
      MHCG2a

<400> SEQUENCE: 103
cagtggatag acagatgggg c                                                     21

<210> SEQ ID NO 104
<211> LENGTH: 42
<212> TYPE: DNA
<213> ORGANISM: Artificial
<220> FEATURE:
<223> OTHER INFORMATION: An artificially synthesized primer sequence;
      Human IgG1 CH sense primer

<400> SEQUENCE: 104
aagcttcgta cgcccgctct tcgcctccac caagggccca tc                              42

<210> SEQ ID NO 105
<211> LENGTH: 55
<212> TYPE: DNA
<213> ORGANISM: Artificial
<220> FEATURE:
<223> OTHER INFORMATION: An artificially synthesized primer sequence;
      Human IgG1 CH antisense primer

<400> SEQUENCE: 105
cgcctgacgc gtccctcatt tacccggaga cagggagaga ctcttctgcg tgtag               55

<210> SEQ ID NO 106
<211> LENGTH: 41
<212> TYPE: DNA
<213> ORGANISM: Artificial
<220> FEATURE:
<223> OTHER INFORMATION: An artificially synthesized primer sequence;
      Human IgG1 CL sense primer

<400> SEQUENCE: 106
```
aagcttcgta cgcccgctct tcactgtggc tcaccatctg t                41

<210> SEQ ID NO 107
<211> LENGTH: 35
<212> TYPE: DNA
<213> ORGANISM: Artificial
<220> FEATURE:
<223> OTHER INFORMATION: An artificially synthesized primer sequence;
      Human IgG1 CL antisense primer

<400> SEQUENCE: 107
cgcctgacgc gtcccctaac actctcccct gttga                      35

<210> SEQ ID NO 108
<211> LENGTH: 37
<212> TYPE: DNA
<213> ORGANISM: Artificial
<220> FEATURE:
<223> OTHER INFORMATION: An artificially synthesized primer sequence;
      MBL009-15 H sense primer

<400> SEQUENCE: 108
gcccgctctt cgcctatgag agtgctgatt cttttgt                    37

<210> SEQ ID NO 109
<211> LENGTH: 37
<212> TYPE: DNA
<213> ORGANISM: Artificial
<220> FEATURE:
<223> OTHER INFORMATION: An artificially synthesized primer sequence;
      MBL009-15 H antisense primer

<400> SEQUENCE: 109
ggcccttggt ggaggctgca gagacagtga ccagagt                    37

<210> SEQ ID NO 110
<211> LENGTH: 40
<212> TYPE: DNA
<213> ORGANISM: Artificial
<220> FEATURE:
<223> OTHER INFORMATION: An artificially synthesized primer sequence;
      MBL009-15 L sense primer

<400> SEQUENCE: 110
gcccgctctt cactgatggt gtcctcagct cagttccttg                 40

<210> SEQ ID NO 111
<211> LENGTH: 37
<212> TYPE: DNA
<213> ORGANISM: Artificial
<220> FEATURE:
<223> OTHER INFORMATION: An artificially synthesized primer sequence;
      MBL009-15 L antisense primer

<400> SEQUENCE: 111
atggtgcagc cacagttttg atttccagct tggtgcc                    37

<210> SEQ ID NO 112
<211> LENGTH: 36
<212> TYPE: DNA
<213> ORGANISM: Artificial
<220> FEATURE:
<223> OTHER INFORMATION: An artificially synthesized primer sequence;
      MBL0168 H sense primer

<400> SEQUENCE: 112
gcccgctctt cgcctatgaa atgcagctgg ggcatg                     36

<210> SEQ ID NO 113
<211> LENGTH: 37
<212> TYPE: DNA
<213> ORGANISM: Artificial
<220> FEATURE:
<223> OTHER INFORMATION: An artificially synthesized primer sequence;
    MBL0168 H antisense primer

<400> SEQUENCE: 113
ggcccttggt ggaggctgca gagacagtga ccagagt                    37

<210> SEQ ID NO 114
<211> LENGTH: 36
<212> TYPE: DNA
<213> ORGANISM: Artificial
<220> FEATURE:
<223> OTHER INFORMATION: An artificially synthesized primer sequence;
    MBL0168 L sense pr
    imer

<400> SEQUENCE: 114
gcccgctctt cactgatgag gttctctgtt gagttc                     36

<210> SEQ ID NO 115
<211> LENGTH: 37
<212> TYPE: DNA
<213> ORGANISM: Artificial
<220> FEATURE:
<223> OTHER INFORMATION: An artificially synthesized primer sequence;
    MBL0168 L antisense primer

<400> SEQUENCE: 115
atggtgcagc cacagttttt atttccagct tggtccc                    37

<210> SEQ ID NO 116
<211> LENGTH: 36
<212> TYPE: DNA
<213> ORGANISM: Artificial
<220> FEATURE:
<223> OTHER INFORMATION: An artificially synthesized primer sequence;
    MBL018-1 H sense primer

<400> SEQUENCE: 116
gcccgctctt cgcctatgga atgtaactgg atactt                     36

<210> SEQ ID NO 117
<211> LENGTH: 37
<212> TYPE: DNA
<213> ORGANISM: Artificial
<220> FEATURE:
<223> OTHER INFORMATION: An artificially synthesized primer sequence;
    MBL018-1 H antisense primer

<400> SEQUENCE: 117
ggcccttggt ggaggctgag gagacggtga ctgaggt                    37

<210> SEQ ID NO 118
<211> LENGTH: 36
<212> TYPE: DNA
<213> ORGANISM: Artificial
<220> FEATURE:
<223> OTHER INFORMATION: An artificially synthesized primer sequence;
    MBL018-1 L sense primer

<400> SEQUENCE: 118
gcccgctctt cactgatggg catcaagatg gagtca                     36

<210> SEQ ID NO 119
<211> LENGTH: 37
<212> TYPE: DNA
<213> ORGANISM: Artificial
<220> FEATURE:
<223> OTHER INFORMATION: An artificially synthesized primer sequence;
      MBL018-1 L antisense primer

<400> SEQUENCE: 119
atggtgcagc cacagttctg atttccagtt tggtgcc                              37

<210> SEQ ID NO 120
<211> LENGTH: 36
<212> TYPE: DNA
<213> ORGANISM: Artificial
<220> FEATURE:
<223> OTHER INFORMATION: An artificially synthesized primer sequence;
      MBL144-1 H sense primer

<400> SEQUENCE: 120
gcccgctctt cgcctatgat ggtgttaagt cttctg                               36

<210> SEQ ID NO 121
<211> LENGTH: 37
<212> TYPE: DNA
<213> ORGANISM: Artificial
<220> FEATURE:
<223> OTHER INFORMATION: An artificially synthesized primer sequence;
      MBL144-1 H antisense primer

<400> SEQUENCE: 121
ggcccttggt ggaggctgag gagactgtga gagtggt                              37

<210> SEQ ID NO 122
<211> LENGTH: 36
<212> TYPE: DNA
<213> ORGANISM: Artificial
<220> FEATURE:
<223> OTHER INFORMATION: An artificially synthesized primer sequence;
      MBL144-1 L sense primer

<400> SEQUENCE: 122
gcccgctctt cactgatggt atcctcagct cagttc                               36

<210> SEQ ID NO 123
<211> LENGTH: 37
<212> TYPE: DNA
<213> ORGANISM: Artificial
<220> FEATURE:
<223> OTHER INFORMATION: An artificially synthesized primer sequence;
      MBL144-1 L antisense primer

<400> SEQUENCE: 123
atggtgcagc cacagttttg atttccagct tggtgcc                              37

<210> SEQ ID NO 124
<211> LENGTH: 36
<212> TYPE: DNA
<213> ORGANISM: Artificial
<220> FEATURE:
<223> OTHER INFORMATION: An artificially synthesized primer sequence;
      MBL184-6 H sense primer

<400> SEQUENCE: 124
gcccgctctt cgcctatgaa atgcagctgg ggcatc                               36

<210> SEQ ID NO 125
<211> LENGTH: 37
<212> TYPE: DNA
<213> ORGANISM: Artificial
<220> FEATURE:
<223> OTHER INFORMATION: An artificially synthesized primer sequence;
      MBL184-6 H antisense primer

<400> SEQUENCE: 125
ggcccttggt ggaggctgag gagactgtga gagtggt                                   37

<210> SEQ ID NO 126
<211> LENGTH: 36
<212> TYPE: DNA
<213> ORGANISM: Artificial
<220> FEATURE:
<223> OTHER INFORMATION: An artificially synthesized primer sequence;
      MBL184-6 L sense primer

<400> SEQUENCE: 126
gcccgctctt cactgatgaa gtttcctttt caactt                                    36

<210> SEQ ID NO 127
<211> LENGTH: 37
<212> TYPE: DNA
<213> ORGANISM: Artificial
<220> FEATURE:
<223> OTHER INFORMATION: An artificially synthesized primer sequence;
      MBL184-6 L antisense primer

<400> SEQUENCE: 127
atggtgcagc cacagttttg atttccagtt tggtgcc                                   37

<210> SEQ ID NO 128
<211> LENGTH: 36
<212> TYPE: DNA
<213> ORGANISM: Artificial
<220> FEATURE:
<223> OTHER INFORMATION: An artificially synthesized primer sequence;
      MBL259-3 H sense primer

<400> SEQUENCE: 128
gcccgctctt cgcctatgaa atgcagctgg ggcatg                                    36

<210> SEQ ID NO 129
<211> LENGTH: 37
<212> TYPE: DNA
<213> ORGANISM: Artificial
<220> FEATURE:
<223> OTHER INFORMATION: An artificially synthesized primer sequence;
      MBL259-3 H antisense primer

<400> SEQUENCE: 129
ggcccttggt ggaggctgca gagacagtga ccagagt                                   37

<210> SEQ ID NO 130
<211> LENGTH: 36
<212> TYPE: DNA
<213> ORGANISM: Artificial
<220> FEATURE:
<223> OTHER INFORMATION: An artificially synthesized primer sequence;
      MBL259-3 L sense primer

<400> SEQUENCE: 130
gcccgctctt cactgatgag tgtgctcact caggtc                                    36

<210> SEQ ID NO 131
<211> LENGTH: 37
<212> TYPE: DNA
<213> ORGANISM: Artificial
<220> FEATURE:
<223> OTHER INFORMATION: An artificially synthesized primer sequence;
      MBL259-3 L antisense primer

<400> SEQUENCE: 131
atggtgcagc cacagttttt atttccagtt tggtccc                           37

<210> SEQ ID NO 132
<211> LENGTH: 36
<212> TYPE: DNA
<213> ORGANISM: Artificial
<220> FEATURE:
<223> OTHER INFORMATION: An artificially synthesized primer sequence;
      MBL292-1 H sense primer

<400> SEQUENCE: 132
gcccgctctt cgcctatgaa atgcagctgg ggcatc                            36

<210> SEQ ID NO 133
<211> LENGTH: 37
<212> TYPE: DNA
<213> ORGANISM: Artificial
<220> FEATURE:
<223> OTHER INFORMATION: An artificially synthesized primer sequence;
      MBL292-1 antisense primer

<400> SEQUENCE: 133
ggcccttggt ggaggctgag gagactgtga gagtggt                           37

<210> SEQ ID NO 134
<211> LENGTH: 36
<212> TYPE: DNA
<213> ORGANISM: Artificial
<220> FEATURE:
<223> OTHER INFORMATION: An artificially synthesized primer sequence;
      MBL292-1 L sense primer

<400> SEQUENCE: 134
gcccgctctt cactgatgaa gtttcctttt caactt                            36

<210> SEQ ID NO 135
<211> LENGTH: 37
<212> TYPE: DNA
<213> ORGANISM: Artificial
<220> FEATURE:
<223> OTHER INFORMATION: An artificially synthesized primer sequence;
      MBL292-1 L antisense

<400> SEQUENCE: 135
atggtgcagc cacagttttg atttccagct tggtgcc                           37

<210> SEQ ID NO 136
<211> LENGTH: 36
<212> TYPE: DNA
<213> ORGANISM: Artificial
<220> FEATURE:
<223> OTHER INFORMATION: An artificially synthesized primer sequence;
      MBL352-34 H sense primer

<400> SEQUENCE: 136
gcccgctctt cgcctatgaa atgcagctgg ggcatg                            36

<210> SEQ ID NO 137

```
<211> LENGTH: 37
<212> TYPE: DNA
<213> ORGANISM: Artificial
<220> FEATURE:
<223> OTHER INFORMATION: An artificially synthesized primer sequence;
      MBL352-34 H antisense primer

<400> SEQUENCE: 137
ggcccttggt ggaggctgag gagactgtga gagtggt                                37

<210> SEQ ID NO 138
<211> LENGTH: 36
<212> TYPE: DNA
<213> ORGANISM: Artificial
<220> FEATURE:
<223> OTHER INFORMATION: An artificially synthesized primer sequence;
      MBL352-34 L sense primer

<400> SEQUENCE: 138
gcccgctctt cactgatgaa gtttcctttt caactt                                 36

<210> SEQ ID NO 139
<211> LENGTH: 37
<212> TYPE: DNA
<213> ORGANISM: Artificial
<220> FEATURE:
<223> OTHER INFORMATION: An artificially synthesized primer sequence;
      MBL352-34 L antisense primer

<400> SEQUENCE: 139
atggtgcagc cacagttttg atttccagct tggtgcc                                37

<210> SEQ ID NO 140
<211> LENGTH: 20
<212> TYPE: DNA
<213> ORGANISM: Artificial
<220> FEATURE:
<223> OTHER INFORMATION: An artificially synthesized primer sequence;
      5'-RACE H antisense primer

<400> SEQUENCE: 140 gatggggtg tcgttttggc                                                    20

<210> SEQ ID NO 141
<211> LENGTH: 20
<212> TYPE: DNA
<213> ORGANISM: Artificial
<220> FEATURE:
<223> OTHER INFORMATION: An artificially synthesized primer sequence;
      5'-RACE L antisense primer

<400> SEQUENCE: 141
gttggtgcag catcagcccg                                                   20

<210> SEQ ID NO 142
<211> LENGTH: 321
<212> TYPE: DNA
<213> ORGANISM: Mus musculus
<220> FEATURE:
<221> NAME/KEY: CDS
<222> LOCATION: (1)..(321)
<223> OTHER INFORMATION: MBL009-15 VL cDNA

<400> SEQUENCE: 142 gat atc cag atg aca cag act aca tcc tcc ctg tct gcc tct ctg gga        48
Asp Ile Gln Met Thr Gln Thr Thr Ser Ser Leu Ser Ala Ser Leu Gly
 1               5                  10                  15
```

```
gac aga ctc acc atc agt tgc agg gca agt cag gac att cgc aat tat      96
Asp Arg Leu Thr Ile Ser Cys Arg Ala Ser Gln Asp Ile Arg Asn Tyr
            20                  25                  30 tta aac tgg tat cag cag aaa cca gat gga act gtt aaa ctc ctg atc     144
Leu Asn Trp Tyr Gln Gln Lys Pro Asp Gly Thr Val Lys Leu Leu Ile
        35                  40                  45 tac tac aca tca aga tta cac tca gga gtc cca tca agg ttc agt ggc     192
Tyr Tyr Thr Ser Arg Leu His Ser Gly Val Pro Ser Arg Phe Ser Gly
    50                  55                  60 agt ggg tct gga aca gat tat tct ctc acc att agc aac ctg gag caa     240
Ser Gly Ser Gly Thr Asp Tyr Ser Leu Thr Ile Ser Asn Leu Glu Gln
65                  70                  75                  80 gaa gat att gcc act tac ttt tgc caa cag ggt aat acg ctt ccg tgg     288
Glu Asp Ile Ala Thr Tyr Phe Cys Gln Gln Gly Asn Thr Leu Pro Trp
                85                  90                  95 acg ttc ggt gga ggc acc aag ctg gaa atc aaa                         321
Thr Phe Gly Gly Gly Thr Lys Leu Glu Ile Lys
            100                 105
```

<210> SEQ ID NO 143
<211> LENGTH: 107
<212> TYPE: PRT
<213> ORGANISM: Mus musculus

<400> SEQUENCE: 143

```
Asp Ile Gln Met Thr Gln Thr Thr Ser Ser Leu Ser Ala Ser Leu Gly
1               5                   10                  15

Asp Arg Leu Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 144
<211> LENGTH: 348
<212> TYPE: DNA
<213> ORGANISM: Mus musculus
<220> FEATURE:
<221> NAME/KEY: CDS
<222> LOCATION: (1)..(348)
<223> OTHER INFORMATION: MBL009-15 VH cDNA

<400> SEQUENCE: 144

```
gtg cag ctt cag gag tcg gga cct ggc ctg gtg aaa cct tct cag tct      48
Val Gln Leu Gln Glu Ser Gly Pro Gly Leu Val Lys Pro Ser Gln Ser
1               5                   10                  15 ctg tcc ctc acc tgc act gtc act ggc tac tca atc acc agt gat tat      96
Leu Ser Leu Thr Cys Thr Val Thr Gly Tyr Ser Ile Thr Ser Asp Tyr
            20                  25                  30 gcc tgg aac tgg atc cgg cag ttt cca gga aac aaa ctg gag tgg atg     144
Ala Trp Asn Trp Ile Arg Gln Phe Pro Gly Asn Lys Leu Glu Trp Met
        35                  40                  45 ggc tac ata agc tac agt ggt agc act agc tac aac cca tct ctc aaa     192
Gly Tyr Ile Ser Tyr Ser Gly Ser Thr Ser Tyr Asn Pro Ser Leu Lys
```

```
                     50                  55                  60
agt cga atc tct atc act cga gac aca tcc aag aac cag ttc ttc ctg      240
Ser Arg Ile Ser Ile Thr Arg Asp Thr Ser Lys Asn Gln Phe Phe Leu
 65                  70                  75                  80 cag ttg aat tct gtg act act gag gac aca gcc aca tat tat tgt gca      288
Gln Leu Asn Ser Val Thr Thr Glu Asp Thr Ala Thr Tyr Tyr Cys Ala
                 85                  90                  95 aga ggg ggg att acg agg ttt gct tac tgg ggc caa ggg act ctg gtc      336
Arg Gly Gly Ile Thr Arg Phe Ala Tyr Trp Gly Gln Gly Thr Leu Val
            100                 105                 110 act gtc tct gca                                                      348
Thr Val Ser Ala
        115

<210> SEQ ID NO 145
<211> LENGTH: 116
<212> TYPE: PRT
<213> ORGANISM: Mus musculus

<400> SEQUENCE: 145

Val Gln Leu Gln Glu Ser Gly Pro Gly Leu Val Lys Pro Ser Gln Ser
 1               5                  10                  15

Leu Ser Leu Thr Cys Thr Val Thr Gly Tyr Ser Ile Thr Ser Asp Tyr
                20                  25                  30

Ala Trp Asn Trp Ile Arg Gln Phe Pro Gly Asn Lys Leu Glu Trp Met
            35                  40                  45

Gly Tyr Ile Ser Tyr Ser Gly Ser Thr Ser Tyr Asn Pro Ser Leu Lys
        50                  55                  60

Ser Arg Ile Ser Ile Thr Arg Asp Thr Ser Lys Asn Gln Phe Phe Leu
 65                 70                  75                  80

Gln Leu Asn Ser Val Thr Thr Glu Asp Thr Ala Thr Tyr Tyr Cys Ala
                85                  90                  95

Arg Gly Gly Ile Thr Arg Phe Ala Tyr Trp Gly Gln Gly Thr Leu Val
            100                 105                 110

Thr Val Ser Ala
        115

<210> SEQ ID NO 146
<211> LENGTH: 321
<212> TYPE: DNA
<213> ORGANISM: Mus musculus
<220> FEATURE:
<221> NAME/KEY: CDS
<222> LOCATION: (1)..(321)
<223> OTHER INFORMATION: MBL016-8 VL cDNA

<400> SEQUENCE: 146 gac atc cag atg aca cag tct cca tcc tca ctg tct gca tct ctg gga      48
Asp Ile Gln Met Thr Gln Ser Pro Ser Ser Leu Ser Ala Ser Leu Gly
 1               5                  10                  15 ggc aaa gtc acc atc act tgc aag gca agc caa gac att aac aag tat      96
Gly Lys Val Thr Ile Thr Cys Lys Ala Ser Gln Asp Ile Asn Lys Tyr
                20                  25                  30 ata gct tgg tac caa cac aag cct gga aaa ggt cct agg ctg ttt ata      144
Ile Ala Trp Tyr Gln His Lys Pro Gly Lys Gly Pro Arg Leu Phe Ile
            35                  40                  45 cat tac aca tct aaa cta cag cca ggc atc cca tca agg ttc agt gga      192
His Tyr Thr Ser Lys Leu Gln Pro Gly Ile Pro Ser Arg Phe Ser Gly
        50                  55                  60 agt ggg tct ggg aga gat tat tcc ttc agc atc agc aac ctg gag cct      240
```

```
Ser Gly Ser Gly Arg Asp Tyr Ser Phe Ser Ile Ser Asn Leu Glu Pro
65                  70                  75                  80 gaa gat att gca act tat tat tgt cta cag tat gat aat ctt ctg tat         288
Glu Asp Ile Ala Thr Tyr Tyr Cys Leu Gln Tyr Asp Asn Leu Leu Tyr
                85                  90                  95 acg ttc gga ggg ggg acc aag ctg gaa ata aaa                             321
Thr Phe Gly Gly Gly Thr Lys Leu Glu Ile Lys
                100                 105
```

<210> SEQ ID NO 147
<211> LENGTH: 107
<212> TYPE: PRT
<213> ORGANISM: Mus musculus

<400> SEQUENCE: 147

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Ala Trp Tyr Gln His Lys Pro Gly Lys Gly Pro Arg Leu Phe Ile
            35                  40                  45

His Tyr Thr Ser Lys Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys
                100                 105
```

<210> SEQ ID NO 148
<211> LENGTH: 336
<212> TYPE: DNA
<213> ORGANISM: Mus musculus
<220> FEATURE:
<221> NAME/KEY: CDS
<222> LOCATION: (1)..(336)
<223> OTHER INFORMATION: MBL016-8 VH cDNA

<400> SEQUENCE: 148

```
gtt cag ctg cag cag tct ggg gct gag ctt gtg agg cca ggg gcc tca         48
Val Gln Leu Gln Gln Ser Gly Ala Glu Leu Val Arg Pro Gly Ala Ser
1               5                   10                  15 gtc aag ttg tcc tgc aca gct tct ggc ttt aac att aaa gac gac tat         96
Val Lys Leu Ser Cys Thr Ala Ser Gly Phe Asn Ile Lys Asp Asp Tyr
                20                  25                  30 atg tac tgg gtg aag cag agg cct gaa cag ggc ctg gag tgg att gga        144
Met Tyr Trp Val Lys Gln Arg Pro Glu Gln Gly Leu Glu Trp Ile Gly
            35                  40                  45 agg att gat cct gcg aat ggt aat act aaa tat gcc ccg aag ttc cag        192
Arg Ile Asp Pro Ala Asn Gly Asn Thr Lys Tyr Ala Pro Lys Phe Gln
    50                  55                  60 gac aag gcc act ata act gca gac aca tcc tcc aac aca gcc tac ctg        240
Asp Lys Ala Thr Ile Thr Ala Asp Thr Ser Ser Asn Thr Ala Tyr Leu
65                  70                  75                  80 cat ctc agc agc ctg aca tct gag gac act gcc gtc ttt tac tgt gct        288
His Leu Ser Ser Leu Thr Ser Glu Asp Thr Ala Val Phe Tyr Cys Ala
                85                  90                  95 tat aga cgg gct tac tgg ggc caa ggg act ctg gtc act gtc tct gca        336
Tyr Arg Arg Ala Tyr Trp Gly Gln Gly Thr Leu Val Thr Val Ser Ala
                100                 105                 110
```

<210> SEQ ID NO 149
<211> LENGTH: 112
<212> TYPE: PRT
<213> ORGANISM: Mus musculus

<400> SEQUENCE: 149

Val Gln Leu Gln Gln Ser Gly Ala Glu Leu Val Arg Pro Gly Ala Ser
1               5                   10                  15

Val Lys Leu Ser Cys Thr Ala Ser Gly Phe Asn Ile Lys Asp Asp Tyr
            20                  25                  30

Met Tyr Trp Val Lys Gln Arg Pro Glu Gln Gly Leu Glu Trp Ile Gly
        35                  40                  45

Arg Ile Asp Pro Ala Asn Gly Asn Thr Lys Tyr Ala Pro Lys Phe Gln
    50                  55                  60

Asp Lys Ala Thr Ile Thr Ala Asp Thr Ser Ser Asn Thr Ala Tyr Leu
65                  70                  75                  80

His Leu Ser Ser Leu Thr Ser Glu Asp Thr Ala Val Phe Tyr Cys Ala
                85                  90                  95

Tyr Arg Arg Ala Tyr Trp Gly Gln Gly Thr Leu Val Thr Val Ser Ala
            100                 105                 110

<210> SEQ ID NO 150
<211> LENGTH: 318
<212> TYPE: DNA
<213> ORGANISM: Mus musculus
<220> FEATURE:
<221> NAME/KEY: CDS
<222> LOCATION: (1)..(318)
<223> OTHER INFORMATION: MBL018-1 VL cDNA

<400> SEQUENCE: 150 att gtg atg acc cag act ccc aaa ctc ctg cct gta tca gca gga gac     48
Ile Val Met Thr Gln Thr Pro Lys Leu Leu Pro Val Ser Ala Gly Asp
1               5                   10                  15 agg gtt acc atg acc tgc aag gcc agt cag agt gtg gat aat agt gta    96
Arg Val Thr Met Thr Cys Lys Ala Ser Gln Ser Val Asp Asn Ser Val
            20                  25                  30 gcc tgg tac caa cag aag cca gga cag tct cct aaa ttg ctg ata ttc   144
Ala Trp Tyr Gln Gln Lys Pro Gly Gln Ser Pro Lys Leu Leu Ile Phe
        35                  40                  45 tat gca tcc aat cac tac act gga gtc cct gat cgc ttc act gcc agt   192
Tyr Ala Ser Asn His Tyr Thr Gly Val Pro Asp Arg Phe Thr Ala Ser
    50                  55                  60 gga tct ggg aca gat ttc act ttc acc atc agc agt gtg cag gtt gaa   240
Gly Ser Gly Thr Asp Phe Thr Phe Thr Ile Ser Ser Val Gln Val Glu
65                  70                  75                  80 gac ctg gca gtt tat ttc tgt cag cag cat ttt agc tct cct cgg acg   288
Asp Leu Ala Val Tyr Phe Cys Gln Gln His Phe Ser Ser Pro Arg Thr
                85                  90                  95 ttc ggt gga ggc acc aaa ctg gaa atc aga                           318
Phe Gly Gly Gly Thr Lys Leu Glu Ile Arg
            100                 105

<210> SEQ ID NO 151
<211> LENGTH: 106
<212> TYPE: PRT
<213> ORGANISM: Mus musculus

<400> SEQUENCE: 151

Ile Val Met Thr Gln Thr Pro Lys Leu Leu Pro Val Ser Ala Gly Asp

```
                1               5                   10                  15
            Arg Val Thr Met Thr Cys Lys Ala Ser Gln Ser Val Asp Asn Ser Val
                            20                  25                  30

Ala Trp Tyr Gln Gln Lys Pro Gly Gln Ser Pro Lys Leu Leu Ile Phe
                            35                  40                  45

Tyr Ala Ser Asn His Tyr Thr Gly Val Pro Asp Arg Phe Thr Ala Ser
                            50                  55                  60

Gly Ser Gly Thr Asp Phe Thr Phe Thr Ile Ser Ser Val Gln Val Glu
            65                  70                  75                  80

Asp Leu Ala Val Tyr Phe Cys Gln Gln His Phe Ser Ser Pro Arg Thr
                            85                  90                  95

Phe Gly Gly Gly Thr Lys Leu Glu Ile Arg
                            100                 105
```

```
<210> SEQ ID NO 152
<211> LENGTH: 345
<212> TYPE: DNA
<213> ORGANISM: Mus musculus
<220> FEATURE:
<221> NAME/KEY: CDS
<222> LOCATION: (1)..(345)
<223> OTHER INFORMATION: MBL018-1 VH cDNA

<400> SEQUENCE: 152
```

```
gag gtt cag ctc cag cag tct ggg act gtg ctg aca agg cct ggg gct    48
Glu Val Gln Leu Gln Gln Ser Gly Thr Val Leu Thr Arg Pro Gly Ala
1               5                   10                  15 tca gtg aag atg tcc tgc aag gct tct ggc tac acc ttt acc aac ttc    96
Ser Val Lys Met Ser Cys Lys Ala Ser Gly Tyr Thr Phe Thr Asn Phe
                20                  25                  30 tgg atc cac tgg gtc aaa cag agg cct gga cag ggt ctg gac tgg att   144
Trp Ile His Trp Val Lys Gln Arg Pro Gly Gln Gly Leu Asp Trp Ile
            35                  40                  45 ggc gct att tat cct gga aat act aat act gac tac aac cag aag ttc   192
Gly Ala Ile Tyr Pro Gly Asn Thr Asn Thr Asp Tyr Asn Gln Lys Phe
        50                  55                  60 cag ggc aag gcc aaa ctg act gct gtc tca tct gcc agc act gcc tac   240
Gln Gly Lys Ala Lys Leu Thr Ala Val Ser Ser Ala Ser Thr Ala Tyr
65                  70                  75                  80 atg gag ctc agc agc ctg aca aat gag gac tct gcg gtc tat tac tgt   288
Met Glu Leu Ser Ser Leu Thr Asn Glu Asp Ser Ala Val Tyr Tyr Cys
                85                  90                  95 aca agg ggg ggg gct atg gac tac tgg ggt caa gga acc tca gtc acc   336
Thr Arg Gly Gly Ala Met Asp Tyr Trp Gly Gln Gly Thr Ser Val Thr
            100                 105                 110 gtc tcc tca                                                        345
Val Ser Ser
        115
```

```
<210> SEQ ID NO 153
<211> LENGTH: 115
<212> TYPE: PRT
<213> ORGANISM: Mus musculus

<400> SEQUENCE: 153

Glu Val Gln Leu Gln Gln Ser Gly Thr Val Leu Thr Arg Pro Gly Ala
1               5                   10                  15

Ser Val Lys Met Ser Cys Lys Ala Ser Gly Tyr Thr Phe Thr Asn Phe
                20                  25                  30

Trp Ile His Trp Val Lys Gln Arg Pro Gly Gln Gly Leu Asp Trp Ile
```

```
                35                  40                  45
Gly Ala Ile Tyr Pro Gly Asn Thr Asn Thr Asp Tyr Asn Gln Lys Phe
 50                  55                  60

Gln Gly Lys Ala Lys Leu Thr Ala Val Ser Ser Ala Ser Thr Ala Tyr
 65                  70                  75                  80

Met Glu Leu Ser Ser Leu Thr Asn Glu Asp Ser Ala Val Tyr Tyr Cys
                 85                  90                  95

Thr Arg Gly Gly Ala Met Asp Tyr Trp Gly Gln Gly Thr Ser Val Thr
             100                 105                 110

Val Ser Ser
        115

<210> SEQ ID NO 154
<211> LENGTH: 321
<212> TYPE: DNA
<213> ORGANISM: Mus musculus
<220> FEATURE:
<221> NAME/KEY: CDS
<222> LOCATION: (1)..(321)
<223> OTHER INFORMATION: MBL144-1 VL cDNA

<400> SEQUENCE: 154 gac atc ctg atg acc cag tct cca gcc acc ctg tct gtg act cca gga      48
Asp Ile Leu Met Thr Gln Ser Pro Ala Thr Leu Ser Val Thr Pro Gly
 1               5                  10                  15 gaa aca gtc agt ctt tcc tgt agg gcc agc cag aat act tac aag aac      96
Glu Thr Val Ser Leu Ser Cys Arg Ala Ser Gln Asn Thr Tyr Lys Asn
             20                  25                  30 cta cac tgg tat caa cag aaa tca cat ggg act cca aag ctt ctc atc     144
Leu His Trp Tyr Gln Gln Lys Ser His Gly Thr Pro Lys Leu Leu Ile
         35                  40                  45 aag tat gca tct gct ccc atc tct ggg atc ccc tcc agg ttc act ggc     192
Lys Tyr Ala Ser Ala Pro Ile Ser Gly Ile Pro Ser Arg Phe Thr Gly
     50                  55                  60 agt gga tca ggg aca gat tac act ctc agt atc aac agt gtg aag ccc     240
Ser Gly Ser Gly Thr Asp Tyr Thr Leu Ser Ile Asn Ser Val Lys Pro
 65                  70                  75                  80 gaa gat gaa gga ata tat tac tgt ctt cag ggt tac agc atg ccg tgg     288
Glu Asp Glu Gly Ile Tyr Tyr Cys Leu Gln Gly Tyr Ser Met Pro Trp
                 85                  90                  95 acg ttc ggt gga ggc acc aag ctg gaa atc aaa                         321
Thr Phe Gly Gly Gly Thr Lys Leu Glu Ile Lys
            100                 105

<210> SEQ ID NO 155
<211> LENGTH: 107
<212> TYPE: PRT
<213> ORGANISM: Mus musculus

<400> SEQUENCE: 155

Asp Ile Leu Met Thr Gln Ser Pro Ala Thr Leu Ser Val Thr Pro Gly
 1               5                  10                  15

Glu Thr Val Ser Leu Ser Cys Arg Ala Ser Gln Asn Thr Tyr Lys Asn
             20                  25                  30

Leu His Trp Tyr Gln Gln Lys Ser His Gly Thr Pro Lys Leu Leu Ile
         35                  40                  45

Lys Tyr Ala Ser Ala Pro Ile Ser Gly Ile Pro Ser Arg Phe Thr Gly
     50                  55                  60

Ser Gly Ser Gly Thr Asp Tyr Thr Leu Ser Ile Asn Ser Val Lys Pro
 65                  70                  75                  80
```

```
Glu Asp Glu Gly Ile Tyr Tyr Cys Leu Gln Gly Tyr Ser Met Pro Trp
            85                  90                  95

Thr Phe Gly Gly Gly Thr Lys Leu Glu Ile Lys
            100                 105
```

<210> SEQ ID NO 156
<211> LENGTH: 348
<212> TYPE: DNA
<213> ORGANISM: Mus musculus
<220> FEATURE:
<221> NAME/KEY: CDS
<222> LOCATION: (1)..(348)
<223> OTHER INFORMATION: MBL144-1 VH cDNA

<400> SEQUENCE: 156

```
gtg cag ctt cag gag tca gga cct ggc ctg gca aaa cct tct cag act      48
Val Gln Leu Gln Glu Ser Gly Pro Gly Leu Ala Lys Pro Ser Gln Thr
1               5                   10                  15 ctg tcc ctc acc tgt tct gtc act ggc tac tcc atc acc agt gat tac      96
Leu Ser Leu Thr Cys Ser Val Thr Gly Tyr Ser Ile Thr Ser Asp Tyr
            20                  25                  30 tgg aac tgg atc cgg aaa ttc cca ggg aat aaa ctt gag tac atg ggg     144
Trp Asn Trp Ile Arg Lys Phe Pro Gly Asn Lys Leu Glu Tyr Met Gly
        35                  40                  45 tac ata agc tac agt ggt agc act tac tac aat cca tct ctc aaa agt     192
Tyr Ile Ser Tyr Ser Gly Ser Thr Tyr Tyr Asn Pro Ser Leu Lys Ser
    50                  55                  60 cga atc tcc atc act cga gac aca tcc aag aac cag tat tac ctg cag     240
Arg Ile Ser Ile Thr Arg Asp Thr Ser Lys Asn Gln Tyr Tyr Leu Gln
65                  70                  75                  80 ttg aat tct gtg act act gag gac aca gcc aca tat tac tgt gca aga     288
Leu Asn Ser Val Thr Thr Glu Asp Thr Ala Thr Tyr Tyr Cys Ala Arg
                85                  90                  95 tcc tac gat ggt atc tgc ttt gac aac tgg ggc caa ggc acc act ctc     336
Ser Tyr Asp Gly Ile Cys Phe Asp Asn Trp Gly Gln Gly Thr Thr Leu
            100                 105                 110 aca gtc tcc tca                                                     348
Thr Val Ser Ser
        115
```

<210> SEQ ID NO 157
<211> LENGTH: 116
<212> TYPE: PRT
<213> ORGANISM: Mus musculus

<400> SEQUENCE: 157

```
Val Gln Leu Gln Glu Ser Gly Pro Gly Leu Ala Lys Pro Ser Gln Thr
1               5                   10                  15

Leu Ser Leu Thr Cys Ser Val Thr Gly Tyr Ser Ile Thr Ser Asp Tyr
            20                  25                  30

Trp Asn Trp Ile Arg Lys Phe Pro Gly Asn Lys Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu Gln
65                  70                  75                  80

Leu Asn Ser Val Thr Thr Glu Asp Thr Ala Thr Tyr Tyr Cys Ala Arg
                85                  90                  95

Ser Tyr Asp Gly Ile Cys Phe Asp Asn Trp Gly Gln Gly Thr Thr Leu
            100                 105                 110
```

-continued

```
Thr Val Ser Ser
        115

<210> SEQ ID NO 158
<211> LENGTH: 318
<212> TYPE: DNA
<213> ORGANISM: Mus musculus
<220> FEATURE:
<221> NAME/KEY: CDS
<222> LOCATION: (1)..(318)
<223> OTHER INFORMATION: MBL184-6 VL cDNA

<400> SEQUENCE: 158 atc cag atg aca caa tct tca tcc tcc ttg tct gta tct cta gga gac      48
Ile Gln Met Thr Gln Ser Ser Ser Ser Leu Ser Val Ser Leu Gly Asp
1               5                   10                  15 aga gtc acc att act tgc aag gca agt gaa cac att aat agt tgg tta      96
Arg Val Thr Ile Thr Cys Lys Ala Ser Glu His Ile Asn Ser Trp Leu
            20                  25                  30 gcc tgg tat cag caa aaa cca gga aat gct cct agg ctc tta ata tct     144
Ala Trp Tyr Gln Gln Lys Pro Gly Asn Ala Pro Arg Leu Leu Ile Ser
        35                  40                  45 ggt gca acc aat ttg aaa act ggg gtt cct tca aga ttc agt ggc agt     192
Gly Ala Thr Asn Leu Lys Thr Gly Val Pro Ser Arg Phe Ser Gly Ser
    50                  55                  60 gca tct gga aag gat tac act ctc aac att act agt ctt cag act gaa     240
Ala Ser Gly Lys Asp Tyr Thr Leu Asn Ile Thr Ser Leu Gln Thr Glu
65                  70                  75                  80 gat gtt gct act tat tac tgt caa cag tat tgg ggt act ccg tgg acg     288
Asp Val Ala Thr Tyr Tyr Cys Gln Gln Tyr Trp Gly Thr Pro Trp Thr
                85                  90                  95 ttc ggt gga ggc acc aaa ctg gaa atc aaa                             318
Phe Gly Gly Gly Thr Lys Leu Glu Ile Lys
            100                 105

<210> SEQ ID NO 159
<211> LENGTH: 106
<212> TYPE: PRT
<213> ORGANISM: Mus musculus

<400> SEQUENCE: 159

Ile Gln Met Thr Gln Ser Ser Ser Ser Leu Ser Val Ser Leu Gly Asp
1               5                   10                  15

Arg Val Thr Ile Thr Cys Lys Ala Ser Glu His Ile Asn Ser Trp Leu
            20                  25                  30

Ala Trp Tyr Gln Gln Lys Pro Gly Asn Ala Pro Arg Leu Leu Ile Ser
        35                  40                  45

Gly Ala Thr Asn Leu Lys Thr Gly Val Pro Ser Arg Phe Ser Gly Ser
    50                  55                  60

Ala Ser Gly Lys Asp Tyr Thr Leu Asn Ile Thr Ser Leu Gln Thr Glu
65                  70                  75                  80

Asp Val Ala Thr Tyr Tyr Cys Gln Gln Tyr Trp Gly Thr Pro Trp Thr
                85                  90                  95

Phe Gly Gly Gly Thr Lys Leu Glu Ile Lys
            100                 105

<210> SEQ ID NO 160
<211> LENGTH: 348
<212> TYPE: DNA
<213> ORGANISM: Mus musculus
<220> FEATURE:
```

```
<221> NAME/KEY: CDS
<222> LOCATION: (1)..(348)
<223> OTHER INFORMATION: MBL184-6 VH cDNA

<400> SEQUENCE: 160 gag gtt cag ctg cag cag tct ggg gct gaa ctt gtg agg cca ggg gcc      48
Glu Val Gln Leu Gln Gln Ser Gly Ala Glu Leu Val Arg Pro Gly Ala
1               5                   10                  15 tca gtc aag ttg tcc tgc aca gtt tct ggc ttt aac att aaa gac gac      96
Ser Val Lys Leu Ser Cys Thr Val Ser Gly Phe Asn Ile Lys Asp Asp
                20                  25                  30 tat atg cac tgg gtg aag cag agg cct gaa cag ggc ctg gag tgg att     144
Tyr Met His Trp Val Lys Gln Arg Pro Glu Gln Gly Leu Glu Trp Ile
            35                  40                  45 gga agg att gat cct gcg aat ggt cat act aaa tat gcc ccg aag ttc     192
Gly Arg Ile Asp Pro Ala Asn Gly His Thr Lys Tyr Ala Pro Lys Phe
        50                  55                  60 cag gac aag gcc act ata act gca gac aca tcc tcc aac aca gcc tac     240
Gln Asp Lys Ala Thr Ile Thr Ala Asp Thr Ser Ser Asn Thr Ala Tyr
65                  70                  75                  80 ctg cag ttc agc agc ctg aca tct gag gac act gcc gtc tat tac tgt     288
Leu Gln Phe Ser Ser Leu Thr Ser Glu Asp Thr Ala Val Tyr Tyr Cys
                85                  90                  95 aca aga atg ggg tta cga cga ggc tac tgg ggc caa ggc acc act ctc     336
Thr Arg Met Gly Leu Arg Arg Gly Tyr Trp Gly Gln Gly Thr Thr Leu
            100                 105                 110 aca gtc tcc tca                                                      348
Thr Val Ser Ser
        115

<210> SEQ ID NO 161
<211> LENGTH: 116
<212> TYPE: PRT
<213> ORGANISM: Mus musculus

<400> SEQUENCE: 161

Glu Val Gln Leu Gln Gln Ser Gly Ala Glu Leu Val Arg Pro Gly Ala
1               5                   10                  15

Ser Val Lys Leu Ser Cys Thr Val Ser Gly Phe Asn Ile Lys Asp Asp
                20                  25                  30

Tyr Met His Trp Val Lys Gln Arg Pro Glu Gln Gly Leu Glu Trp Ile
            35                  40                  45

Gly Arg Ile Asp Pro Ala Asn Gly His Thr Lys Tyr Ala Pro Lys Phe
        50                  55                  60

Gln Asp Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Thr Arg Met Gly Leu Arg Arg Gly Tyr Trp Gly Gln Gly Thr Thr Leu
            100                 105                 110

Thr Val Ser Ser
        115

<210> SEQ ID NO 162
<211> LENGTH: 336
<212> TYPE: DNA
<213> ORGANISM: Mus musculus
<220> FEATURE:
<221> NAME/KEY: CDS
<222> LOCATION: (1)..(336)
<223> OTHER INFORMATION: MBL259-3 VL cDNA
```

<400> SEQUENCE: 162

| | | | | | | | | | | | | | | | | |
|---|---|---|---|---|---|---|---|---|---|---|---|---|---|---|---|---|
| gat | att | gtg | atg | act | cag | gct | gca | ccc | tct | gta | cct | gtc | act | cct | gga | 48 |
| Asp | Ile | Val | Met | Thr | Gln | Ala | Ala | Pro | Ser | Val | Pro | Val | Thr | Pro | Gly | |
| 1 | | | | 5 | | | | | 10 | | | | | 15 | | |

| gag | tca | gta | tcc | atc | tcc | tgc | agg | tct | agt | aag | agt | ctc | ctg | cat | aga | 96 |
|---|---|---|---|---|---|---|---|---|---|---|---|---|---|---|---|---|
| Glu | Ser | Val | Ser | Ile | Ser | Cys | Arg | Ser | Ser | Lys | Ser | Leu | Leu | His | Arg | |
| | | | 20 | | | | | 25 | | | | | 30 | | | |

| aat | ggc | aac | act | tat | ttg | tat | tgg | ttc | ctg | cag | agg | cca | ggc | cag | tct | 144 |
|---|---|---|---|---|---|---|---|---|---|---|---|---|---|---|---|---|
| Asn | Gly | Asn | Thr | Tyr | Leu | Tyr | Trp | Phe | Leu | Gln | Arg | Pro | Gly | Gln | Ser | |
| | | 35 | | | | | 40 | | | | | 45 | | | | |

| cct | cag | ctc | ctg | ata | tat | cgg | atg | tcc | aac | ctt | gcc | tca | gga | gtc | cca | 192 |
|---|---|---|---|---|---|---|---|---|---|---|---|---|---|---|---|---|
| Pro | Gln | Leu | Leu | Ile | Tyr | Arg | Met | Ser | Asn | Leu | Ala | Ser | Gly | Val | Pro | |
| | 50 | | | | | 55 | | | | | 60 | | | | | |

| gac | agg | ttc | agt | ggc | agt | ggg | tca | gga | act | gct | ttc | aca | ctg | aga | atc | 240 |
|---|---|---|---|---|---|---|---|---|---|---|---|---|---|---|---|---|
| Asp | Arg | Phe | Ser | Gly | Ser | Gly | Ser | Gly | Thr | Ala | Phe | Thr | Leu | Arg | Ile | |
| 65 | | | | | 70 | | | | | 75 | | | | | 80 | |

| agt | aga | gtg | gag | gct | gag | gat | gtg | ggt | gtt | tat | tac | tgt | ttg | caa | cat | 288 |
|---|---|---|---|---|---|---|---|---|---|---|---|---|---|---|---|---|
| Ser | Arg | Val | Glu | Ala | Glu | Asp | Val | Gly | Val | Tyr | Tyr | Cys | Leu | Gln | His | |
| | | | | 85 | | | | | 90 | | | | | 95 | | |

| cta | gaa | tat | cct | tat | acg | ttc | gga | tcg | ggg | acc | aaa | ctg | gaa | ata | aaa | 336 |
|---|---|---|---|---|---|---|---|---|---|---|---|---|---|---|---|---|
| Leu | Glu | Tyr | Pro | Tyr | Thr | Phe | Gly | Ser | Gly | Thr | Lys | Leu | Glu | Ile | Lys | |
| | | | 100 | | | | | 105 | | | | | 110 | | | |

<210> SEQ ID NO 163
<211> LENGTH: 112
<212> TYPE: PRT
<213> ORGANISM: Mus musculus

<400> SEQUENCE: 163

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Arg
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Tyr Thr Phe Gly Ser Gly Thr Lys Leu Glu Ile Lys
            100                 105                 110

<210> SEQ ID NO 164
<211> LENGTH: 342
<212> TYPE: DNA
<213> ORGANISM: Mus musculus
<220> FEATURE:
<221> NAME/KEY: CDS
<222> LOCATION: (1)..(342)
<223> OTHER INFORMATION: MBL259-3 VH cDNA

<400> SEQUENCE: 164

| gtt | cag | ctg | cag | cag | tct | ggg | gct | gag | ctt | gtg | agg | cca | ggg | gcc | tca | 48 |
|---|---|---|---|---|---|---|---|---|---|---|---|---|---|---|---|---|
| Val | Gln | Leu | Gln | Gln | Ser | Gly | Ala | Glu | Leu | Val | Arg | Pro | Gly | Ala | Ser | |
| 1 | | | | 5 | | | | | 10 | | | | | 15 | | |

| gtc | aag | ttg | tcc | tgc | aca | gct | tct | gac | ttt | aac | att | aaa | gac | gac | tat | 96 |
|---|---|---|---|---|---|---|---|---|---|---|---|---|---|---|---|---|
| Val | Lys | Leu | Ser | Cys | Thr | Ala | Ser | Asp | Phe | Asn | Ile | Lys | Asp | Asp | Tyr | |
| | | | 20 | | | | | 25 | | | | | 30 | | | |

```
atg cac tgg atg aag cag agg cct gaa cag ggc ctg gag tgg att gga      144
Met His Trp Met Lys Gln Arg Pro Glu Gln Gly Leu Glu Trp Ile Gly
            35                  40                  45 agg att gat cct gcg aat ggt aat act aaa tat gcc ccg aag ttc cag      192
Arg Ile Asp Pro Ala Asn Gly Asn Thr Lys Tyr Ala Pro Lys Phe Gln
 50                  55                  60 gac aag gcc act atg act gca gac aca tcc tcc aac aca gcc tac ttg      240
Asp Lys Ala Thr Met Thr Ala Asp Thr Ser Ser Asn Thr Ala Tyr Leu
65                  70                  75                  80 caa ttc agc agc ctg aca tct gag gac act gcc gtc tat tac tgt gct      288
Gln Phe Ser Ser Leu Thr Ser Glu Asp Thr Ala Val Tyr Tyr Cys Ala
                85                  90                  95 act tct tgg ggc ttt cct tat tgg ggc caa ggg act ctg gtc act gtc      336
Thr Ser Trp Gly Phe Pro Tyr Trp Gly Gln Gly Thr Leu Val Thr Val
            100                 105                 110 tct gca                                                              342
Ser Ala
```

```
<210> SEQ ID NO 165
<211> LENGTH: 114
<212> TYPE: PRT
<213> ORGANISM: Mus musculus

<400> SEQUENCE: 165

Val Gln Leu Gln Gln Ser Gly Ala Glu Leu Val Arg Pro Gly Ala Ser
1               5                   10                  15

Val Lys Leu Ser Cys Thr Ala Ser Asp Phe Asn Ile Lys Asp Asp Tyr
            20                  25                  30

Met His Trp Met Lys Gln Arg Pro Glu Gln Gly Leu Glu Trp Ile Gly
        35                  40                  45

Arg Ile Asp Pro Ala Asn Gly Asn Thr Lys Tyr Ala Pro Lys Phe Gln
    50                  55                  60

Asp Lys Ala Thr Met Thr Ala Asp Thr Ser Ser Asn Thr Ala Tyr Leu
65                  70                  75                  80

Gln Phe Ser Ser Leu Thr Ser Glu Asp Thr Ala Val Tyr Tyr Cys Ala
                85                  90                  95

Thr Ser Trp Gly Phe Pro Tyr Trp Gly Gln Gly Thr Leu Val Thr Val
            100                 105                 110

Ser Ala
```

```
<210> SEQ ID NO 166
<211> LENGTH: 318
<212> TYPE: DNA
<213> ORGANISM: Mus musculus
<220> FEATURE:
<221> NAME/KEY: CDS
<222> LOCATION: (1)..(318)
<223> OTHER INFORMATION: MBL292-1 VL cDNA

<400> SEQUENCE: 166 atc cag atg aca caa tct tca tcc tcc ttg tct gta tct cta gga gac       48
Ile Gln Met Thr Gln Ser Ser Ser Ser Leu Ser Val Ser Leu Gly Asp
1               5                   10                  15 aga gtc acc att act tgc aag gca agt gta cac att aat agt tgg tta       96
Arg Val Thr Ile Thr Cys Lys Ala Ser Val His Ile Asn Ser Trp Leu
            20                  25                  30 gcc tgg tat cag caa aaa cca gga aat gct cct agg ctc tta ata tct      144
Ala Trp Tyr Gln Gln Lys Pro Gly Asn Ala Pro Arg Leu Leu Ile Ser
        35                  40                  45
```

```
ggt gca acc aat ttg aaa act ggg gtt cct tca aga ttc agt ggc agt       192
Gly Ala Thr Asn Leu Lys Thr Gly Val Pro Ser Arg Phe Ser Gly Ser
 50                  55                  60 gca tct gga aag gat tac act ctc agc att act agt ctt cag act gaa       240
Ala Ser Gly Lys Asp Tyr Thr Leu Ser Ile Thr Ser Leu Gln Thr Glu
 65                  70                  75                  80 gat gtt gct act tat tac tgt caa cag tat tgg gat act ccg tgg acg       288
Asp Val Ala Thr Tyr Tyr Cys Gln Gln Tyr Trp Asp Thr Pro Trp Thr
                 85                  90                  95 ttc ggt gga ggc acc aag ctg gaa atc aaa                               318
Phe Gly Gly Gly Thr Lys Leu Glu Ile Lys
                100                 105

<210> SEQ ID NO 167
<211> LENGTH: 106
<212> TYPE: PRT
<213> ORGANISM: Mus musculus

<400> SEQUENCE: 167

Ile Gln Met Thr Gln Ser Ser Ser Leu Ser Val Ser Leu Gly Asp
 1               5                  10                  15

Arg Val Thr Ile Thr Cys Lys Ala Ser Val His Ile Asn Ser Trp Leu
                 20                  25                  30

Ala Trp Tyr Gln Gln Lys Pro Gly Asn Ala Pro Arg Leu Leu Ile Ser
             35                  40                  45

Gly Ala Thr Asn Leu Lys Thr Gly Val Pro Ser Arg Phe Ser Gly Ser
 50                  55                  60

Ala Ser Gly Lys Asp Tyr Thr Leu Ser Ile Thr Ser Leu Gln Thr Glu
 65                  70                  75                  80

Asp Val Ala Thr Tyr Tyr Cys Gln Gln Tyr Trp Asp Thr Pro Trp Thr
                 85                  90                  95

Phe Gly Gly Gly Thr Lys Leu Glu Ile Lys
                100                 105

<210> SEQ ID NO 168
<211> LENGTH: 345
<212> TYPE: DNA
<213> ORGANISM: Mus musculus
<220> FEATURE:
<221> NAME/KEY: CDS
<222> LOCATION: (1)..(345)
<223> OTHER INFORMATION: MBL292-1 VH cDNA

<400> SEQUENCE: 168 gtt cag ctg cag cag tct ggg gct gag ctt gtg agg cca ggg gcc tca        48
Val Gln Leu Gln Gln Ser Gly Ala Glu Leu Val Arg Pro Gly Ala Ser
 1               5                  10                  15 gtc aag ttg tcc tgc aca gct tct ggc ttt aac att aaa gac gac tat        96
Val Lys Leu Ser Cys Thr Ala Ser Gly Phe Asn Ile Lys Asp Asp Tyr
                 20                  25                  30 atg cac tgg atg aag cag agg cct gaa cag ggc ctg gag tgg att gga       144
Met His Trp Met Lys Gln Arg Pro Glu Gln Gly Leu Glu Trp Ile Gly
             35                  40                  45 agg att gat cct gcg aat ggt aat act aaa tat gcc ccg aag ttc cag       192
Arg Ile Asp Pro Ala Asn Gly Asn Thr Lys Tyr Ala Pro Lys Phe Gln
 50                  55                  60 gac aag gcc act ata act gca gac aca tcc tcc aac aca gcc tac ctg       240
Asp Lys Ala Thr Ile Thr Ala Asp Thr Ser Ser Asn Thr Ala Tyr Leu
 65                  70                  75                  80 cag ctc agc agc ctg aca tct gag gac act gcc gtc tat tac tgt tct       288
Gln Leu Ser Ser Leu Thr Ser Glu Asp Thr Ala Val Tyr Tyr Cys Ser
```

```
aga atg ggg tta ctt cga ggc tac tgg ggc caa ggc acc act ctc aca    336
Arg Met Gly Leu Leu Arg Gly Tyr Trp Gly Gln Gly Thr Thr Leu Thr
        100                 105                 110 gtc tcc tca                                                         345
Val Ser Ser
        115
```

<210> SEQ ID NO 169
<211> LENGTH: 115
<212> TYPE: PRT
<213> ORGANISM: Mus musculus

<400> SEQUENCE: 169

```
Val Gln Leu Gln Gln Ser Gly Ala Glu Leu Val Arg Pro Gly Ala Ser
1               5                   10                  15

Val Lys Leu Ser Cys Thr Ala Ser Gly Phe Asn Ile Lys Asp Asp Tyr
            20                  25                  30

Met His Trp Met Lys Gln Arg Pro Glu Gln Gly Leu Glu Trp Ile Gly
        35                  40                  45

Arg Ile Asp Pro Ala Asn Gly Asn Thr Lys Tyr Ala Pro Lys Phe Gln
    50                  55                  60

Asp Lys Ala Thr Ile Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Ser
                85                  90                  95

Arg Met Gly Leu Leu Arg Gly Tyr Trp Gly Gln Gly Thr Thr Leu Thr
            100                 105                 110

Val Ser Ser
        115
```

<210> SEQ ID NO 170
<211> LENGTH: 318
<212> TYPE: DNA
<213> ORGANISM: Mus musculus
<220> FEATURE:
<221> NAME/KEY: CDS
<222> LOCATION: (1)..(318)
<223> OTHER INFORMATION: MBL352-34 VL cDNA

<400> SEQUENCE: 170

```
atc cag atg aca caa tct tca tcc tcc ttg tct gta tct cta gga gac    48
Ile Gln Met Thr Gln Ser Ser Ser Ser Leu Ser Val Ser Leu Gly Asp
1               5                   10                  15 aga gtc acc att act tgc aag gca agt gaa cac att aat agt tgg tta    96
Arg Val Thr Ile Thr Cys Lys Ala Ser Glu His Ile Asn Ser Trp Leu
            20                  25                  30 gcc tgg tat cag caa aaa cca gga aat gct cct agg ctc tta ata tct   144
Ala Trp Tyr Gln Gln Lys Pro Gly Asn Ala Pro Arg Leu Leu Ile Ser
        35                  40                  45 ggt gca acc aat ttg aaa act ggg gtt cct tca aga ttc agt ggc agt   192
Gly Ala Thr Asn Leu Lys Thr Gly Val Pro Ser Arg Phe Ser Gly Ser
    50                  55                  60 gca tct gga aag gat tac act ctc agc att act agt ctt cag act gaa   240
Ala Ser Gly Lys Asp Tyr Thr Leu Ser Ile Thr Ser Leu Gln Thr Glu
65                  70                  75                  80 gat gtt gct act tat tac tgt caa cag tat tgg ggt act ccg tgg acg   288
Asp Val Ala Thr Tyr Tyr Cys Gln Gln Tyr Trp Gly Thr Pro Trp Thr
                85                  90                  95 ttc ggt gga ggc acc aag ctg gaa atc aaa                           318
```

```
Phe Gly Gly Gly Thr Lys Leu Glu Ile Lys
            100                 105

<210> SEQ ID NO 171
<211> LENGTH: 106
<212> TYPE: PRT
<213> ORGANISM: Mus musculus

<400> SEQUENCE: 171

Ile Gln Met Thr Gln Ser Ser Ser Leu Ser Val Ser Leu Gly Asp
1               5                   10                  15

Arg Val Thr Ile Thr Cys Lys Ala Ser Glu His Ile Asn Ser Trp Leu
            20                  25                  30

Ala Trp Tyr Gln Gln Lys Pro Gly Asn Ala Pro Arg Leu Leu Ile Ser
        35                  40                  45

Gly Ala Thr Asn Leu Lys Thr Gly Val Pro Ser Arg Phe Ser Gly Ser
    50                  55                  60

Ala Ser Gly Lys Asp Tyr Thr Leu Ser Ile Thr Ser Leu Gln Thr Glu
65                  70                  75                  80

Asp Val Ala Thr Tyr Tyr Cys Gln Gln Tyr Trp Gly Thr Pro Trp Thr
                85                  90                  95

Phe Gly Gly Gly Thr Lys Leu Glu Ile Lys
            100                 105

<210> SEQ ID NO 172
<211> LENGTH: 345
<212> TYPE: DNA
<213> ORGANISM: Mus musculus
<220> FEATURE:
<221> NAME/KEY: CDS
<222> LOCATION: (1)..(345)
<223> OTHER INFORMATION: MBL352-34 VH cDNA

<400> SEQUENCE: 172 gtt cag ctg cag cag tct ggg gct gag ctt gtg agg cca ggg gcc tca      48
Val Gln Leu Gln Gln Ser Gly Ala Glu Leu Val Arg Pro Gly Ala Ser
1               5                   10                  15 gtc aag ttg tcc tgc aca gct tct ggc ttt aac att aaa gac gac tat      96
Val Lys Leu Ser Cys Thr Ala Ser Gly Phe Asn Ile Lys Asp Asp Tyr
            20                  25                  30 atg cac tgg gtg aag cag agg cct gaa cag ggc ctg gag tgg att gga     144
Met His Trp Val Lys Gln Arg Pro Glu Gln Gly Leu Glu Trp Ile Gly
        35                  40                  45 agg att gat cct gcg aat ggt cat act aaa tat gcc ccg aag ttc cag     192
Arg Ile Asp Pro Ala Asn Gly His Thr Lys Tyr Ala Pro Lys Phe Gln
    50                  55                  60 gac aag gcc act ata act gca gac aca tcc tcc aac aca gcc tac ctg     240
Asp Lys Ala Thr Ile Thr Ala Asp Thr Ser Ser Asn Thr Ala Tyr Leu
65                  70                  75                  80 cag ttc agc agc ctg aca tct gag gac act gcc gtc tat tac tgt aca     288
Gln Phe Ser Ser Leu Thr Ser Glu Asp Thr Ala Val Tyr Tyr Cys Thr
                85                  90                  95 aga atg gga tta cga cga ggc tac tgg ggc caa ggc acc act ctc aca     336
Arg Met Gly Leu Arg Arg Gly Tyr Trp Gly Gln Gly Thr Thr Leu Thr
            100                 105                 110 gtc tcc tca                                                         345
Val Ser Ser
        115

<210> SEQ ID NO 173
<211> LENGTH: 115
```

```
<212> TYPE: PRT
<213> ORGANISM: Mus musculus

<400> SEQUENCE: 173

Val Gln Leu Gln Gln Ser Gly Ala Glu Leu Val Arg Pro Gly Ala Ser
1               5                   10                  15

Val Lys Leu Ser Cys Thr Ala Ser Gly Phe Asn Ile Lys Asp Asp Tyr
            20                  25                  30

Met His Trp Val Lys Gln Arg Pro Glu Gln Gly Leu Glu Trp Ile Gly
        35                  40                  45

Arg Ile Asp Pro Ala Asn Gly His Thr Lys Tyr Ala Pro Lys Phe Gln
    50                  55                  60

Asp Lys Ala Thr Ile Thr Ala Asp Thr Ser Ser Asn Thr Ala Tyr Leu
65                  70                  75                  80

Gln Phe Ser Ser Leu Thr Ser Glu Asp Thr Ala Val Tyr Tyr Cys Thr
                85                  90                  95

Arg Met Gly Leu Arg Arg Gly Tyr Trp Gly Gln Gly Thr Thr Leu Thr
            100                 105                 110

Val Ser Ser
        115
```